US006982169B2

(12) United States Patent
Nicolaides et al.

(10) Patent No.: US 6,982,169 B2
(45) Date of Patent: Jan. 3, 2006

(54) CHEMICAL INHIBITORS OF MISMATCH REPAIR

(75) Inventors: Nicholas C. Nicolaides, Boothwyn, PA (US); Luigi Grasso, Philadelphia, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 495 days.

(21) Appl. No.: 09/760,285

(22) Filed: Jan. 15, 2001

(65) Prior Publication Data

US 2003/0091997 A1 May 15, 2003

(51) Int. Cl.
 *C12N 15/00* (2006.01)
 *C12N 1/16* (2006.01)
 *A01N 27/00* (2006.01)

(52) U.S. Cl. ...................... 435/325; 435/254.2; 504/357
(58) Field of Classification Search ................. 504/357; 435/254.2, 325, 6, 320.1, 455, 68, 19; 514/44; 548/576, 161, 523; 424/248.56
 See application file for complete search history.

(56) References Cited

U.S. PATENT DOCUMENTS

| | | | | |
|---|---|---|---|---|
| 4,419,354 | A | * 12/1983 | Child et al. | 424/248.56 |
| 5,476,952 | A | * 12/1995 | Su et al. | 546/956 |
| 5,885,827 | A | 3/1999 | Wabl et al. | 435/320.1 |
| 5,907,079 | A | 5/1999 | Mak et al. | 800/2 |
| 5,962,249 | A | * 10/1999 | Benton et al. | |
| 6,146,894 | A | 11/2000 | Nicolaides et al. | 435/440 |
| 6,191,268 | B1 | 2/2001 | Liskay et al. | 536/23.5 |
| 6,287,862 | B1 | 9/2001 | delCardayre et al. | 435/440 |
| 2002/0064879 | A1 | * 5/2002 | Zhang | |

FOREIGN PATENT DOCUMENTS

| | | |
|---|---|---|
| CA | CA 2 240 609 | 10/1999 |
| WO | WO 97/05268 | 2/1997 |
| WO | 99/19492 | 4/1999 |

OTHER PUBLICATIONS

Shiosaki, REv Iberoam Micol 2001: 18:123–127, 2001.*
Euler (Caplus Database, AN; 1948:32360, abstract only).*
Kimm (Korean J. of Biochemistry, 1982, vol. 14, No. 1, pp. 1–8, abstract).*
Laduca, Diss, Abstr Int [B], 55, 11, 4741, 1995, Database CancerLit.*
Machala, Mutation Res., 497, 49–62, 2001.*
Krahn, Mutation Res., vol. 46, 27–44, 1997.*
Wigley, Int. J Cancer, 23, 691–696, 1979.*
Slaga, Cancer Res., vol. 38, 1699–1704, 1978.*
Hubbard (Mutation Res. 85/4, p. 264, 1981).*
Traczewska et al. (Acute Microbiologica Polonica, vol. 40, 3, 4, 235–241, 1991).*
LaVoie, Carcinogenesis, vol. 6, pp. 1483–1488, 1985.*
Cerniglia et al., Applied and Environmental Microbiology, vol. 56, No. 3, pp. 661–668, 1990.*
Lamparczyk, Carcinogenesis, vol. 5, 11:1405–1410, 1984.*
Venitt, J. Med, Chem, 41:3748–3752, 1998.*
Ngo et al. Computational complexity, protein structure prediction, and the levinthal paradox pp. 490–495–1994.*
Hoorn et al. Detection of chemical mutagens using muta mouse: a transgenic mouse model pp. 7–10 1993.*
Kotiloglu E. Comparison of target organs of carcinogencity for mutagenic and non–mutagenic chemicals Doga–Turkish Journal of Medical Sciences, 1993 18/2 115–126.*
Hachiya et al. Induction of lacZ mutation by 7,12–dimethylbenz[a]anthracene in various tissues of transgenic mice pp. 283–295 1999.*
Shelton et al. Mutant frequency and molecular analysis of in vivo laci mutations in the bone marrow of big blue rats treated with 7,12–dimethylbenz[a]anthracene pp. 235–242 2000.*
Skolnick et al. From genes to protein structure and function: novel applications of computational approaches in the genomic era pp. 34–39 2000.*
Bork Powers and pitfalls in sequence analysis: The 70% hurdle pp. 398–400 2000.*
Yamamoto et al. A functional and quantitative mutational analysis of p52 mtations in yeast indicates strand biases and different roles of mutations in DMBA– and BBN–induced tumors in rats pp. 700–705 1999.*
Cosma et al. Ha–ras oncogene mutations in cell lines derived from rat tracheal implants exposed in vivo to 7,12–dimethylbenz[a]anthracene pp. 258–263 1990.*
Thompson The use of DNA–Repair–Deficient mutants of chinese hamster ovary cells in studying mutagenesis mechanisms and testing for environmental mutagens pp. 217–246 (1983).*
Dobrovolsky et al. 7,12–Dimethylbenz[a]anthracene–induced mutation in the Ik gene of Tk=/–Mice: automated scoring of lymphocyte clones using a fluorescent viability indicator pp. 283–291 2000.*
Nakazawa et al. Relationship between chemically induced ha–ras mutation and transformation of balb/c 3t3 cells: pp. 202–209 1990.*
Honma et al. Cyrotoxic and mutagenic responses to x–rays and chemical mutagens in normal and p53–mutated human lymphoblastoid cells pp. 89–98 1997.*
Nelson et al. Detection of mutant ha–ras genes in chemically initiated mouse skin epidermis before the development of benign tumors pp. 6398–6402 1992.*

(Continued)

*Primary Examiner*—Dave Trong Nguyen
(74) *Attorney, Agent, or Firm*—Woodcock Washburn LLP

(57) ABSTRACT

Dominant negative alleles of human mismatch repair genes can be used to generate hypermutable cells and organisms. By introducing these genes into cells and transgenic animals, new cell lines and animal varieties with novel and useful properties can be prepared more efficiently than by relying on the natural rate of mutation. Methods of generating mutations in genes of interest and of making various cells mismatch repair defective through the use of chemicals to block mismatch repair in in vivo are disclosed.

29 Claims, 8 Drawing Sheets

OTHER PUBLICATIONS

Proceedings of the american association for cancer research vol. 37, p. 116 1996.*

Mironov, N., et al., "Induction of mutations in mismatch repair –proficient and –deficient human colon cancer cell lines by carcinogens producing different types of DNA damage," *Proceedings of the American Association for Cancer Research Annual Meeting*, 1999, p. 625.

Traczewska, T.M., "Changes of toxicological properties of biodegradation products of anthracene and phenanthrene," *Water Science and Technology*, 2000, 41(12), 31–38.

Aronshtam, A., et al. "Dominant negative mutator mutations in the mutl gene of *Escherichia coli*", *Nucleic Acids Research*, 1996, 24(13), pp 2498–2504.

Cascalho M, et al. "Mismatch repair co–opted by hpermutation", *Science*, 1998, 279(20), pp. 1207–1210.

Polaczek, P., et al. "Functional genetic tests of DNA mismatch repair protein activity in *Saccharomyces cerevisiae*", *Gene*, 1998, 213(1–2), pp. 159–167.

Kong, Q., "PMS2–deficiency diminishes hypermutation of a $\lambda_1$ transgene in young but not older mice," *Molecular Immunology 36*, 1999, 83–91.

Schrader, C.E., et al., "Reduced isotype switching in splenic B cells from mice deficient in mismatch repair enzymes," *J. Exp. Med.*, 1999, 323–330.

Vora, K.A., et al., "Severe attenuation of the B celll immune response in Msh2–deficient mice," *J. Exp. Med.*, 1999, 189(3), 471–481.

Winter, D.B., et al., "Altered spectra of hypermutation in antibodies from mice deficient for the DNA mismatch repair protein PMS2," *Proc. Natl. Acad. Sci. USA*, 1998, 95, 6953–6958.

Fishel, R., et al., "the human mutator gene homolog MSH2 and its association with hereditary nonpolyposis colon cancer," *Cell*, 1993, 7, 1027–1038.

Hamilton, S.R., et al., "The molecular basis of turcot's syndrome," *N. Eng. J. Med.*, 1995, 332(13), 839–847.

Nicolaides, N.C., et al., "Molecular cloning of the N–Terminus of GTBP," *Genomics*, 1996, 31, 395–397.

Parsons, R., et al., "Mismatch repair deficiency in phenotypically normal human cells," *Science*, 1995, 268, 738–740.

Culligan, K.M., et al., "DNA mismatch repair in plants," *Plant Physiol.*, 1997, 15, XP–002099372, 833–839.

Jean, M., et al., "Isolation and characterization of *AtMLH1*, a MutL homologue from *Arabidopsis thaliana*," *Mol. Gen. Genet.*, 1999, 262, XP–000986138, 633–642.

Lipkin, S.M., et al., "MLH3: a DNA mismatch repair gene associated with mammalian microsatellite instability," *Nature Genetics*, 2000, 24, XP–002165243, 27–35.

Harfe, B.D., "DNA mismtach repair and genetic instability" *Annu. Rev. Genet.*, 2000, 34, 359–399.

Nicolaides, N.C., et al., "Mutations of two PMS homologues in hereditary nonpolyposis colon cancer" *Nature*, 1994, 371, 75–80.

Perucho, M., et al., "Cancer of the microsatellite mutator phenotype" *Biol. Chem.*, 1996, 377, 675–684.

Traczewska, T.M., et al., "The metabolism of anthracene and 9, 10–dimethylanathracene by bacteria isolated from waters," *Acta Microbiologica Polonica*, 1991, 40(3/4), 235–241.

Chakravarti, D. et al., "Relating aromatic hydrocarbon–induced DNA adducts and c–H–*ras* mutations in mouse skin papillomas: The role of apurinic sites", *Proc. Natl. Acad. Sci. USA*, Oct. 1995, vol. 92, pp. 10422–10426.

Quian, Y. et al., "Molecular events after antisense inhibition of hMSH2 in a HeLa cell line" *Mutation Research*, Oct. 12, 1998, vol. 418, pp. 61–71.

Yu, Y. et al., "Adriamycin induces large deletions as a major type of mutation in CHO cells", *Mutation Research*, Nov. 1994, vol. 325, pp. 91–98.

Allen, D., et al., "MutS mediates heteroduplex loop formation by a translocation mechanism," *EMBO J.*, 1997, 16(14), 4467–4476.

Baker, S.M., et al., "Male mice defective in the DNA mismatch repair gene PMS2 exhibit abnormal chromosome synapsis in meiosis," *Cell*, 1995, 82, 309–319.

Bell, C.J., et al., "Assignment of 30 microsatellite loci to the linkage map of *arabidopsis*," *Enomics*, 1994, 19, 137–144.

Bjornson, K., et al., "Modulation of MutS ATP hydrolysis by DNA cofactors," *Biochemistry*, 2000, 39, 3176–3183.

Bronner C.E., et al., "Mutation in the DNA mismatch repair gene homologue hMLH1 is associated with hereditary non–polyposis colon cancer," *Nature*, 1994, 368, 258–261.

Cerniglia, C.E., et al., "Stereoselective fungal metabolism of methylated anthracenes," *Appl. Environ. Microbiology*, 1990, 56(3), 661–668.

de Wind, N., et al., "Inactivation of the mouse Msh2 gene results in mismatch repair deficiency, methylation tolerance, hyperrecombination, and predisposition to cancer," *Cell*, 1995, 82, 321–330.

Drummond, J.T., et al., "Isolation of an hMSH2–p160 heterodimer that restores DNA mismatch repair to tumor cells," *Science*, 1995, 268, 1909–1912.

Drummond, J.T., et al., "Cisplatin and adriamycin resistance are associated with mutlα and mismatch repair deficiency in an ovarian tumor cell line," *J. Biological Chemistry*, 1996, 271(33), 19645–19648.

Edelmann, W., et al., "Meiotic pachytene arrest in MLH1–deficient mice," *Cell*, 1996, 85, 1125–1134.

Eshleman, J.R., et al., "Mismatch repair defects in human carcinogenesis," *Human Molecular Genetics*, 1996, 5, 1489–1494.

Galio, L., et al., "ATP hydrolysis–dependent formation of a dynamic ternary nucleoprotein complex with MutS and MutL," *Nucleic Acids Research*, 1999, 27(11), 2325–2331.

Hoang, J., et al., "BAT–26, an indicator of the replication error phenotype in colorectal cancers and cell lines," *Cancer Research*, 1997, 57, 300–303.

Honma, M., et al., "Cytotoxic and mutagenic responses to X–rays and chemical mutagens in normal and p53–mutated human lymphoblastoid cells," *Mutation Research*, 1997, 374, 89–98.

Jiricny, J., et al., "Mismatch repair defects in cancer," *Curr. Opin. Genet. Dev.*, 2000, 10, 157–161.

Karran, P., et al., "Genomic instability and tolerance to alkylating agents," *Cancer Surveys*, 1996, 28, 69–71.

Lamparczyk, H.S., et al., "The metabolism of 9,10–dimethylanthracene by rat liver crosomal preparations," *Carcinogenesis*, 1984, 5(11), 1405–1410.

Leach, F.S., et al., "Mutations of a mutS homolog in hereditary nonpolyposis colorectal cancer," *Cell*, 1993, 75, 1215–1225.

Liu, T., et al., "Microsatellite instability as a predictor of a mutation in a DNA mismatch repair gene in familial colorectal cancer," *Genes, Chromosomes & Cancer,* 2000, 27, 17–25.

McCallum, C.M., "Targeted screening for induced mutations," *Nature Biotechnology,* 2000, 18, 455–457.

Modrich, P., "Mismatch repair, genetic stability, and cancer," *Science,* 1994, 266, 1959–1960.

Myers, S.R., et al., "Bioalkylation and biooxidation of anthracene, in vitro and in vivo," *Biochemical and Biophysical Research Commun.,* 1988, 151(3), 1441–1445.

Neuberger, M., et al., "Mice perform a human repertoire," *Nature,* 1997, 386, 25–26.

Nicolaides, N.C., et al., "Analysis of the 5' region of *PMS*2 reveals heterogeneous transcripts and a novel overlapping gene," *Genomics,* 1995, 29, 329–334.

Nicolaides, N.C., et al., "The jun family members, c–jun and junD, transactivate the human c–myb, promoter via an Ap1–like element," *J. Biological Chemistry,* 1992, 267(27), 19655–19672.

Nicolaides, N.C., et al., "Genomic organization of the human *PMS*2 gene family," *Genomics,* 1995, 30, 195–206.

Nicolaides, N.C., "A naturally occurring *hPMS*2 mutation can confer a dominant negative nutator phenotype," *Mol. Cell. Biol.,* 1998, 18(3), 1635–1641.

Nicolaides, N.C., et al., "Positive autoregulation of c–*myb,* expression via Myb binding sites in the 5' flanking region of the human c–*myb* gene," *Molecular and Cellular Biology,* 1991, 11(12), 6166–6176.

Palombo, F., et al., "Mismatch repair and cancer," *Nature,* 1994, 367, 417.

Papadopoulos, N., et al., "Mutations of *GTBP* in genetically unstable cells," *Science,* 1995, 268, 1915–1917.

Papadopoulos, N., et al., "Mutation of a *mutL* homolog in hereditary colon cancer," *Science,* 1994, 263, 1625–1629.

Parsons, R., et al., "hypermutability and mismatch repair deficiency in RER+ tumor cells," *Cell,* 1993, 75, 1227–1236.

Peinado, M.A., et al., "Isolation and characterization of allelic losses and gains in colorectal tumors by arbitrarily primed polymerase chain reaction," *Proc. Natl. Acad. Sci. USA,* 1992, 89, 10065–10069.

Prolla, T.A., et al., "MLH1, PMS1, and MSH2 interactions during the initiation of DNA mismatch repair in yeast," *Science,* 1994, 265, 1091–1093.

Spampinato, C., et al., "The MutL ATPase is required for mismatch repair," *J. Biological Chemistry,* 2000, 275(13), 9863–9869.

Strand, M., et al., "Destabilization of tracts of simple repetitive DNA in yeast by mutations affecting DNA mismatch repair," *Nature,* 1993, 365, 274–276.

Su, S., et al., "Dispair specificity of methyl–directed DNA mismatch correction In Vitro," *J. Biological Chemistry,* 1988, 263(14), 6829–6835.

Wheeler, J.M.D., et al., "The role of hypermethylation of the hMLH1 promoter region in HNPCC versus MSI+sporadic colorectal cancers" *J. Med. Genet.,* 2000, 588–592.

Liu et al., "Analysis of Mismatch Repair Genes in Hereditary Non–polyposis Colorectal Cancer Patients", *Nature Medicine,* Feb. 1996, 2(2), 169–174.

Ma et al., "Dominant Negative Expression of hPMS2 Creates Isogenic Mismtach Repair Deficient Human Colon Cancer Cell Lines", *Proc. Am. Assoc. Cancer Res.,* Mar. 1998, 39, p. 460 (Abstract #3130).

* cited by examiner 17 day old plants

CHEMICAL INHIBITORS OF MISMATCH REPAIR

TECHNICAL FIELD OF THE INVENTION

The invention is related to the area of mutagenesis. In particular it is related to the field of blocking specific DNA repair processes.

BACKGROUND OF THE INVENTION

Mismatch repair (MMR) is a conserved DNA repair process that is involved in post-replicative repair of mutated DNA sequences that occurs after genome replication. The process involves a group of gene products, including the mutS homologs GTBP, hMSH2, and hMSH3 and the mutL homologs hMLH1, hPMS1, and hPMS2 (Bronner, C. E. et al. (1994) Nature 368:258–261; Papadopoulos, N. et al. (1994) Science 263:1625–1629; Leach, F. S. et al. (1993) Cell 75:1215–1225; Nicolaides, N. C. et al. (1994) Nature 371:75–80) that work in concert to correct mispaired mono-, di-, and tri-nucleotides, point mutations, and to monitor for correct homologous recombination. Germline mutations in any of the genes involved in this process results in global point mutations, and instability of mono, di and tri-nucleotide repeats (a feature referred to as microsatellite instability (MI)), throughout the genome of the host cell. In man, genetic defects in MMR results in the predisposition to hereditary nonpolyposis colon cancer, a disease in which tumors retain a diploid genome but have widespread MI (Bronner, C. E. et al. (1994) Nature 368:258–261; Papadopoulos, N. et al. (1994) Science 263:1625–1629; Leach, F. S. et al. (1993) Cell 75:1215–1225; Nicolaides, N. C. et al. (1994) Nature 371:75–80; Harfe B. D., and S. Jinks-Robertson (2000) An. Rev. Genet. 34:359–399; Modrich, P. (1994) Science 266:1959–1960). Though the mutator defect that arises from MMR deficiency can affect any DNA sequence, microsatellite sequences are particularly sensitive to MMR abnormalities (Peinado, M. A. et al. (1992) Proc. Natl. Acad. Sci. USA 89:10065–10069). Microsatellite instability is therefore a useful indicator of defective MMR. In addition to its occurrence in virtually all tumors arising in HNPCC patients, MI is found in a small fraction of sporadic tumors with distinctive molecular and phenotypic properties that is due to defective MMR (Perucho, M. (1996) Biol. Chem. 377:675–684).

MMR deficiency leads to a wide spectrum of mutations (point mutations, insertions, deletions, recombination, etc.) that can occur throughout the genome of a host cell. This effect has been found to occur across a diverse array of organisms ranging from but not limited to unicellular microbes, such as bacteria and yeast, to more complex organisms such as Drosophila and mammals, including mice and humans (Harfe B. D., and S. Jinks-Robertson (2000) An. Rev. Genet. 34:359–399; Modrich, P. (1994) Science 266:1959–1960). The ability to block MMR in a normal host cell or organism can result in the generation of genetically altered offspring or sibling cells that have desirable output traits for applications such as but not limited to agriculture, pharmaceutical, chemical manufacturing and specialty goods. A chemical method that can block the MMR process is beneficial for generating genetically altered hosts with commercially valuable output traits. A chemical strategy for blocking MMR in vivo offers a great advantage over a recombinant approach for producing genetically altered host organisms. One advantage is that a chemical approach bypasses the need for introducing foreign DNA into a host, resulting in a rapid approach for inactivating MMR and generating genetically diverse offspring or sib cells. Moreover, a chemical process is highly regulated in that once a host organism with a desired output trait is generated, the chemical is removed from the host and its MMR process would be restored, thus fixing the genetic alteration in subsequent generations. The invention described herein is directed to the discovery of small molecules that are capable of blocking MMR, thus resulting in host organisms with MI, a hallmark of MMR deficiency (Peinado, M. A. et al. (1992) Proc. Natl. Acad. Sci. USA 89:10065–10069; Perucho, M. (1996) Biol. Chem. 377:675–684; Wheeler, J. M. et al. (2000) J. Med. Genet. 37:588–592; Hoang, J. M. et al. (1997) Cancer Res. 57:300–303). Moreover, host organisms exhibiting MI are then selected for to identify subtypes with new output traits, such as but not limited to mutant nucleic acid molecules, polypeptides, biochemicals, physical appearance at the microscopic and/or macroscopic level, or phenotypic alterations in a whole organism. In addition, the ability to develop MMR defective host cells by a chemical agent provides a valuable method for creating genetically altered cell hosts for product development. The invention described herein is directed to the creation of genetically altered cell hosts via the blockade of MMR using chemical agents in vivo.

The advantages of the present invention are further described in the examples and figures described within this document.

SUMMARY OF THE INVENTION

The invention provides methods for rendering cells hypermutable by blocking MMR activity with chemical agents.

The invention also provides genetically altered cell lines which have mutations introduced through interruption of mismatch repair.

The invention further provides methods to produce an enhanced rate of genetic hypermutation in a cell.

The invention encompasses methods of mutating a gene of interest in a cell, methods of creating cells with new phenotypes, and methods of creating cells with new phenotypes and a stable genome.

The invention also provides methods of creating genetically altered whole organisms and methods of creating whole organisms with new phenotypes.

These and other objects of the invention are provided by one or more of the embodiments described below.

In one embodiment of the invention, a method for screening chemical compounds that block mismatch repair (MMR) is provided. An MMR-sensitive reporter gene containing an out-of-frame polynucleotide repeat in its coding region is introduced into an MMR proficient cell. The cell is grown in the presence of chemicals. Chemicals that alter the genetic structure of the polynucleotide repeat yield a biologically active reporter gene product. Chemicals that disrupt the polynucleotide repeat are identified as MMR blocking agents.

In another embodiment of the invention, an isolated MMR blocking chemical is provided. The chemical can block MMR of a host cell, yielding a cell that exhibits an enhanced rate of hypermutation.

In another embodiment of the invention, a method is provided for introducing a mutation into a gene of interest. A chemical that blocks mismatch repair is added to the culture of a cell line. The cells become hypermutable as a result of the introduction of the chemical. The cell further comprises a gene of interest. The cell is cultured and tested to determine whether the gene of interest harbors a mutation.

In another embodiment of the invention, a method is provided for producing new phenotypes of a cell. A chemical that blocks mismatch repair is added to a cell culture. The cell becomes hypermutable as a result of the introduction of the chemical. The cell is cultured and tested for the expression of new phenotypes.

In another embodiment of the invention, a method is provided for restoring genetic stability in a cell in which mismatch repair is blocked via a chemical agent. The chemical is removed from the cell culture and the cell restores its genetic stability.

In another embodiment of the invention, a method is provided for restoring genetic stability in a cell with blocked mismatch repair and a newly selected phenotype. The chemical agent is removed from the cell culture and the cell restores its genetic stability and the new phenotype is stable.

In another embodiment of the invention, a chemical method for blocking MMR in plants is provided. The plant is grown in the presence of a chemical agent. The plant is grown and exhibits an enhanced rate of hypermutation.

In another embodiment of the invention, a method for screening chemical inhibitors of MMR in plants in vivo is provided. MMR-sensitive plant expression vectors are engineered. The reporter vectors are introduced into plant hosts. The plant is grown in the presence of a chemical agent. The plant is monitored for altered reporter gene function.

In another embodiment of the invention, a method is provided for introducing a mutation into a gene of interest in a plant. A chemical that blocks mismatch repair is added to a plant. The plant becomes hypermutable as a result of the introduction of the chemical. The plant further comprises a gene of interest. The plant is grown. The plant is tested to determine whether the gene of interest harbors a mutation.

In another embodiment of the invention, a method is provided for producing new phenotypes of a plant. A chemical that blocks mismatch repair is added to a plant. The plant becomes hypermutable as a result of the introduction of the chemical. The plant is grown and tested for the expression of new phenotypes.

In another embodiment of the invention, a method is provided for restoring genetic stability in a plant in which mismatch repair is blocked via a chemical agent. The chemical is removed from the plant culture and the plant restores its genetic stability.

In another embodiment of the invention, a method is provided for restoring genetic stability in a plant with blocked mismatch repair and a newly selected phenotype. The chemical agent is removed from the plant culture and the plant restores its genetic stability and the new phenotype is stable.

These and other embodiments of the invention provide the art with methods that can generate enhanced mutability in microbes, organisms of the protista class, insect cells, mammalian cells, plants, and animals as well as providing cells, plants and animals harboring potentially useful mutations.

Cells were cultured in the presence of DMA for 14–17 days. Genomic DNA was isolated and BAT26 microsatellites were analyzed by PCR and gel electrophoresis. (A) Markers were analyzed by PCR using total genomic DNA from 40 samples of treated and untreated cells. Bottom band is the product with the expected wild type (WT) allele size. The asterisk indicates the presence of a new allele in cells treated with DMA. No new alleles were observed in control cells. (B) BAT26 markers from DMA-treated and untreated cells were amplified and cloned into T-tailed vectors. Recombinant clones were then reamplified using BAT26 primers and run on 4% agarose gels and stained with ethidium bromide. Shown is a representative sampling of clones whereby clones with altered molecular weights were observed in DMA treated cells (bottom panel) but not in control cells (top panel). The asterisk indicates markers with altered molecular weight.

Figure 4:
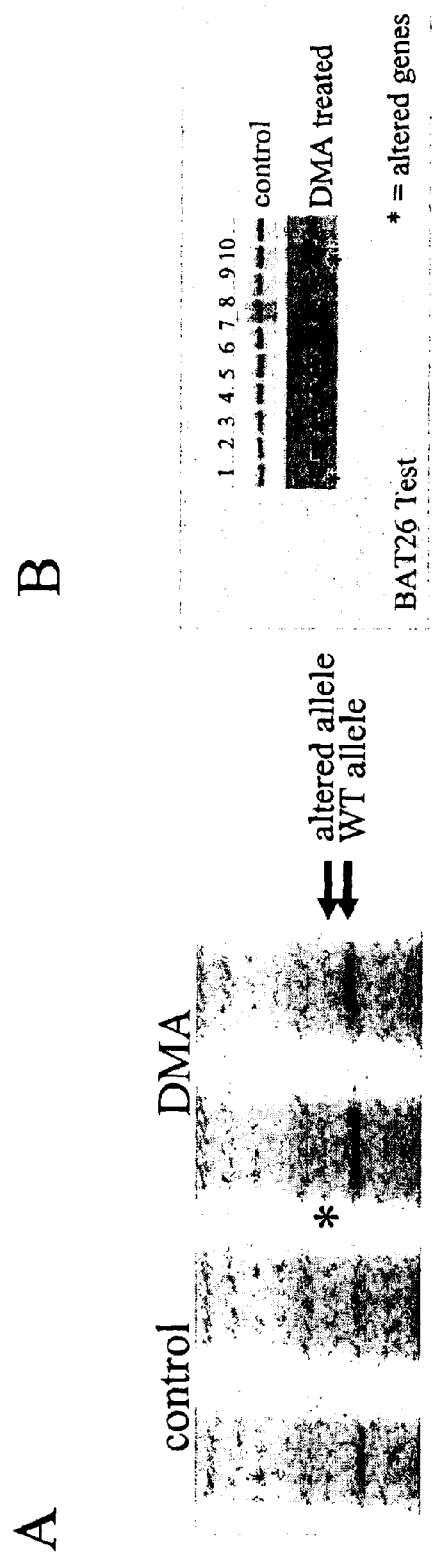

FIG. 4 shows shifting of endogenous microsatellites in human cells induced by a chemical inhibitor of MMR. Shifting of endogenous microsatellites in human cells induced by DMA in human 293 cells. Cells were cultured in the presence of DMA for 14–17 days. Genomic DNA was isolated and BAT26 microsatellites were analyzed by PCR and gel electrophoresis. (A) Markers were analyzed by PCR using total genomic DNA from 40 samples of treated and untreated cells. Bottom band is the product with the expected wild type (WT) allele size. The asterisk indicates the presence of a new allele in cells treated with DMA. No new alleles were observed in control cells. (B) BAT26 markers from DMA-treated and untreated cells were amplified and cloned into T-tailed vectors. Recombinant clones were then reamplified using BAT26 primers and run on 4% agarose gels and stained with ethidium bromide. Shown is a representative sampling of clones whereby clones with altered molecular weights were observed in DMA treated cells (bottom panel) but not in control cells (top panel). The asterisk indicates markers with altered molecular weight.

Figure 5:
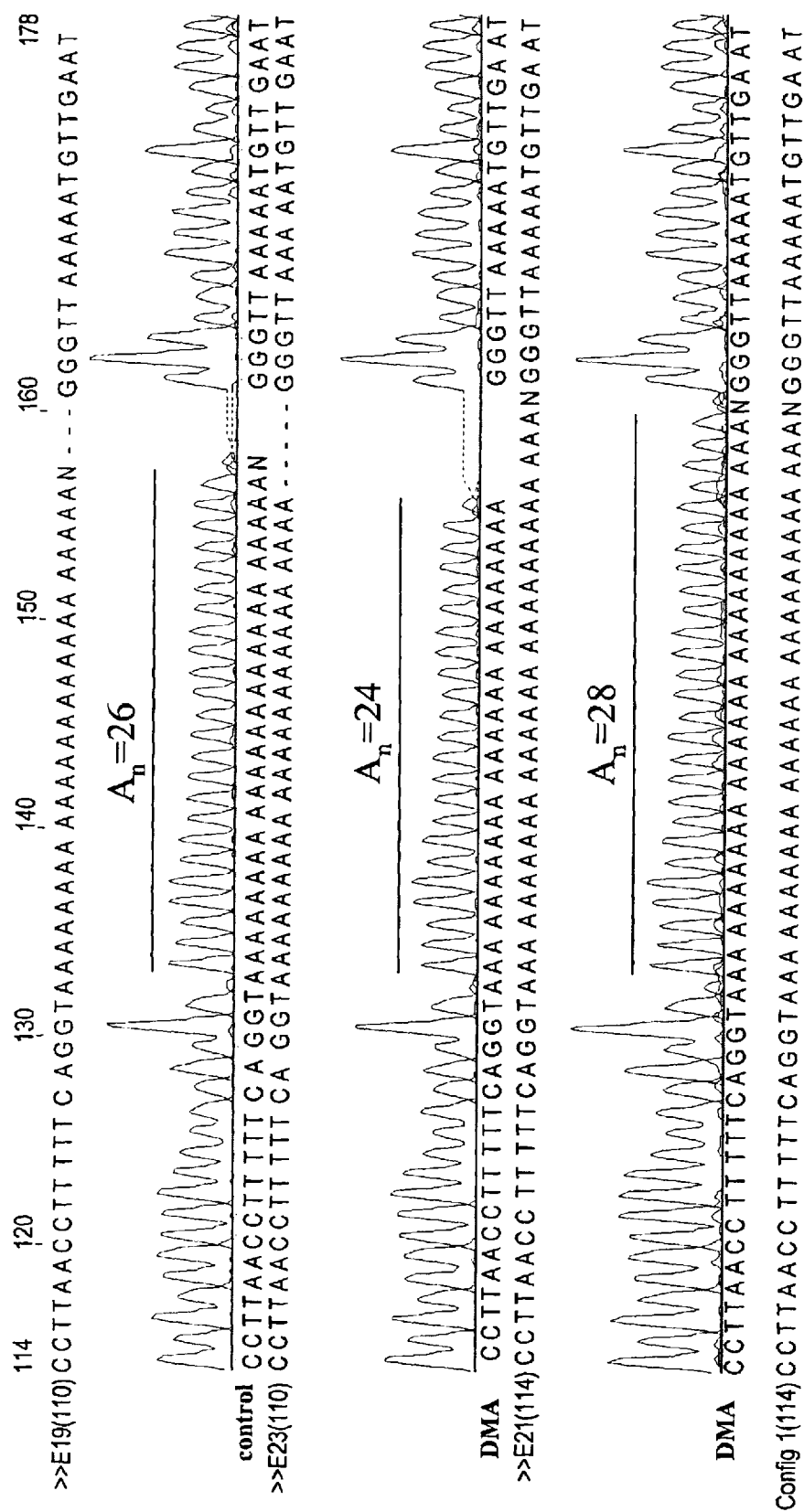

FIG. 5 shows sequence analysis of microsatellites from cells treated with chemical inhibitors of MMR with altered repeats. Sequence analysis of recombinant clones containing the BAT26 markers shows alterations within the endogenous polyA repeats in 293 cells treated with 250 mm DMA but not in markers obtained from control cells (top sequence). Shown is a sequence alignment from 3 clones. Sequence was aligned using Vector NTI software.

Figure 6:
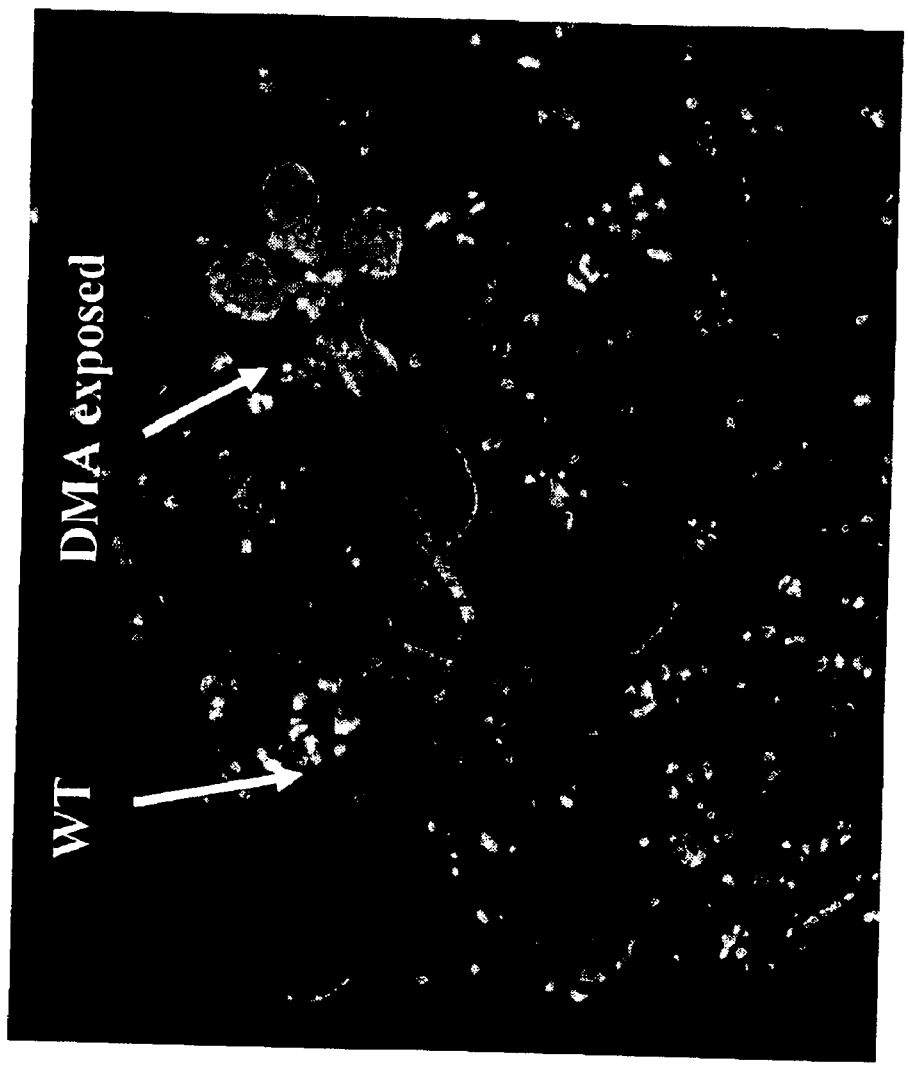

FIG. 6 shows generation of host organisms with new phenotypes using a chemical blocker of MMR. Chemical inhibitors of MMR blocks spell check process leading to genetic alterations and new output traits. Shown here are offspring from control (WT) or DMA exposed *Arabidopsis thaliana* plants grown in standard soil conditions for 17 days. Six percent of the offspring from DMA treated plants had the small light green appearance. No plants with altered phenotypes were observed in the 150 plants from control or EMS mutagenized offspring. These data demonstrate the ability to generate a high rate of genetic alteration in host organisms by blockade of MMR in vivo that can lead to new output traits.

Figure 7:
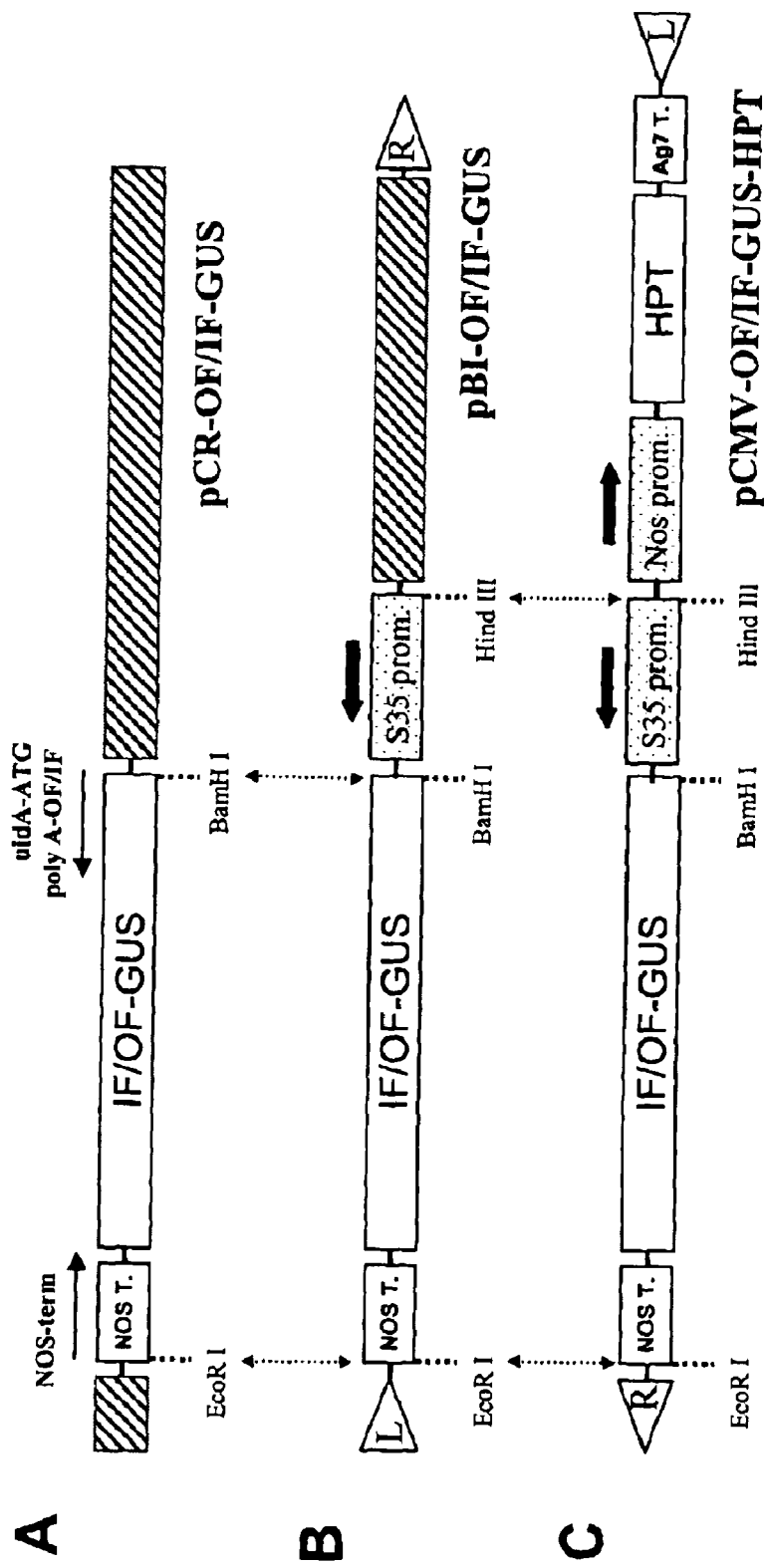

FIG. 7 shows a schematic diagram of MMR-sensitive reporter gene for plants. Binary vectors carrying the in-frame (IF) or out-of-frame (OF) version of the b-glucuronidase (GUS) gene. A) If-GUS and OF-GUS genes, including the nopaline synthase terminator (NOS T.), were obtained by PCR using the NOS-term. and uidA-ATG poly A-OF/IF primers. PCR products were cloned in the TA cloning vector pCR2.1 and sequenced. B) IF-GUS or OF-GUS genes were then cloned into the EcoR I and BamH I sites of the pBI-121 vector, which carries the Cauliflower Mosaic Virus S35 promoter (S35 prom.). C) The cassette containing the S35 promoter, the IF/OF-GUS gene, and the NOS T. was subsequently cloned into the EcoR I and Hind III sites of the pGPTV-HPT binary vector, to generate pCMV-IF-GUS-HPT or pCMV-OF-GUS-HPT constructs. HPT, hygromycin phosphotransferase gene. L, T-DNA left border. R, T-DNA right border. Solid arrows indicate direction of transcription. Dotted arrows indicate subcloning sites. Ag7, gene 7 terminator.

Figure 8:
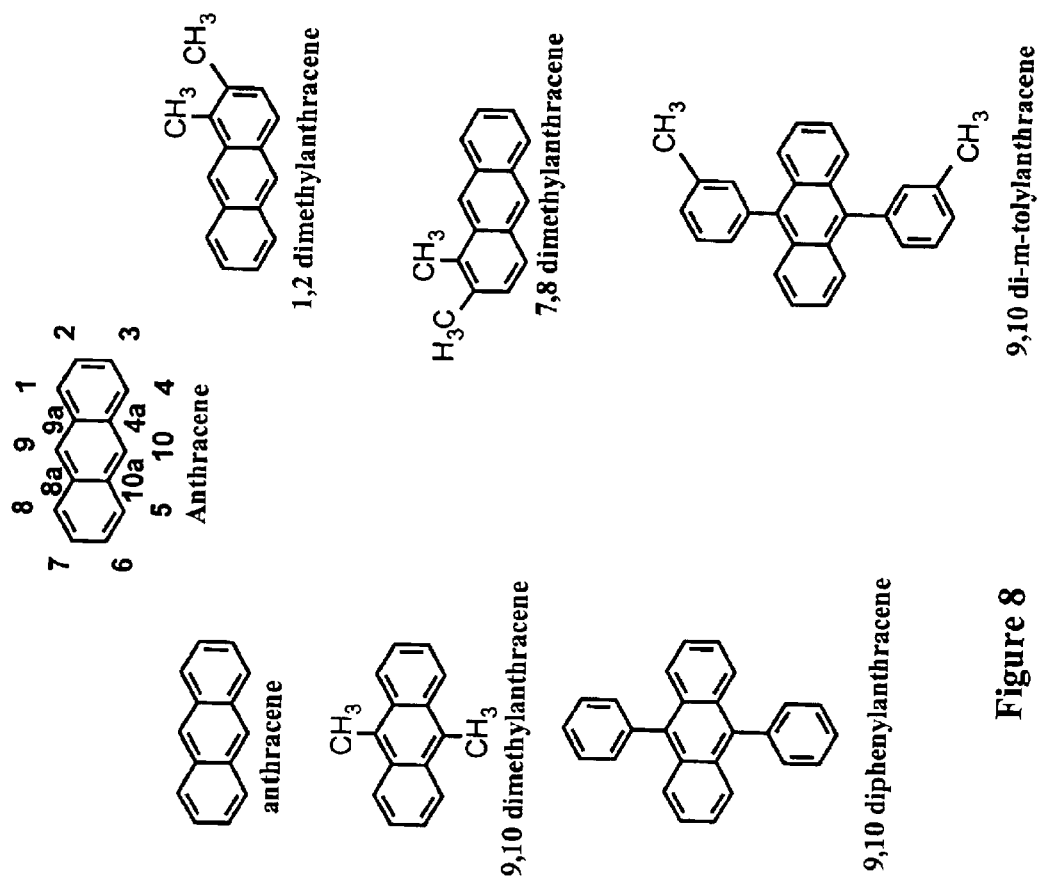

FIG. 8 shows derivatives of lead compounds and thereof that are inhibitors of MMR in vivo. 9, 10 dimethyl anthracene and anthracene analogs are effective chemical inhibitors of mismatch repair in vivo.

DETAILED DESCRIPTION OF THE INVENTION

Various definitions are provided herein. Most words and terms have the meaning that would be attributed to those words by one skilled in the art. Words or terms specifically defined herein have the meaning provided in the context of the present invention as a whole and as are typically understood by those skilled in the art. Any conflict between an art-understood definition of a word or term and a definition of the word or term as specifically taught herein shall be resolved in favor of the latter. Headings used herein are for convenience and are not to be construed as limiting.

As used herein the term "anthracene" refers to the compound anthracene. However, when referred to in the general sense, such as "anthracenes," "an anthracene" or "the anthracene," such terms denote any compound that contains the fused triphenyl core structure of anthracene, i.e.,

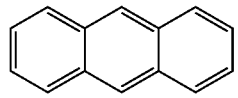

regardless of extent of substitution.

In certain preferred embodiments of the invention, the anthracene has the formula:

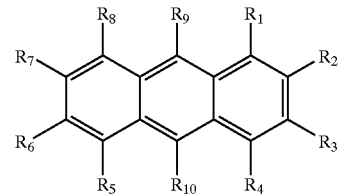

wherein $R_1$–$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;

wherein said heteroalkyl, heteroaryl, and substituted heteroaryl contain at least one heteroatom that is oxygen, sulfur, a metal atom, phosphorus, silicon or nitrogen; and wherein said substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkyloxy, guanidino, alkoxycarbonyl, alkoxy, hydroxy, carboxy and amino;

and wherein said amino groups optionally substituted with an acyl group, or 1 to 3 aryl or lower alkyl groups;

or wherein any two of $R_1$–$R_{10}$ can together form a polyether;

or wherein any two of $R_1$–$R_{10}$ can, together with the intervening carbon atoms of the anthracene core, form a crown ether.

As used herein, "alkyl" refers to a hydrocarbon containing from 1 to about 20 carbon atoms. Alkyl groups may straight, branched, cyclic, or combinations thereof. Alkyl groups thus include, by way of illustration only, methyl, ethyl, propyl, isopropyl, butyl, isobutyl, cyclopentyl, cyclopentylmethyl, cyclohexyl, cyclohexylmethyl, and the like. Also included within the definition of "alkyl" are fused and/or polycyclic aliphatic cyclic ring systems such as, for example, adamantane. As used herein the term "alkenyl" denotes an alkyl group having at least one carbon-carbon double bond. As used herein the term "alkynyl" denotes an alkyl group having at least one carbon-carbon triple bond.

In some preferred embodiments, the alkyl, alkenyl, alkynyl, aryl, aryloxy, and heteroaryl substituent groups described above may bear one or more further substituent groups; that is, they may be "substituted". In some preferred embodiments these substituent groups can include halogens (for example fluorine, chlorine, bromine and iodine), CN, $NO_2$, lower alkyl groups, aryl groups, heteroaryl groups, aralkyl groups, aralkyloxy groups, guanidino, alkoxycarbonyl, alkoxy, hydroxy, carboxy and amino groups. In addition, the alkyl and aryl portions of aralkyloxy, arylalkyl, arylsulfonyl, alkylsulfonyl, alkoxycarbonyl, and aryloxycarbonyl groups also can bear such substituent groups. Thus, by way of example only, substituted alkyl groups include, for example, alkyl groups fluoro-, chloro-, bromo- and iodoalkyl groups, aminoalkyl groups, and hydroxyalkyl groups, such as hydroxymethyl, hydroxyethyl, hydroxypropyl, hydroxybutyl, and the like. In some preferred embodiments such hydroxyalkyl groups contain from 1 to about 20 carbons.

As used herein the term "aryl" means a group having 5 to about 20 carbon atoms and which contains at least one aromatic ring, such as phenyl, biphenyl and naphthyl. Preferred aryl groups include unsubstituted or substituted phenyl and naphthyl groups. The term "aryloxy" denotes an aryl group that is bound through an oxygen atom, for example a phenoxy group.

In general, the prefix "hetero" denotes the presence of at least one hetero (i.e., non-carbon) atom, which is in some preferred embodiments independently one to three O, N, S, P, Si or metal atoms. Thus, the term "heteroaryl" denotes an aryl group in which one or more ring carbon atom is replaced by such a heteroatom. Preferred heteroaryl groups include pyridyl, pyrimidyl, pyrrolyl, furyl, thienyl, and imidazolyl groups.

The term "aralkyl" (or "arylalkyl") is intended to denote a group having from 6 to 15 carbons, consisting of an alkyl group that bears an aryl group. Examples of aralkyl groups include benzyl, phenethyl, benzhydryl and naphthylmethyl groups.

The term "alkylaryl" (or "alkaryl") is intended to denote a group having from 6 to 15 carbons, consisting of an aryl group that bears an alkyl group. Examples of aralkyl groups include methylphenyl, ethylphenyl and methylnaphthyl groups.

The term "arylsulfonyl" denotes an aryl group attached through a sulfonyl group, for example phenylsulfonyl. The term "alkylsulfonyl" denotes an alkyl group attached through a sulfonyl group, for example methylsulfonyl.

The term "alkoxycarbonyl" denotes a group of formula —C(=O)—O—R where R is alkyl, alkenyl, or alkynyl, where the alkyl, alkenyl, or alkynyl portions thereof can be optionally substituted as described herein.

The term "aryloxycarbonyl" denotes a group of formula —C(=O)—O—R where R is aryl, where the aryl portion thereof can be optionally substituted as described herein.

The terms "arylalkyloxy" or "aralkyloxy" are equivalent, and denote a group of formula —O—R'—R", where R' is R is alkyl, alkenyl, or alkynyl which can be optionally substituted as described herein, and wherein R" denotes a aryl or substituted aryl group.

The terms "alkylaryloxy" or "alkaryloxy" are equivalent, and denote a group of formula —O—R'—R", where R' is an aryl or substituted aryl group, and R" is alkyl, alkenyl, or alkynyl which can be optionally substituted as described herein.

As used herein, the term "aldehyde group" denotes a group that bears a moiety of formula —C(=O)—H. The term "ketone" denotes a moiety containing a group of formula —R—C(=O)—R=, where R and R= are independently alkyl, alkenyl, alkynyl, aryl, heteroaryl, aralkyl, or alkaryl, each of which may be substituted as described herein.

As used herein, the term "ester" denotes a moiety having a group of formula —R—C(=O)—O—R= or —R—O—C(=O)—R= where R and R= are independently alkyl, alkenyl, alkynyl, aryl, heteroaryl, aralkyl, or alkaryl, each of which may be substituted as described herein.

The term "ether" denotes a moiety having a group of formula —R—O—R= or where R and R= are independently alkyl, alkenyl, alkynyl, aryl, heteroaryl, aralkyl, or alkaryl, each of which may be substituted as described herein.

The term "crown ether" has its usual meaning of a cyclic ether containing several oxygen atoms. As used herein the term "organosulfur compound" denotes aliphatic or aromatic sulfur containing compounds, for example thiols and disulfides. The term "organometallic group" denotes an organic molecule containing at least one metal atom.

The term "organosilicon compound" denotes aliphatic or aromatic silicon containing compounds, for example alkyl and aryl silanes.

The term "carboxylic acid" denotes a moiety having a carboxyl group, other than an amino acid.

As used herein, the term "amino acid" denotes a molecule containing both an amino group and a carboxyl group. In some preferred embodiments, the amino acids are α-, β-, γ- or δ-amino acids, including their stereoisomers and racemates. As used herein the term "L-amino acid" denotes an α-amino acid having the L configuration around the α-carbon, that is, a carboxylic acid of general formula CH(COOH)(NH$_2$)-(side chain), having the L-configuration. The term "D-amino acid" similarly denotes a carboxylic acid of general formula CH(COOH)(NH$_2$)-(side chain), having the D-configuration around the α-carbon. Side chains of L-amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, *Biochemistry*, Second Edition, Worth Publishers, Inc, 1975, pages 72–77, incorporated herein by reference. Amino acid substituents may be attached through their carbonyl groups through the oxygen or carbonyl carbon thereof, or through their amino groups, or through functionalities residing on their side chain portions.

As used herein "polynucleotide" refers to a nucleic acid molecule and includes genomic DNA cDNA, RNA, mRNA and the like.

As used herein "antisense oligonucleotide" refers to a nucleic acid molecule that is complementary to at least a portion of a target nucleotide sequence of interest and specifically hybridizes to the target nucleotide sequence under physiological conditions.

As used herein "inhibitor of mismatch repair" refers to an agent that interferes with at least one function of the mismatch repair system of a cell and thereby renders the cell more susceptible to mutation.

As used herein "hypermutable" refers to a state in which a cell in vitro or in vivo is made more susceptible to mutation through a loss or impairment of the mismatch repair system.

As used herein "agents," "chemicals," and "inhibitors" when used in connection with inhibition of MMR refers to chemicals, oligonucleotides, analogs of natural substrates, and the like that interfere with normal function of MMR.

Methods for developing hypermutable cells and whole organisms have been discovered by taking advantage of the conserved mismatch repair (MMR) process of a host. Dominant negative alleles of MMR genes, when introduced into cells or transgenic animals, increase the rate of spontaneous mutations by reducing the effectiveness of DNA repair and thereby render the cells or animals hypermutable. Hypermutable microbes, protozoans, insects, mammalian cells, plants or whole animals can then be utilized to develop new mutations in a gene of interest. It has been discovered that chemicals that block MMR, and thereby render cells hypermutable, is an efficient way to introduce mutations in cells and genes of interest. In addition to destabilizing the genome of cells exposed to chemicals that inhibit MMR activity may be done transiently, allowing cells to become hypermutable, and removing the chemical exposure after the desired effect (e.g., a mutation in a gene of interest) is achieved. The chemicals that inhibit MMR activity that are suitable for use in the invention include, but are not limited to, anthracene derivatives, nonhydrolyzable ATP analogs, ATPase inhibitors, antisense oligonucleotides that specifically anneal to polynucleotides encoding mismatch repair proteins, DNA polymerase inhibitors, and exonuclease inhibitors. These chemicals can enhance the rate of mutation due to inactivation of MMR yielding clones or subtypes with altered biochemical properties. Methods for identifying chemical compounds that inhibit MMR in vivo are also described herein.

The process of MMR, also called mismatch proofreading, is carried out by a group of protein complexes in cells ranging from bacteria to man (Harfe B. D., and S. Jinks-Robertson (2000) *An. Rev. Genet.* 34:359–399; Modrich, P. (1994) *Science* 266:1959–1960). An MMR gene is a gene that encodes for one of the proteins of such a mismatch repair complex. Although not wanting to be bound by any particular theory of mechanism of action, an MMR complex is believed to detect distortions of the DNA helix resulting from non-complementary pairing of nucleotide bases. The non-complementary base on the newer DNA strand is excised, and the excised base is replaced with the appropriate base, which is complementary to the older DNA strand. In this way, cells eliminate many mutations that occur as a result of mistakes in DNA replication.

Dominant negative alleles cause an MMR defective phenotype even in the presence of a wild-type allele in the same cell. An example of a dominant negative allele of an MMR gene is the human gene hPMS2-134 (SEQ ID NO:25), which carries a truncating mutation at codon 134 (Nicolaides, N. C. et al. (1998) *Mol. Cell. Biol.* 18:1635–1641). The mutation causes the product of this gene to abnormally terminate at the position of the 134th amino acid, resulting in a shortened polypeptide containing the N-terminal 133 amino acids (SEQ ID NO:24). Such a mutation causes an increase in the rate of mutations, which accumulate in cells after DNA replication. Expression of a dominant negative allele of a mismatch repair gene results in impairment of mismatch repair activity, even in the presence of the wild-type allele.

The MMR process has been shown to be blocked by the use of nonhydrolyzable forms of ATP (Galio, L. et al. (1999) *Nucl. Acids Res.* 27:2325–2331; Allen, D. J. et al. (1997) *EMBO J.* 16:4467–4416; Bjornson, K. P. et al. (2000) *Biochem.* 39–3176–3183). However, it has not been demonstrated that chemicals can block MMR activity in cells. Such chemicals can be identified by screening cells for defective MMR activity. Cells from bacteria, yeast, fungi, insects, plants, animals, and humans can be screened for defective mismatch repair. Genomic DNA, cDNA, or mRNA from any cell can be analyzed for variations from the wild type sequences in cells or organisms grown in the presence of MMR blocking compounds. Various techniques of screening can be used. The suitability of such screening assays, whether natural or artificial, for use in identifying hypermutable cells, insects, fungi, plants or animals can be evaluated by testing the mismatch repair activity caused by a compound or a mixture of compounds, to determine if it is an MMR inhibitor.

A cell, a microbe, or a whole organism such as an insect, fungus, plant or animal in which a chemical inhibitor of mismatch repair has been treated will become hypermutable. This means that the spontaneous mutation rate of such cells or whole organism is elevated compared to cells or animals without such treatment. The degree of elevation of the spontaneous mutation rate can be at least 2-fold, 5-fold, 10-fold, 20-fold, 50-fold, 100-fold, 200-fold, 500-fold, or 1000-fold that of the normal cell or animal. The use of chemical mutagens such as, but limited to, N-methyl-N'-nitro-N-nitrosoguanidine (MNNG), methane sulfonate, dimethyl sulfonate, O6-methyl benzadine, ethyl methanesulfonate (EMS), methylnitrosourea (MNU), ethylnitrosourea (ENU), etc. can be used in MMR defective cells or whole organisms to increase the rates an additional 10 to 100 fold that of the MMR deficiency itself.

According to one aspect of the invention, a screening assay for identifying chemical inhibitors of MMR is developed and employed. A chemical compound can be in any form or class ranging from but not limited to amino acid, steroidal, aromatic, or lipid precursors. The chemical compound can be naturally occurring or made in the laboratory. The screening assay can be natural such as looking for altered endogenous repeats within an host organism's genome (as demonstrated in FIGS. 4 and 5), or made in the laboratory using an MMR-sensitive reporter gene as demonstrated in FIGS. 1–3).

The chemical compound can be introduced into the cell by supplementing the growth medium, or by intracellular delivery such as but not limited to using microinjection or carrier compounds.

According to another aspect of the invention, a chemical compound from the anthracene class can be exposed to MMR proficient cells or whole organism hosts, the host is grown and screened for subtypes containing genetically altered genes with new biochemical features.

The anthracene compounds that are suitable for use in the invention include, but are not limited to anthracenes having the formula:

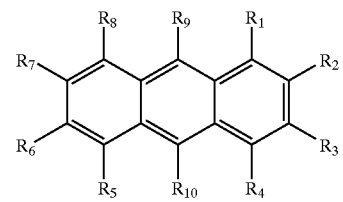

wherein $R_1$–$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;

wherein said heteroalkyl, heteroaryl, and substituted heteroaryl contain at least one heteroatom that is oxygen, sulfur, a metal atom, phosphorus, silicon or nitrogen; and wherein said substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkyloxy, guanidino, alkoxycarbonyl, alkoxy, hydroxy, carboxy and amino;

and wherein said amino groups optionally substituted with an acyl group, or 1 to 3 aryl or lower alkyl groups;

or wherein any two of $R_1$–$R_{10}$ can together form a polyether; or wherein any two of $R_1$–$R_{10}$ can, together with the intervening carbon atoms of the anthracene core, form a crown ether.

The method of the invention also encompasses inhibiting MMR with an anthracene of the above formula wherein $R_5$ and $R_6$ are hydrogen, and the remaining substituents are as described above.

The some embodiments, in the anthracene compound $R_1$–$R_{10}$ are independently hydrogen, hydroxyl, alkyl, aryl, arylaklyl, or hydroxyalkyl. In other embodiments, $R_1$–$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl.

In specific embodiments of the invention the anthracenes include, but are not limited to 1,2-dimethylanthracene, 9,10-dimethyl anthracene, 7,8-dimethylanthracene, 9,10-diphenylanthracene, 9,10-dihydroxymethylanthracene, 9-hydroxymethyl-10-methylanthracene, dimethylanthracene-1,2-diol, 9-hydroxymethyl-10-methylanthracene-1,2-diol, 9-hydroxymethyl-10-methylanthracene-3,4-diol, 9,10-di-m-tolyanthracene, and the like.

The chiral position of the side chains of the anthracenes is not particularly limited and may be any chiral position and any chiral analog. The anthracenes may also comprise a stereoisomeric forms of the anthracenes and includes any isomeric analog.

Examples of hosts are but not limited to cells or whole organisms from human, primate, mammal, rodent, plant, fish, reptiles, amphibians, insects, fungi, yeast or microbes of prokaryotic origin.

Yet another aspect of the invention is the use of ATP analogs capable of blocking ATPase activity required for MMR. MMR reporter cells are screened with ATP compound libraries to identify those compounds capable of blocking MMR in vivo. Examples of ATP analogs that are useful in blocking MMR activity include, but are not limited to, nonhydrolyzable forms of ATP such as AMP-PNP and ATP[gamma]S block the MMR activity (Galio, L. et al. (1999) *Nucl. Acids Res.* 27:2325–2331; Allen, D. J. et al. (1997) *EMBO J.* 16:4467–4476; Bjornson K. P. et al. (2000) *Biochem.* 39:3176–3183).

Yet another aspect of the invention is the use of nuclease inhibitors that are able to block the exonuclease activity of the MMR biochemical pathway. M reporter cells are screened with nuclease inhibitor compound libraries to identify compounds capable of blocking MMR in vivo. Examples of nuclease inhibitors that are useful in blocking MMR activity include, but are not limited to analogs of N-Ethylmaleimide, an endonuclease inhibitor (Huang, Y. C., et.al. (1995) *Arch. Biochem. Biophys.* 316:485), heterodimeric adenine-chain-acridine compounds, exonulcease III inhibitors (Belmont P, et.al., *Bioorg Med Chem Lett* (2000) 10:293–295), as well as antibiotic compounds such as Heliquinomycin, which have helicase inhibitory activity (Chino, M, et.al. *J. Antibiot.* (Tokyo) (1998) 51:480–486).

Another aspect of the invention is the use of DNA polymerase inhibitors that are able to block the polymerization required for mismatch-mediated repair. MMR reporter cells are screened with DNA polymerase inhibitor compound libraries to identify those compounds capable of blocking MMR in vivo. Examples of DNA polymerase inhibitors that are useful in blocking MMR activity include, but are not limited to, analogs of actinomycin D (Martin, S. J., et.al. (1990) *J. Immunol.* 145:1859), Aphidicolin (Kuwakado, K. et.al. (1993) *Biochem. Pharmacol.* 46:1909) 1-(2'-Deoxy-2'-fluoro-beta-L-arabinofuranosyl)-5-methyluracil (L-FMAU) (Kukhanova M, et.al., *Biochem Pharmacol* (1998) 55:1181–1187), and 2',3'-dideoxyribonucleoside 5'-triphosphates (ddNTPs) (Ono, K., et.al., *Biomed Pharmacother* (1984) 38:382–389).

In yet another aspect of the invention, antisense oligonucleotides are administered to cells to disrupt at least one function of the mismatch repair process. The antisense polynucleotides hybridize to MMR polynucleotides. Both full-length and antisense polynucleotide fragments are suitable for use. "Antisense polynucleotide fragments" of the invention include, but are not limited to polynuclotides that specifically hybridize to an MMR encoding RNA (as determined by sequence comparison of nucleotides encoding the MMR to nucleotides encoding other known molecules). Identification of sequences that are substantially unique to MMR-encoding polynucleotides can be ascertained by analysis of any publicly available sequence database and/or with any commercially available sequence comparison programs. Antisense molecules may be generated by any means including, but not limited to chemical synthesis, expression in an in vitro transcription reaction, through expression in a transformed cell comprising a vector that may be transcribed to produce antisense molecules, through restriction digestion and isolation, through the polymerase chain reaction, and the like.

Antisense oligonucleotides, or fragments thereof may include the nucleotide sequences set forth in SEQ ID NOs:15, 17, 19, 21, 23, 25, 27, and 29 or sequences complementary or homologous thereto, for example. Those of skill in the art recognize that the invention may be predicted using any MMR gene. Specifically, antisense nucleic acid molecules comprise a sequence complementary to at least about 10, 15, 25, 50, 100, 250 or 500 nucleotides or an entire MMR encoding sequence. Preferably, the antisense oligonucleotides comprise a sequence complementary to about 15 consecutive nucleotides of the coding strand of the MMR encoding sequence.

In one embodiment, an antisense nucleic acid molecule is antisense to a "coding region" of the coding strand of a nucleotide sequence encoding an MMR protein. The coding strand may also include regulatory regions of the MMR sequence. The term "coding region" refers to the region of the nucleotide sequence comprising codons which are translated into amino acid residues (e.g., the protein coding region of human PMS2 corresponds to the coding region SEQ ID NO:17). In another embodiment, the antisense nucleic acid molecule is antisense to a "noncoding region" of the coding strand of a nucleotide sequence encoding an MMR protein. The term "noncoding region" refers to 5' and 3' sequences which flank the coding region that are not translated into amino acids (i.e., also referred to as 5' and 3' untranslated regions (UTR)).

Preferably, antisense oligonucleotides are directed to regulatory regions of a nucleotide sequence encoding an MMR protein, or mRNA corresponding thereto, including, but not limited to, the initiation codon, TATA box, enhancer sequences, and the like. Given the coding strand sequences provided herein, antisense nucleic acids of the invention can be designed according to the rules of Watson and Crick or Hoogsteen base pairing. The antisense nucleic acid molecule can be complementary to the entire coding region of an MMR mRNA, but more preferably is an oligonucleotide that is antisense to only a portion of the coding or noncoding region of an MMR mRNA. For example, the antisense oligonucleotide can be complementary to the region surrounding the translation start site of an MMR mRNA. An antisense oligonucleotide can be, for example, about 5, 10, 15, 20, 25, 30, 35, 40, 45 or 50 nucleotides in length.

Screening is any process whereby a chemical compound is exposed to a cell or whole organism. The process of screening can be carried out using but not limited to a whole animal, plant, insect, microbe, or by using a suspension of one or more isolated cells in culture. The cell can be any type of eukaryotic or prokaryotic cell, including, for example, cells isolated from humans or other primates, mammals or other vertebrates, invertebrates, and single celled organisms such as protozoa, yeast, or bacteria.

In general, screening will be carried out using a suspension of cells, or a single cell, but other methods can also be applied as long as a sufficient fraction of the treated cells or tissue is exposed so that isolated cells can be grown and utilized. Techniques for chemical screening are well known to those in the art. Available techniques for screening include cell-based assays, molecular assays, and whole organism-based assays. Compounds can be added to the screening assays of the invention in order to identify those agents that are capable of blocking MMR in cells.

The screening assays of the invention provide a system wherein a cell, cells or a whole organism is contacted with a candidate compound and then tested to determine whether mismatch repair has been adversely affected. The method in which MMR is analyzed may be any known method, including, but not limited to analysis of the molecular sequence of the MMR gene, and analyzing endogenous repeats in the subject's genome. Further, the invention provides a convenient assay to analyze the effects of candidate agents on reporter genes transfected into cells.

MMR-inhibitors identified by the methods of the invention can be used to generate new mutations in one or more gene(s) of interest. A gene of interest can be any gene naturally possessed by a cell line, microbe or whole organism. An advantage of using chemicals rather than recombinant technologies to block MMR are that the process is faster; there is no need to produce stable clones with a knocked out MMR gene or a clone expressing a dominant negative MMR gene allele. Another advantage is that host organisms need not be screened for integrated knock out targeting vectors or stable expression of a dominant negative MMR gene allele. Finally, once a cell, plant or animal has been exposed to the MMR-blocking compound and a new output trait is generated, the MMR process can be restored by removal of compound. Mutations can be detected by analyzing the genotype of the cell, or whole organism, for example, by examining the sequence of genomic DNA, cDNA, messenger RNA, or amino acids associated with the gene of interest. Mutations can also be detected by screening for new output traits such as hypoxanthine-guanine phosphoribosyltransferase (HPRT) revertants. A mutant polypeptide can be detected by identifying alterations in electrophoretic mobility, spectroscopic properties, or other physical or structural characteristics of a protein encoded by a mutant gene. One can also screen for altered function of the protein in situ, in isolated form, or in model systems. One can screen for alteration of any property of the cell, plant or animal associated with the function of the gene of interest.

Several advantages exist in generating genetic mutations by blocking MMR in vivo in contrast to general DNA damaging agents such as MNNG, MNU and EMS. Cells with MMR deficiency have a wide range of mutations dispersed throughout their entire genome in contrast to DNA damaging agents such as MNNG, MNU, EMS and ionizing radiation. Another advantage is that mutant cells that arise from MMR deficiency are diploid in nature and do not lose large segments of chromosomes as is the case of DNA damaging agents such as EMS, MNU, and ionizing radiation (Honma, M. et al. (1997) *Mutat. Res.* 374:89–98). This unique feature allows for subtle changes throughout a host's genome that leads to subtle genetic changes yielding genetically stable hosts with commercially important output traits.

The invention also encompasses blocking MMR in vivo and in vitro and further exposing the cells or organisms to a chemical mutagen in order to increase the incidence of genetic mutation.

The invention also encompasses withdrawing exposure to inhibitors of mismatch repair once a desired mutant genotype or phenotype is generated such that the mutations are thereafter maintained in a stable genome.

The above disclosure generally describes the present invention. A more complete understanding can be obtained by reference to the following specific examples, which are provided herein for purposes of illustration only, and are not intended to limit the scope of the invention.

EXAMPLES

Example 1

Generation of a Cell-based Screening Assay to Identify Chemicals Capable of Inactivating Mismatch Repair in vivo A hallmark of MMR deficiency is the generation of unstable microsatellite repeats in the genome of host cells (Peinado, M. A. et al. (1992) *Proc. Natl. Acad. Sci. USA* 89:10065–10069; Strand, M. et al. (1993) *Nature* 365:274–276; Parsons, R. et al. (1993) *Cell* 75:1227–1236). This phenotype is referred to as microsatellite instability (MI) (Harfe, B. D. and S. Jinks-Robertson (2000) *Ann. Rev. Genet.* 34:359–399; Modrich, P. (1994) *Science* 266:1959–1960; Peinado, M. A. et al. (1992) *Proc. Natl. Acad. Sci. USA* 89:10065–10069; Perucho, M. (1996) *Biol. Chem.* 377:675–684; Hoang, J. M. et al. (1997) *Cancer Res.* 57:300–303; Strand, M. et al. (1993) *Nature* 365:274–276). MI consists of deletions and/or insertions within repetitive mono-, di- and/or tri nucleotide repetitive sequences throughout the entire genome of a host cell. Extensive genetic analysis of eukaryotic cells have found that the only biochemical defect that is capable of producing MI is defective MMR (Harfe, B. D. and S. Jinks-Robertson (2000) *Ann. Rev. Genet.* 34:359–399; Modrich, P. (1994) *Science* 266:1959–1960; Peinado, M. A. et al. (1992) *Proc. Natl. Acad. Sci. USA* 89:10065–10069; Perucho, M. (1996) *Biol. Chem.* 377:675–684; Hoang, J. M. et al. (1997) *Cancer Res.* 57:300–303; Strand, M. et al.(1993) *Nature* 365:274–276). In light of this unique feature that defective MMR has on promoting microsatellite instability, endogenous MI is now used as a biochemical marker to survey for lack of MMR activity within host cells (Hoang, J. M. et al. (1997) *Cancer Res.* 57:300–303).

Figure 1:
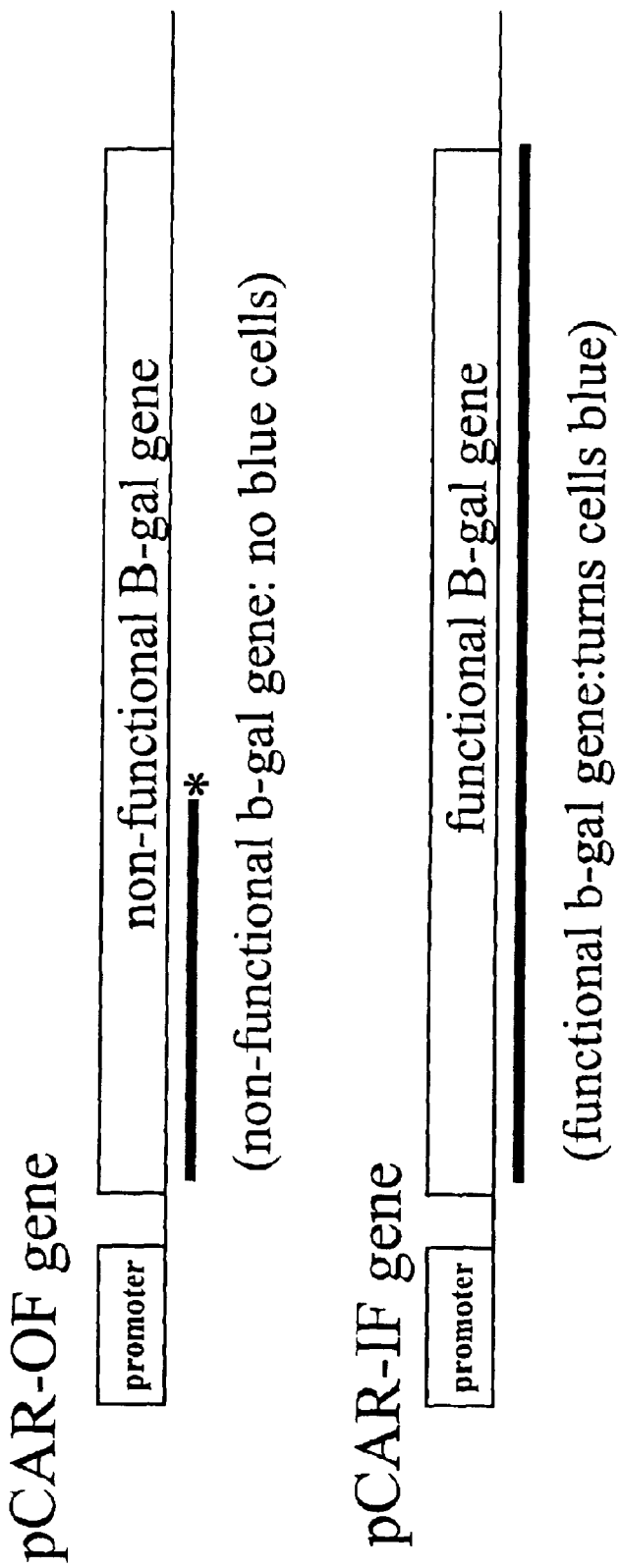
FIG. 1 shows diagrams of mismatch repair (MMR) sensitive reporter genes. Engineered genes used to measure the in vivo gene altering capability of chemical induced defective mismatch repair. In MMR defective cells, the nonfunctional b-gal gene is altered to produce a functional protein that can turn cells blue in the presence of X-gal substrate.
Figure 2:
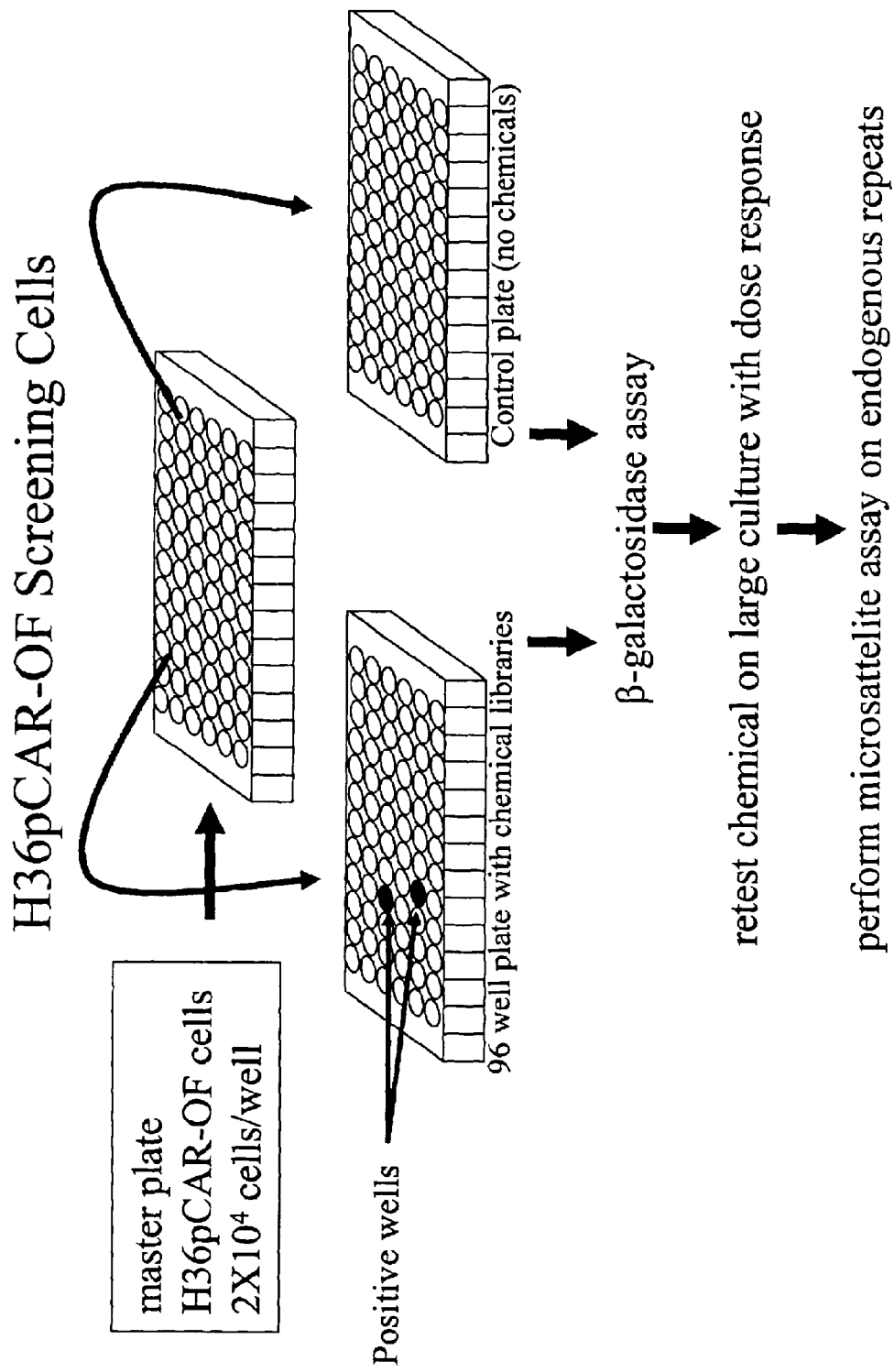
FIG. 2 shows a screening method for identifying MMR blocking chemicals. Screening method for identifying mismatch repair blocking chemicals. The assay employs the use of H36pCAR-OF cells which constitutively express the nonfunctional b-galactosidase pCAR-OF gene. Twenty thousand cells are plated in 100 mls of growth medium in a 96-well master plate. 5 mls of cells (ten thousand cells) are then replated into duplicate wells, one containing chemicals, the other control medium to account for background. Cells are grown for 14 days, lysed and measured for b-galactosidase activity using CPRG substrate buffer. Wells are measured for activity by spectrophometery at an OD of 576 nm. Chemicals producing positive activity are then retested on larger H36pCAR-OF cultures at different doses. Cultures are measured for b-galactosidase and stability of endogenous microsatellite repeats.

A method used to detect MMR deficiency in eukaryotic cells is to employ a reporter gene that has a polynucleotide repeat inserted within the coding region that disrupts its reading frame due to a frame shift. In the case where MMR is defective, the reporter gene will acquire random mutations (i.e., insertions and/or deletions) within the polynucelotide repeat yielding clones that contain a reporter with an open reading frame. This reporter gene can be of any biochemical pathway such as but not limited to $\beta$-glucoronidase, $\beta$-galactosidase, neomycin resistant gene, hygromycin resistance gene, green fluorescent protein, and the like. A schematic diagram of MMR-sensitive reporters are shown in FIG. 1, where the polynucleotide repeat can consist of mono-, di-, tri- or tetra-nucleotides. We have employed the use of a β-galactosidase MMR-sensitive reporter gene to measure for MMR activity in H36 cells, which are a murine hybridoma cell line. The reporter construct used is called pCAR-OF, which contains a hygromycin resistance (HYG) gene plus a β-galactosidase gene with a 29 bp out-of-frame poly-CA tract inserted at the 5' end of its coding region. The pCAR-OF reporter cannot generate β-galactosidase activity unless a frame-restoring mutation (i.e., insertion or deletion) arises following transfection. This line has been shown to be sensitive to inactivated MMR where using a dominant negative MMR gene allele has found this condition to result in the production of O-galactosidase (unpublished data). An example of these data using the dominant negative PMS134 allele is shown in Table 1. Briefly, H36 cells were each transfected with an expression vector containing the PMS134 allele (referred to as HB134) or empty vector and the pCAR-OF vector in duplicate reactions using the protocol below. The PMS134 gene is cloned into the pEF expression vector, which contains the elongation factor promoter upstream of the cloning site followed by a mammalian polyadenylation signal. This vector also contains the NEOr gene that allows for selection of cells in G418 to identify those retaining this plasmid. Briefly, cells were transfected with 1 μg of the PMS134 or empty vector using polyliposomes following the manufacturer's protocol (Life Technologies). Cells were then selected in 0.5 mg/ml of G418 for 10 days and G418 resistant cells were pooled together to analyze for gene expression. PMS134 positive cells, which were determined by RT-PCR and western blot (not shown) were expanded and transfected with the pCAR-OF reporter gene that contains a hygromycin (HYG) resistance-gene as reporter using the protocol described above. Cells were selected in 0.5 mg/ml G418 and 0.5 mg/ml HYG to select for cells retaining both the MMR effector and the pCAR-OF reporter plasmids. All cultures transfected with the pCAR vector resulted in a similar number of HYG/G418 resistant cells. Cultures were then expanded and tested for β-galactosidase activity in situ as well as by biochemical analysis of cell extracts. For in situ analysis, 100,000 cells were harvested and fixed in 1% gluteraldehyde, washed in phosphate buffered saline solution and incubated in 1 ml of X-gal substrate solution [0.15 M NaCl, 1 mM MgCl$_2$, 3.3 mM K$_4$Fe(CN)$_6$, 3.3 mM K$_3$Fe(CN)$_6$, 0.2% X-Gal] in 24 well plates for 2 hours at 37° C. Reactions were stopped in 500 mM sodium bicarbonate solution and transferred to microscope slides for analysis. Three fields of 200 cells each were counted for blue (β-galactosidase positive cells) or white (β-galactosidase negative cells) to assess for MMR inactivation. Table 1 shows the results from these studies. While no β-galactosidase positive cells were observed in H36 empty vector cells and 10% of the cells per field were β-galactosidase positive in HB134 cultures.

Table 1. β-galactosidase expression of H36 empty vector and HB134 cells transfected with pCAR-OF reporter vectors. Cells were transfected with the pCAR-OF reporter plasmid. Transfected cells were selected in HYG and G418, expanded and stained with X-gal solution to measure for β-galactosidase activity (blue colored cells). 3 fields of 200 cells each were analyzed by microscopy. The results below represent the mean +/- standard deviation of these experiments.

TABLE 1

| CELL LINE | # BLUE CELLS |
| --- | --- |
| H36 empty vector | 0 +/- 0 |
| HB134 | 20 +/- 3 |

Cultures can be further analyzed by biochemical assays using cell extracts to measure β-galactosidase activity as previously described (Nicolaides, N. C. et al. (1998) *Mol. Cell. Biol.* 18:1635–1641).

The data described in Table 1 show that by inhibiting the MMR activity of an MMR proficient cell host can result in MI and the altering of microsatellites in the pCAR-OF vector results in cells that produce functional β-galactosidase enzyme. The use of the H36pCAR-OF cell line can now be used to screen for chemicals that are able to block MMR of the H36 cell line.

Example 2

Screening Assays for Identifying Chemical Blockers of MMR

A method for screening chemical libraries is provided in this example using the H36pCAR-OF cell line described in Example 1. This cell line is a hardy, stable line that can be formatted into 96-well microtiter plates for automated screening for chemicals that specifically block MMR. An overview of the screening process is given in FIG. 2, however, the process is not limited to the specifications within this example. Briefly, 10,000 cells in a total volume of 0.1 ml of growth medium (RPMI1640 plus 10% fetal bovine serum) are added to 96-well microtiter plates containing any variety of chemical compounds. Cells are grown for 14–17 days at 37° C. in 5% CO$_2$. Cells are then lysed in the growth medium with 50 uls of lysis buffer containing 0.1 M Tris buffer (pH 8.0), 0.1% Triton X-100, 45 mM 2-mercaptoethanol, 1 mM MgCl$_2$, 0.1 M NaPO$_4$ and 0.6 mg/ml Chlorophenol-red-β-D-galactopyranoside (CPRG, Roche). Reactions are incubated for 1 hour, terminated by the addition of 50 μls of 0.5 M Na$_2$CO$_3$, and analyzed by spectrophotometry at 576 nm.

Experimental wells are compared to untreated or vehicle treated wells to identify those with increased β-galactosidase activity. Compounds producing MMR blocking activity are then further analyzed using different cell lines containing the pCAR-OF plasmid to measure the ability to block MMR as determined by MI in MMR proficient hosts by analyzing endogenous microsatellites for instability using assays described below.

Example 3

Defining MMR Blocking Chemicals

The identification of chemical inhibitors of MMR can be difficult in determining those that are standard mutagens from those that induce genomic instability via the blockade of MMR. This Example teaches of a method for determining blockers of MMR from more general mutagens. Once a compound has been identified in the assay described above, one can determine if the compound is a general mutagen or a speific MMR blocker by monitoring mutation rates in MMR proficient cells and a controlled subclone that is MMR defective. One feature of MMR deficiency is the increased resistance to toxicity of DNA alkylating agents that allows for enhanced rates of mutations upon mutagen exposure (Liu, L., et.al. *Cancer Res* (1996) 56:5375–5379). This unique feature allows for the use of a MMR proficient cell and a controlled line to measure for enhanced activity of a chemical compound to induce mutations in MMR proficient vs MMR deficient lines. If the compound is a true inhibitor of MMR then genetic mutations should occur in MMR proficient cells while no "enhanced" mutation rate will be found in already MMR defective cells. Using these criteria chemicals such as ICR191, which induces frameshift mutations in mammalian cells would not be considered a MMR blocking compound because of its ability to produce enhanced mutation rates in already MMR defective cell lines (Chen, W. D., et.al. *J Natl Cancer Inst.* (2000) 92:480–485). These screening lines include the but are not limited those in which a dominant negative MMR gene has been introduced such as that described in EXAMPLE 1 or those in which naturally MMR deficient cells such as HCT116 has been cured by introduction of a complementing MMR gene as described (Chen, W. D., et.al. *J Natl Cancer Inst.* (2000) 92:480–485).

Example 4

Identification of Chemical Inhibitors of MMR in vivo

MMR is a conserved post replicative DNA repair mechanism that repairs point mutations and insertion/deletions in repetitive sequences after cell division. The MMR requires an ATPase activity for initiation complex recognition and DNA translocation. In vitro assays have shown that the use of nonhydrolyzable forms of ATP such as AMP-PNP and ATP[gamma]S block the MMR activity (Galio, L. et al. (1999) *Nucl. Acids Res.* 27:2325–2331; Allen, D. J. et al. (1997) *EMBO J.* 16:4467–4476; Bjornson K. P. et al. (2000) *Biochem.* 39:3176–3183).

Figure 3:
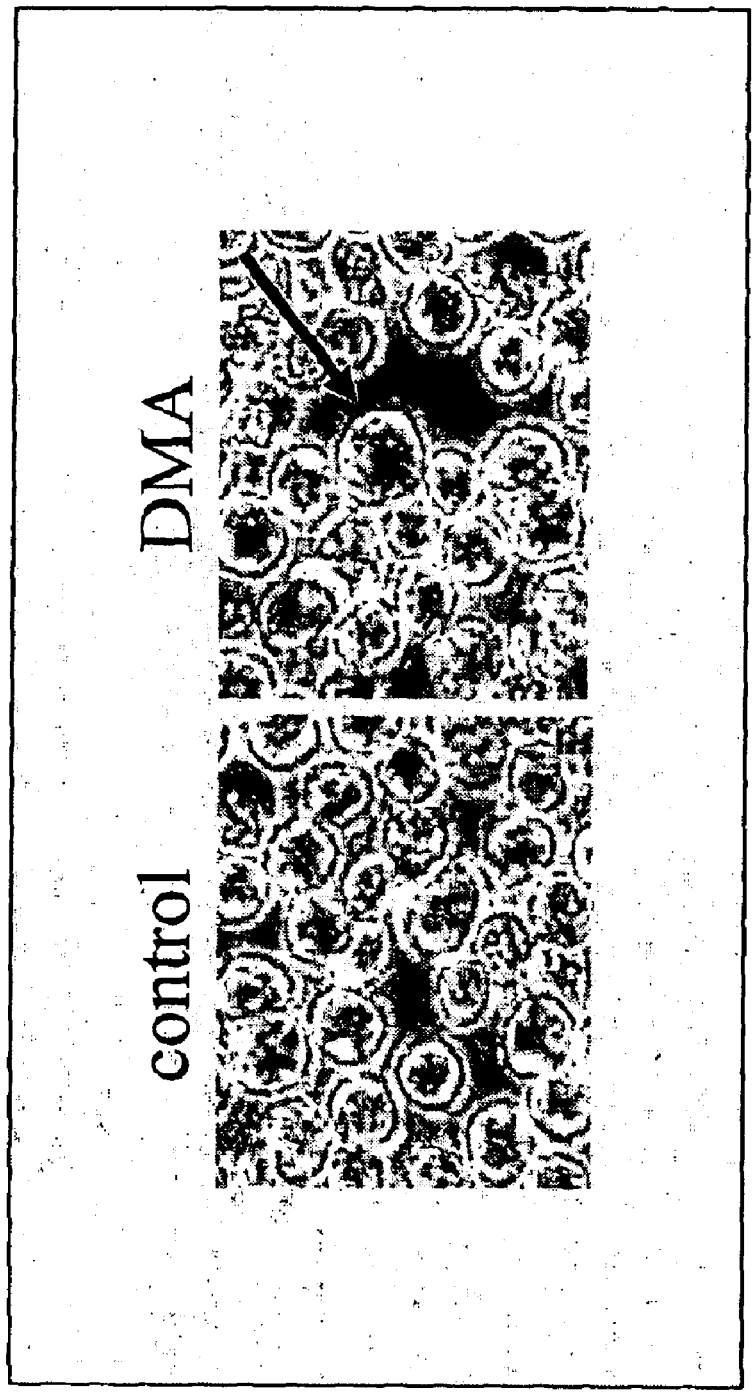
FIG. 3 shows identification of a small chemical that blocks MMR and genetically alters the pCAR-OF vector in vivo. DMA produces b-gal positive H36pCAR-OF cells. H36pCAR-OF cells grown in the presence of DMA generated functional b-gal producing reporter cells due to alteration of the polyA repeat contained within the N-terminus of the construct. The Arrow indicates b-gal positive cells. Approximately 3% of cells were positive for b-gal. Shifting of endogenous microsatellites in human cells induced by DMA in human 293 cells.

The use of chemicals to inhibit endogenous MMR in vivo has not been distinguished in the public domain. In an attempt to identify chemicals that can inhibit MMR in vivo, we used our H36pCAR-OF screening assay to screen for chemicals that are able to cause microsatellite instability and restoration of β-galactosidase activity from the pCAR-OF vector, an effect that can only be caused due to MMR deficiency. In our screening assays we used a variety of classes of compounds ranging from steroids such as pontasterone to potent alkylating agents such as EMS, to kinase and other enzyme inhibitors. Screens identified one class of chemicals that were capable of generating β-galactosidase positive cells. These molecules were derived from the anthracene class. An example of one such anthracene derivative for the purposes of this application is a molecule called 9,10-dimethylanthracene, referred to from here on as DMA. FIG. 3 shows the effect of DMA in shifting the pCAR-OF reporter plasmid. In contrast, general DNA alkylating agents such as EMS or MNNG did not result in MI and/or the shifting of the polynulceotide tract in the pCAR-OF reporter.

The most likely explanation for the differences in β-galactosidase activity was that the DMA compound disturbed MMR activity, resulting in a higher frequency of mutation within the pCAR-OF reporter and re-establishing the ORF. To directly test the hypothesis that MMR was altered, we employ a biochemical assay for MMR with the individual clones as described by Nicolaides et al., 1997 (Nicolaides, N. C. et al. (1998) *Mol. Cell. Biol.* 18:1635–1641). Nuclear extracts are prepared from the clones and incubated with heteroduplex substrates containing either a /CA\ insertion-deletion or a G/T mismatch under conditions described previously. The /CA\ and G/T heteroduplexes are used to test repair from the 3' and 5' directions, respectively as described (Nicolaides, N. C. et al. (1998) *Mol. Cell. Biol.* 18:1635–1641).

Biochemical Assays for Mismatch Repair.
Enzymatic Repair Assays:

MMR activity in nuclear extracts is performed as described, using 24 fmol of substrate (Nicolaides, N. C. et al. (1998) *Mol. Cell. Biol.* 18:1635–1641). Complementation assays are done by adding ~100 ng of purified MutLa or MutSa components to 100 µg of nuclear extract, adjusting the final KCl concentration to 100 mM (Nicolaides, N. C. et al. (1998) *Mol. Cell. Biol.* 18:1635–1641). The substrates used in these experiments contain a strand break 181 nucleotides 5' or 125 nucleotides 3' to the mismatch.

Biochemical Activity Assays:

To demonstrate the direct effect to small molecules on MMR proteins, molecular assays such as mismatch binding and MMR complex formation are performed in the presence or absence of drug. Briefly, MMR gene cDNAs are PCR amplified using primers encompassing the entire coding regions of the known MMR proteins MSH2 (SEQ ID NO:20), GTBP (SEQ ID NO:26), MLH1 (SEQ ID NO:22), human PMS2 (SEQ ID NO:16), mouse PMS2 (SEQ ID NO:14), PMS1 (SEQ ID NO:18), and MHS3 (SEQ ID NO:28) from any species with a sense primer containing a T7 promoter and a Kozak translation signal as previously described (Nicolaides, N. C. et al. (1998) *Mol. Cell. Biol.* 18:1635–1641). The coding regions of known MMR proteins include the sequences shown in Table 3 for mouse PMS2 (SEQ ID NO:15), human PMS2 (SEQ ID NO: 17), human PMS1 (SEQ ID NO: 19), human MSH2 (SEQ ID NO:21), human MLH1 (SEQ ID NO:23), and human MSH3 (SEQ ID NO:29). Products are transcribed and translated using the TNT system (Promega). An example of PCR primers and in vitro transcription-translation reactions are listed below.

In vitro Transcription-translation:

Linear DNA fragments containing hPMS2 (SEQ ID NO:17) and hMLH1 (SEQ ID NO:23) cDNA sequences were prepared by PCR, incorporating sequences for in vitro transcription and translation in the sense primer. A full-length hMLH1 fragment was prepared using the sense primer 5'-ggatcctaatacgactcactatagggagaccaccatgtcgttcgtggcaggg-3' (SEQ ID NO:1)(codons 1–6) and the antisense primer 5'-taagtcttaagtgctaccaac-3' (SEQ ID NO:2)(located in the 3' untranslated region, nt 2411–2433), using a wild-type hMLH1 cDNA clone as template. A full-length hPMS2 fragment was prepared with the sense primer 5'-ggatcctaatacgactcactatagggagaccaccatggaacaattgcctgcgg-3' (SEQ ID NO:3)(codons 1–6) and the antisense primer 5'-aggttagtgaagactctgtc-3' (SEQ ID NO:4)(located in 3' untranslated region, nt 2670–2690) using a cloned hPMS2 cDNA as template. These fragments were used to produce proteins via the coupled transcription-translation system (Promega). The reactions were supplemented with $^{35}$S-labelled methionine or unlabelled methionine. Lower molecular weight bands are presumed to be degradation products and/or polypeptides translated from alternative internal methionines.

To study the effects of MMR inhibitors, assays are used to measure the formation of MLH1 and PMS2 with or without compound using polypeptides produced in the TNT System (Promega) followed by immunoprecipitation (IP). To facilitate the IP, tags may be placed at the C-terminus of the PMS2 protein to use for antibody binding or antibodies directed to the MMR protein itself can be used for IP.

Immunoprecipitations:

Immunoprecipitations are performed on in vitro translated proteins by mixing the translation reactions with 1 μg of the MLH1 specific monoclonal antibody (mAB) MLH14 (Oncogene Science, Inc.), a polyclonal antibody generated to codons 2–20 of hPMS2 described above, or a polyclonal antibody generated to codons 843–862 of hPMS2 (Santa Cruz Biotechnology, Inc.) in 400 μl of EBC buffer (50 mM Tris, pH 7.5, 0.1 M NaCl, 0.5% NP40). After incubation for 1 hr at 4° C., protein A sepharose (Sigma) is added to a final concentration of 10% and reactions are incubated at 4° C. for 1 hour. Proteins bound to protein A are washed five times in EBC and separated by electrophoresis on 4–20% Trisglycine gels, which are then dried and autoradiographed.

Compounds that block heterodimerization of mutS or mutL proteins can now be identified using this assay.

Example 5

Use of Chemical MMR Inhibitors Yields Microsatellite Instability in Human Cells

In order to demonstrate the global ability of a chemical inhibitor of MMR in host cells and organisms, we treated human HEK293 cells (referred to as 293 cells) with DMA and measured for microsatellite instability of endogenous loci using the BAT26 diagnostic marker (Hoang J. M. et al. (1997) *Cancer Res.* 57:300–303). Briefly, $10^5$ cells were grown in control medium or 250 μM DMA, a concentration that is found to be non-toxic, for 14 to 17 days. Cells are then harvested and genomic DNA isolated using the salting out method (Nicolaides, N. C. et al. (1991) *Mol. Cell. Biol.* 11:6166–6176.).

Various amounts of test DNAs from HCT116 (a human colon epithelial cell line) and 293 were first used to determine the sensitivity of our microsatellite test. The BAT26 alleles are known to be heterogeneous between these two cell lines and the products migrate at different molecular weights (Nicolaides personal observation). DNAs were diluted by limiting dilution to determine the level of sensitivity of the assay. DNAs were PCR amplified using the BAT26F: 5'-tgactacttttgacttcagcc-3' (SEQ ID NO:43) and the BAT26R: 5'-aaccattcaacatttttaaccc-3' (SEQ ID NO:44) primers in buffers as described (Nicolaides, N. C. et al. (1995) *Genomics* 30:195–206). Briefly 1 pg to 100 ngs of DNA were amplified using the following conditions: 94° C. for 30 sec, 58° C. for 30 sec, 72° C. for 30 sec for 30 cycles. PCR reactions were electrophoresed on 12% polyacrylamide TBE gels (Novex) or 4% agarose gels and stained with ethidium bromide. These studies found that 0.1 ng of genomic DNA was the limit of detection using our conditions.

To measure for microsatellite stability in 293 cells grown with or without DMA, 0.1 ngs of DNA from DMA-treated or control 293 cells were amplified using the reaction conditions above. Forty individual reactions were carried out for each sample to measure for minor alleles. FIG. 4A shows a typical result from these studies whereby BAT26 alleles were amplified from DMA-treated and untreated cells and analyzed on 12% PAGE gels (Novex). Alleles from DMA-treated cells showed the presence of an altered allele (asterisk) that migrated differently from the wild type allele. No altered alleles were found in the MMR-proficient control cells as expected since MI only occurs in MMR defective cell hosts. To confirm these data, PCRs were repeated using isolated BAT26 products. Primers and conditions were the same as described above except that reactions were amplified for 20 cycles. PCR products were gel-purified and cloned into T-tailed vectors (In Vitrogen) as suggested by the manufacturer. Recombinant clones from DMA-treated and control cells were screened by PCR again using the BAT26 primers. Fifty bacterial colonies were analyzed for BAT26 structure by directly adding an aliquot of live bacteria to the PCR mix. PCR reactions were carried out as described above, and products were electrophoresed on 4% agarose gels and stained with ethidium bromide. As shown in FIG. 4B, microsatellites from DMA-treated cells had alterations (asterisks) that made the marker length larger or smaller than the wild type allele found in control cells.

To confirm that these differences in molecular weight were due to shifts within the polynucleotide repeat, a hallmark of defective MMR, five clones from each sample were sequenced using an ABI automated sequencer with an M13-R primer located in the T-tail vector backbone. Sequence analysis revealed that the control cell clone used in our studies was homozygous for the BAT26 allele with a 26nt polyA repeat. Cells treated with DMA found multiple alleles ranging from the wild-type with 26 polyA repeat to shorter alleles (24 polyA repeat) and larger alleles (28 polyA repeat) (FIG. 5).

These data corroborate the H36pCAR data in Example 1 and FIG. 3 and demonstrates the ability to block MMR with a chemical in a range of hosts.

Example 6

Chemical Inhibitors of MMR Generate DNA Hypermutability in Plants and New Phenotypes To determine if chemical inhibitors of MMR work across a diverse array of organisms, we explored the activity of DMA on *Arabidopsis thaliana* (AT), a member of the mustard plant family, as a plant model system to study the effects of DMA on generating MMR deficiency, genome alterations, and new output traits.

Briefly, AT seeds were sterilized with straight commercial bleach and 100 seeds were plated in 100 mm Murashige and Skoog (MS) phytagar (Life Technology) plates with increasing amounts of DMA (ranging from 100 μm to 50 mM). A similar amount of seeds were plated on MS phytagar only or in MS phytagar with increasing amounts of EMS (100 μM to 50 mM), a mutagen commonly used to mutate AT seeds (McCallum, C. M. et al. (2000) *Nat. Biotechnol.* 18:455–457). Plates were grown in a temperature-controlled, fluorescent-lighted humidifier (Percival Growth Chamber) for 10 days. After 10 days, seeds were counted to determine toxicity levels for each compound. Table 2 shows the number of healthy cells/treatment as determined by root formation and shoot formation. Plantlets that were identical to untreated seeds were scored healthy. Seeds with stunted root or shoot formation were scored intermediate (inter). Non-germinated seeds were scored dead.

TABLE 2

Toxicity curve of DMA and EMS on *Arabidopsis* (per 100 cells)

|  | 0 | 0.1 | 0.5 | 1.0 | 2.5 | 5.0 | 10 | 12.5 | 25 | 50 |
|---|---|---|---|---|---|---|---|---|---|---|
| DMA |  |  |  |  |  |  |  |  |  |  |
| Healthy | 100 | 94 | 99 | 99 | 80 | 85 | 65 | 0 | 0 | 0 |
| Inter | 0 | 0 | 0 | 0 | 20 | 15 | 32 | 85 | 100 | 0 |
| Dead | 0 | 0 | 0 | 0 | 0 | 0 | 0 | 0 | 0 | 100 |
| EMS |  |  |  |  |  |  |  |  |  |  |
| Healthy | 99 | 100 | 45 | 25 | 0 | 0 | 0 | 0 | 0 | 0 |
| Inter | 0 | 0 | 54 | 75 | 0 | 0 | 0 | 0 | 0 | 0 |
| Dead | 0 | 0 | 0 | 0 | 100 | 100 | 100 | 100 | 100 | 87 |

The data in Table 2 show that DMA toxicity occurs at 10 mM of continuous culture, while toxicity occurs at 250 µM for EMS. Next, 50 seeds were plated in two 150 mm dishes containing 2 mM DMA, 250 µM EMS or no drug. Seeds were grown for 10 days and then 10 plants from each plate were transferred to soil. All plants appeared to be similar in color and height. Plants were grown at room temperature with daily cycles of 18 hr light and 6 hr dark. After 45 days seeds are harvested from siliques and stored in a desiccator at 4° C. for 72 hours. Seeds are then sterilized and 100 seeds from each plant is sown directly into water-saturated soil and grown at room temperature with daily cycles of 18 hr light and 6 hr dark. At day 10 phenotypically distinct plants were found in 7 out of 118 DMA treated while no phenotypic difference was observed in 150 EMS-treated or 150 control plants. These 7 altered plants were light green in color and appeared to grow slower. FIG. 6 shows a typical difference between the DMA altered plant and controls. DMA-exposed plants produced offspring that were yellow in appearance in contrast to dark green, which is always found in wild-type plants. In addition, the yellow plants were also shorter. After 30 days, most wild-type plants produced flowers and siliques, while the 7 mutants just began flowering. After 45 days, control plants were harvested while mutant plants were harvested 10 to 15 days later. No such effects were observed in 150 plantlets from EMS treated plants.

The effect of DMA on MMR was confirmed by monitoring the structure of endogenous polynucleotide repeat markers within the plant genome. DNA was extracted using the DNAzol method following the manufacturer's protocol (Life Technology). Briefly, two leaves were harvested from DMA, EMS or untreated plants and DNA was extracted. DNAs were quantified by optical density using a BioRad Spectrophotometer. In *Arabidopsis*, a series of poly-A $(A)_n$, $(CA)_n$ and $(GA)_n$ markers were found as a result of EMBL and GenBank database searches of DNA sequence data generated as a result of the *Arabidopsis* genome-sequencing project. Two markers that are naturally occurring, ATHACS and Nga128 are used to monitor microsatellite stability using primers described (Bell, C. J. and J. R. Ecker (1994) *Genomics* 19:137–144). ATHACS has a stretch of thirty-six adenine repeats $(A)_{36}$ whereas Nga128 is characterized by a di-nucleotide AG repeat that is repeated nineteen times $(AG)_{19}$ while the Nga280 marker contains a polyAG repeat marker with 15 dinucleotides. DMA-mediated alterations of these markers are measured by a PCR assay.

Briefly, the genomic DNA is amplified with specific primers in PCR reaction buffers described above using 1–10 ng plant genomic DNA. Primers for each marker are listed below:

```
nga280:
  nga280-F:  5'-CTGATCTCACGGACAAT    (SEQ ID NO:5)
                              AGTGC-3'
  nga280-R:  5'-GGCTCCATAAAAAGTGC    (SEQ ID NO:6)
                                ACC-3' nga128:
  nga128-F:  5'-GGTCTGTTGATGTCGTA    (SEQ ID NO:7)
                              AGTCG-3'
  nga128-R:  5'-ATCTTGAAACCTTTAGG    (SEQ ID NO:8)
                              GAGGG-3'

ATHACS:
  ATHACS-F:  5'-AGAAGTTTAGACAGGTA    (SEQ ID NO:9)
                                  C-3'
  ATHACS-R:  5'-AAATGTGCAATTGCCTT    (SEQ ID NO:10)
                                  C-3'
```

Cycling conditions are 94° C. for 15 seconds, 55° C. for 15 seconds and 72° C. for 30 seconds, conditions that have been demonstrated to efficiently amplify these two markers (personal observation, Morphotek). PCR products are analyzed on 3.5% metaphor agarose gel in Tris-Acetate-EDTA buffer following staining with ethidium bromide.

Another method used to demonstrate that biochemical activity of a plant host's MMR is through the use of reporter genes disrupted by a polynucleotide repeat, similar to that described in Example 1 and FIG. 1. Due to the high endogenous β-galactosidase background, we engineered a plant compatible MMR-sensitive reporter gene consisting of the β-glucoronidase (GUS) gene with a mononucleotide repeat that was inserted just downstream of the initiation codon. Two reporter constructs were generated. pGUS-OF, contained a 20 base adenine repeat inserted just downstream of the initiating methionine that resulted in a frameshift, therefore producing a nonfunctional enzyme. The second, pGUS-IF, contained a 19 base adenine repeat that retained an open reading frame and served as a control for β-glucoronidase activity. Both constructs were generated by PCR using the pBI-121 vector (Life Technologies) as template. The antisense primer was directed to the 3' end of the Nopaline Synthase (NOS) polytermination sequence contained within the pBI-121 plasmid and contained a unique EcoRI restriction site to facilitate cloning of the vector into the pBI-121 binary vector backbone. The sense primers contained a unique BamHI restriction site to facilitate cloning of the chimeric GUS reporter gene into the pBI-121 binary vector backbone. The primers used to generate each reporter are:

```
                                                     (SEQ ID NO:11)
1. sense primer for pGUS-IF (uidA-ATG-polyA-IF):
5'-CCC GGA TCC ATG TTA AAA AAA AAA AAA AAA CGT
                                  CCT GTA GAA ACC-3'

(SEQ ID NO:12)
2. sense primer for pGUS-OF (uidA-ATG-polyA-OF):
5'-CCC GGA TCC ATG TTA AAA AAA AAA AAA AAA ACG
                                  TCC TGT AGA AAC C-3'

(SEQ ID NO:13)
3. antisense primer (Nos-term):
5'-CCC GAA TTC CCC GAT CTA GTA ACA TAG ATG-3'
```

PCR amplifications were carried out using reaction buffers described above. Reactions were performed using 1 ng of pBI-121 vector as template (Life Technologies) and the appropriate corresponding primers. Amplifications were carried at 94° C. for 30 seconds, 54° C. for 60 seconds and 72° C. for 60 seconds for 25 cycles. PCR products of the expected molecular weight was gel purified, cloned into T-tailed vectors (In Vitrogen), and sequenced to ensure authentic sequence using the following primers: CaMV-FORW. [=5'-gat atc tcc act gac gta ag-3'] (SEQ ID NO:30) for sequencing from the CaMV promoter into the 5' end of GUS cDNAs; NOSpA-42F [=5'-tgt tgc cgg tct tgc gat g-3'] (SEQ ID NO:31) for sequencing of the NOS terminator; NOSpA-Cend-R [=5'-ccc gat cta gta aca tag atg-3'] (SEQ ID NO:32) for sequencing from the NOS terminator into the 3' end of the GUS cDNAs; GUS-63F [=5'-cag tct gga tcg cga aaa ctg-3'] (SEQ ID NO:33), GUS-441F [=5'-ggt gat tac cga cga aaa cg-3'] (SEQ ID NO:34), GUS-825F [=5'-agt gaa ggg cga aca gtt cc-3'] (SEQ ID NO:35), GUS-1224F [=5'-gag tat tgc caa cga acc-3'] (SEQ ID NO:36), GUS-1596F [=5'-gta tca ccg cgt ctt tga tc-3'] (SEQ ID NO:37), GUS-265R [=5'-cga aac gca gca cga tac g-3'] (SEQ ID NO:38), GUS-646R [=5'-gtt caa cgc tga cat cac c-3'] (SEQ ID NO:39), GUS-1033R [=5'-cat gtt cat ctg ccc agt cg-3'] (SEQ ID NO:40), GUS-1425R [=5'-gct ttg gac ata cca tcc-3'] (SEQ ID NO:41), and GUS-1783R [=5'-cac cga agt tca tgc cag-3'] (SEQ ID NO:42) for the sequence of the full length GUS cDNAs. No mutation were found in either the OF or IF version of the GUS cDNA, and the expected frames for both cDNAs were also confirmed. pCR-IF-GUS and pCR-OF-GUS plasmids were subsequently digested with the BamH I and EcoR I restriction endonucleases, to generate DNA fragments containing the GUS cDNA along with the NOS terminator. These fragments were ligated into the BamH I and the EcoR I sites of the pBI-121 plasmid, which was prepared for cloning by cutting it with the same enzymes to release the wild type GUS cDNA. The resulting constructs (pBI-IF-GUS and pBI-OF-GUS) were subsequently digested with Hind III and EcoR I to release the DNA fragments encompassing the CaMV promoter, the IF or OF GUS cDNA, and the NOS terminator. Finally, these fragments were ligated into the correspondent restriction sites present in the pGPTV-HPT binary vector (ATCC) to obtain the pCMV-IF-GUS-HPT and pCMV-OF-GUS-HPT binary vectors.

The resulting vectors, CMV-OF-GUS-HPT and CMV-IF-GUS-HPT now contain the CaMV35S promoter from the Cauliflower Mosaic 35 S Virus driving the GUS gene followed by a NOS terminator and polyadenylation signal (FIG. 7). In addition, this vector also contains a hygromycin resistance gene as a selectable marker that is used to select for plants containing this reporter.

Generation of GUS Reporter-expressing *Arabidopsis thaliana* Transgenic Plants.

*Agrobacterium tumefaciens* bacteria are used to shuttle binary expression vectors into plants. To generate β-glucoronidase-expressing *Arabidopsis thaliana* (*A. thaliana*) plants, *Agrobacterium tumefaciens* cells (strain GV3101) were electroporated with the CMV-OF-GUS-HPT or the CMV-IF-GUS-HPT binary vector using methods known by those skilled in the art. Briefly, one-month old *A. thaliana* (ecotype Columbia) plants were infected by immersion in a solution containing 5% sucrose, 0.05% silwet and binary vector-transformed *Agrobacteria* cells for 10 seconds. These plants were then grown at 25° C. under a 16 hour day and 8 hour dark photoperiod. After 4 weeks, seeds (referred to as T1) were harvested and dried for 5 days. Thirty thousands seeds from ten CMV-OF-GUS-HPT or CMV-IF-GUS-HPT-transformed plants were sown in solid Murashige and Skoog (MS) media plates in the presence of 20 µg/ml of hygromycin (HYG). Three hundred plants were found to be HYG resistant and represented GUS expressing plants. These plants along with 300 control plants were grown in MS media for two weeks and then transferred to soil. Plants were grown for an additional four weeks under standard conditions at which time T2 seeds were harvested.

To confirm the integration and stability of the GUS vector in the plant genome, gene segregation and PCR analyses were conducted. Commonly, three out of four T1 plants transformed by *Agrobacteria* technology are expected to carry the vector inserted within a single locus and are therefore considered heterozygous for the integrated gene. Approximately 75% of the seeds (T2) generated from most of the T1 plants were found HYG-resistant and this in accordance with the expected 1:2:1 ratio of null (no GUS containing plants), heterozygous, and homozygous plants, respectively, in self-pollinating conditions. To confirm that these plants contained the GUS expression vector, genomic DNA was isolated from leaves of T1 plants using the DNAzol-mediated technique as described above. One ng of genomic DNA was analyzed by polymerase chain reaction (PCR) to confirm the presence of the GUS vector. PCR was carried out for 25 cycles with the following parameters: 95° C. for 30 seconds; 54° C. for 1 minute; and 72° C. for 2 minutes using primers listed above. Positive reactions were observed in DNA from CMV-OF-GUS-HPT and CMV-IF-GUS-HPT-transformed plants and not from control (uninfected) plants.

In order to assess the expression of the GUS in T1 plants, leaf tissue was collected from T1 plants, homogenized in liquid nitrogen using glass pestles, and suspended in RLT lysing buffer (Qiagen, RNeasy plant RNA extraction kit). Five micrograms of total RNA was purified according to the manufacturer's suggested protocol and then loaded onto a 1.2% agarose gel (1× MOPS buffer, 3% formaldehyde), size-fractionated by electrophoresis, and transferred onto N-Hybond+ membrane (Amersham). Each membrane was incubated at 55° C. in 10 ml of hybridization solution (North2South labeling kit, Pierce) containing 100 ng of GUS, tubulin, or HYG probes, which were generated by PCR amplification, according to the manufacturer's directions. Membranes were washed three times in 2×SSC, 0.1% SDS at 55° C., and three times in 2×SSC at ambient temperature. Detection was carried out using enhanced chemiluminescence (ECL). GUS message was detected in three out of ten analyzed transgenic lines, while no signal was found in the control plants. Collectively these studies demonstrated the generation of GUS expressing transgenic *A. thaliana* plants.

To determine the status of MMR activity in host plants, one can measure for the production of functional β-glucoronidase by staining plant leaves or roots in situ for β-glu activity. Briefly, plant tissue is washed twice with water and fixed in 4 mls of 0.02% glutaraldehyde for 15 minutes. Next, tissue is rinsed with water and incubated in X-glu solution [0.1M $NaPO_4$, 2.5 mM $K_3Fe(CN)_6$, 2.5 mM $K_4Fe(CN)_6$, 1.5 mM $MgCl_2$, and 1 mg/ml X-GLU (5 bromo-4-chloro-3-indoyl-β-D-glucuronide sodium salt) (Gold Biotechnology)] for 6 hours at 37° C. Tissues are then washed twice in phosphate buffered saline (PBS) solution, once in 70% ethanol and incubated for 4 hours in methanol:acetone (3:1) for 8 hours to remove chlorophyll. Tissues are then washed twice in PBS and stored in PBS with 50% glycerol. Plant tissue with functional GUS activity will stain blue.

The presence of GUS activity in CMV-IF-GUS-HPT plants indicates that the in-frame N-terminus insertion of the poly A repeat does not disrupt the GUS protein function. The CMV-OF-GUS-HPT plants treated with DMA, EMS or untreated are tested to determine if these plants produce GUS activity. The presence of GUS activity in DMA treated plants indicates that the polyA repeat was altered, therefore, resulting in a frame-restoring mutation. Agents such as EMS, which are known to damage DNA by alkylation cannot affect the stability of a polynucleotide repeat. This data indicates that plants are defective for MMR, the only process known to be responsible for MI.

These data demonstrate the utility and power of using a chemical inhibitor of MMR to generate a high degree of genetic alteration that is not capable by means of standard DNA damaging drugs. Moreover, this application teaches of the use of reporter genes such as GUS-OF in plants to monitor for the MMR activity of a plant host.

Example 7

Use of Chemical MMR Inhibitors Yields Microsatellite Instability in Microbes To demonstrate the ability of chemical inhibitors to block MMR in a wide range of hosts, we employed the use of *Pichia* yeast containing a pGUS-OF reporter system similar to that described in Example 5. Briefly, the GUS-OF and GUS-IF gene, which contains a polyA repeat at the N-terminus of the protein was subcloned from the pCR-IF-GUS and pCR-OF-GUS plasmids into the EcoRI site of the pGP vector, which is a consitutively expressed yeast vector containing a zeocin resistance gene as selectable marker. pGP-GUS-IF and pGP-GUS-OF vectors were electroporated into competent *Pichia* cells using standard methods known by those skilled in the art. Cells were plated on YPD agar (10 g/L yeast extract; 20 g/L peptone; 2% glucose; 1.5% bactoagar) plates containing 100 µg/ml zeocin. Recombinant yeast are then analyzed for GUS expression/function by replica plating on YPD agar plates containing 100 µg/ml zeocin plus 1 mg/ml X-glu (5-bromo-4-chloro-3-indoyl-beta-D-glucuronide sodium salt) and grown at 30° C. for 16 hours. On hundred percent of yeast expressing GUS-IF were found to turn blue in the presence of the X-glu substrate while none of the control yeast turned blue. None of the yeast containing the GUS-OF turned blue in the presence of the X-glu substrate under normal growth conditions.

To demonstrate the ability of chemicals to block MMR in yeast, GUS-OF and control cells were incubated with 300 µM DMA, EMS, or no chemical for 48 hours. After incubation, yeast were plated on YPD-ZEO-X-GLU plates and grown at 30° C. for 16 hours. After incubation, a subset of yeast expressing GUS-OF contain blue subclones, while none are seen in EMS or control cells. These data demonstrate the ability of chemicals to block MMR of microbes in vivo to produce subclones with new output traits.

Example 8

Classes of other Chemicals Capable of Blocking MMR in vivo

The discovery of anthracene compounds presents a new method for blocking MMR activity of host organisms in vivo. While 9,10-dimethylanthracene (DMA) was found to block MMR in cell hosts, other analogs with a similar chemical composition from this class are also claimed in this invention. These include anthracene and related analogs such as 9,10-diphenylanthracene and 9,10-di-M-tolylanthracene. Myers et al. ((1988) *Biochem. Biophys. Res. Commun.* 151:1441–1445) disclosed that at high concentrations, DMA acts as a potent weak mutagen, while metabolized forms of DMA are the "active" ingredients in promoting mutation. This finding suggests that metabolites of anthracene-based compounds may also act as active inhibitors of MMR in vivo. For instance, metabolism of anthracene and 9,10-dimethylanthracene by *Micrococcus* sp., *Pseudomonas* sp. and *Bacillus macerans* microbes have found a number of anthracene and 9,10-dimethylanthracene metabolites are formed. These include anthracene and 9,10-dimethylanthracene cis-dihydrodiols, hydroxy-methyl-derivatives and various phenolic compounds. Bacteria metabolize hydrocarbons using the dioxygenase enzyme system, which differs from the mammalian cytochrome P-450 monoxygenase. These findings suggest the use of bacteria for biotransforming anthracene and DMA for additional MMR blocking compounds (Traczewska, T. M. et al. (1991) *Acta. Microbiol. Pol.* 40:235–241). Metabolism studies of DMA by rat-liver microsomal preparations has found that this molecule is converted to 9-Hydroxymethyl-10-methylanthracene (9-OHMeMA) and 9,10-dihydroxymethyl-anthracene (9,10-DiOHMeA) (Lamparczyk, H. S. et al. (1984) *Carcinogenesis* 5:1405–1410). In addition, the trans-1,2-dihydro-1,2-dihydroxy derivative of DMA (DMA 1,2-diol) was found to be a major metabolite as determined by chromatographic, ultraviolet (UV), nuclear magnetic resonance (NMR), and mass spectral properties. DMA 1,2-diol was also created through the oxidation of DMA in an ascorbic acid-ferrous sulfate-EDTA system. Other dihydrodiols that are formed from DMA by metabolism are the trans-1,2- and 3,4-dihydrodiols of 9-OHMeMA (9-OHMeMA 1,2-diol and 9-OHMeMA 3,4-diol) while the further metabolism of DMA 1,2-diol can yield both of these dihydrodiols. Finally, when 9-OHMeMA is further metabolized, two main metabolites are formed; one was identified as 9,10-DiOHMeA and the other appeared to be 9-OHMeMA 3,4-diol.

The metabolism of 9-methylanthracene (9-MA), 9-hydroxymethylanthracene (9-OHMA), and 9,10-dimethylanthracene (9,10-DMA) by fungus also has been reported (Cerniglia, C. E. et al. (1990) *Appl. Environ. Microbiol.* 56:661–668). These compounds are also useful for generating DMA derivatives capable of blocking MMR. Compounds 9-MA and 9,10-DMA are metabolized by two pathways, one involving initial hydroxylation of the methyl group(s) and the other involving epoxidation of the 1,2- and 3,4-aromatic double bond positions, followed by enzymatic hydration to form hydroxymethyl trans-dihydrodiols. For 9-MA metabolism, the major metabolites identified are trans-1,2-dihydro-1,2-dihydroxy and trans-3,4-dihydro-3,4- dihydroxy derivatives of 9-MA and 9-OHMA, whereby 9-OHMA can be further metabolized to trans-1,2- and 3,4-dihydrodiol derivatives. Circular dichroism spectral analysis revealed that the major enantiomer for each dihydrodiol was predominantly in the S,S configuration, in contrast to the predominantly R,R configuration of the trans-dihydrodiol formed by mammalian enzyme systems. These results indicate that *Caenorhabditis elegans* metabolizes methylated anthracenes in a highly stereoselective manner that is different from that reported for rat liver microsomes.

The analogs as listed above provide an example but are not limited to anthracene-derived compounds capable of eliciting MMR blockade. Additional analogs that are of potential use for blocking MMR are shown in FIG. 8.

Other Classes of Small Molecular Weight Compounds that are Capable of Blocking MMR in vivo.

MMR is a multi-step process that involves the formation of protein complexes that detect mismatched bases or altered repetitive sequences and interface these mutations with enzymes that degrade the mutant base and repair the DNA with correct nucleotides. First, mismatched DNA is recognized by the mutS heterodimeric complex consisting of MSH2 and GTBP proteins. The DNA bound mutS complex is then recognized by the mutL heterdimeric complex that consists of PMS2 and MLH1 proteins. The mutL complex is thought to interface exonucleases with the mismatched DNA site, thus initiating this specialized DNA repair process. After the mismatched bases are removed, the DNA is repaired with a polymerase.

There are several steps in the normal process that can be targeted by small molecular weight compounds to block MMR. This application teaches of these steps and the types of compounds that may be used to block this process.

ATPase Inhibitors:

The finding that nonhydrolyzable forms of ATP are able to suppress MMR in vitro also suggest that the use for this type of compound can lead to blockade of MMR in vivo and mutation a host organism's genome (Galio, L. et al. (1999) *Nucl. Acids Res.* 27:2325–2331; Allen, D. J. et al. (1997) *EMBO J.* 16:4467–4476; Bjornson, K. P. et al. (2000) *Biochem.* 39:3176–3183). One can use a variety of screening methods described within this application to identify ATP analogs that block the ATP-dependent steps of mismatch repair in vivo.

Nuclease Inhibitors:

The removal of mismatched bases is a required step for effective MMR (Harfe, B. D. and S. Jinks-Robertson (2000) *Ann. Rev. Genet.* 34:359–399). This suggests that compounds capable of blocking this step can lead to blockade of MMR in vivo and mutation a host organism's genome. One can use a variety of screening methods described within this application to identify nuclease inhibitors analogs that block the nuclease steps of mismatch repair in vivo. An example of the types of nuclease inhibitors are but not limited to analogs of N-Ethylmaleimide, an endonuclease inhibitor (Huang, Y. C., et.al. (1995) *Arch. Biochem. Biophys.* 316:485), heterodimeric adenine-chain-acridine compounds, exonulcease III inhibitors (Belmont P, et.al., *Bioorg Med Chem Lett* (2000) 10:293–295), as well as antibiotic compounds such as Heliquinomycin, which have helicase inhibitory activity (Chino, M, et.al. *J. Antibiot.* (Tokyo) (1998) 51:480–486).

Polymerase Inhibitors:

Short and long patch repair is a required step for effective MMR (Modrich, P. (1994) *Science* 266:1959–1960). This suggests that compounds capable of blocking MMR-associated polymerization can lead to blockade of MMR in vivo and mutation a host organism's genome. One can use a variety of screening methods described within this application to identify polymerase inhibitors analogs that block the polymerization steps of mismatch repair in vivo. An example of DNA polymerase inhibitors that are useful in blocking MMR activity include, but are not limited to, analogs of actinomycin D (Martin, S. J., et.al. (1990) *J. Immunol.* 145:1859), Aphidicolin (Kuwakado, K. et.al. (1993) *Biochem. Pharmacol.* 46:1909) 1-(2'-Deoxy-2'-fluoro-beta-L-arabinofuranosyl)-5-methyluracil (L-FMAU) (Kukhanova M, et.al., *Biochem Pharmacol* (1998) 55:1181–1187), and 2',3'-dideoxyribonucleoside 5'-triphosphates (ddNTPs) (Ono, K., et.al., *Biomed Pharmacother* (1984) 38:382–389).

Chemical Inhibitors of Mismatch Repair Gene Expression

MMR is a multi-protein process that requires the cooperation of several proteins such as but not limited to mutS homologs, MSH2, MSH3, MSH6, GTBP; mutL homologs PMS1, PMS2, MLH1; and exonucleases and helicases such as MutH and MutY (Harfe, B. D. and S. Jinks-Robertson (2000) *Ann. Rev. Genet.* 34:359–399; Modrich, P. (1994) *Science* 266:1959–1960). Chemicals capable of blocking the expression of these genes can lead to the blockade of MMR. An example of a chemical that is capable of blocking MMR gene expression is an oligodeoxynucleotide that can specifically bind and degrade an MMR gene message and protein production as described by Chauhan D P, et.al. (*Clin Cancer Res* (2000) 6:3827–3831). One can use a variety of screening methods described within this application to identify inhibitors that block the expression and/or function of MMR genes in vivo.

DISCUSSION

The results described herein demonstrate the use of chemicals that can block mismatch repair of host organisms in vivo to produce genetic mutations. The results also demonstrate the use of reporter systems in host cells and organisms that are useful for screening chemicals capable of blocking MMR of the host organism. Moreover, the results demonstrate the use of chemical inhibitors to block MMR in mammalian cells, microbes, and plants to produce organisms with new output traits. The data presented herein provide novel approaches for producing genetically altered plants, microbes, and mammalian cells with output traits for commercial applications by inhibiting MMR with chemicals. This approach gives advantages over others that require the use of recombinant techniques to block MMR or to produce new output traits by expression of a foreign gene. This method will be useful in producing genetically altered host organisms for agricultural, chemical manufacturing, pharmaceutical, and environmental applications.

PMS2 (mouse) (SEQ ID NO:14)

MEQTEGVSTE CAKAIKPIDG KSVHQICSGQ VILSLSTAVK ELIENSVDAG ATTIDLRLKD 60

```
                                   -continued
YGVDLIEVSD NGCGVEEENF EGLALKHHTS KIQEFADLTQ VETFGFRGEA LSSLCALSDV      120

TISTCHGSAS VGTRLVFDHN GKITQKTPYP RPKGTTVSVQ HLFYTLPVRY KEFQRNIKKE      180

YSKMVQVLQA YCIISAGVRV SCTNQLGQGK RHAVVCTSGT SGMKENIGSV FGQKQLQSLI      240

PFVQLPPSDA VCEEYGLSTS GRHKTFSTFR ASFHSARTAP GGVQQTGSFS SSIRGPVTQQ      300

RSLSLSMRFY HMYNRHQYPF VVLNVSVDSE CVDINVTPDK RQILLQEEKL LLAVLKTSLI      360

GMFDSDANKL NVNQQPLLDV EGNLVKLHTA ELEKPVPGKQ DNSPSLKSTA DEKRVASISR      420

LREAFSLHPT KEIKSRGPET AELTRSFPSE KRGVLSSYPS DVISYRGLRG SQDKLVSPTD      480

SPGDCMDREK IEKDSGLSST SAGSEEEFST PEVASSFSSD YNVSSLEDRP SQETINCGDL      540

DCRPPGTGQS LKPEDHGYQC KALPLARLSP TNAKRFKTEE RPSNVNTSQR LPGPQSTSAA      600

EVDVAIKMNK RIVLLEFSLS SLAKRMKQLQ HLKAQNKHEL SYRKFRAKIC PGENQAAEDE      660

LRKEISKSMF AEMEILGQFN LGFIVTKLKE DLFLVDQHAA DEKYNFEMLQ QHTVLQAQRL      720

ITPQTLNLTA VNEAVLIENL EIFRKNGFDF VIDEDAPVTE RAKLISLPTS KNWTFGPQDI      780

DELIFMLSDS PGVMCRPSRV RQMFASRACR KSVMIGTALN ASEMKKLITH MGEMDHPWNC      840

PHGRPTMRHV ANLDVISQN                                                  859

PMS2 (mouse cDNA) (SEQ ID NO:15)

gaattccggt gaaggtcctg aagaatttcc agattcctga gtatcattgg aggagacaga      60
taacctgtcg tcaggtaacg atggtgtata tgcaacagaa atgggtgttc ctggagacgc     120
gtcttttccc gagagcggca ccgcaactct cccgcggtga ctgtgactgg aggagtcctg     180
catccatgga gcaaaccgaa ggcgtgagta cagaatgtgc taaggccatc aagcctattg     240
atgggaagtc agtccatcaa atttgttctg ggcaggtgat actcagttta agcaccgctg     300
tgaaggagtt gatagaaaat agtgtagatg ctggtgctac tactattgat ctaaggctta     360
aagactatgg ggtggacctc attgaagttt cagacaatgg atgtggggta agaagagaaa     420
actttgaagg tctagctctg aaacatcaca catctaagat tcaagagttt gccgacctca     480
cgcaggttga aactttcggc tttcgggggg aagctctgag ctctctgtgt gcactaagtg     540
atgtcactat atctacctgc cacgggtctg caagcgttgg gactcgactg gtgtttgacc     600
ataatgggaa aatcacccag aaaactccct accccgacc taaaggaacc acagtcagtg      660
tgcagcactt atttt ataca ctacccgtgc gttacaaaga gtttcagagg aacattaaaa     720
aggagtattc caaaatggtg caggtcttac aggcgtactg tatcatctca gcaggcgtcc     780
gtgtaagctg cactaatcag ctcggacagg ggaagcggca cgctgtggtg tgcacaagcg     840
gcacgtctgg catgaaggaa aatatcgggt ctgtgtttgg ccagaagcag ttgcaaagcc     900
tcattccttt tgttcagctg cccctagtga cgctgtgtg tgaagagtac ggcctgagca      960
cttcaggacg ccacaaaacc ttttctacgt ttcgggcttc atttcacagt gcacgcacgg     1020
cgccggggag agtgcaacag acaggcagtt tttcttcatc aatcagaggc cctgtgaccc     1080
agcaaaggtc tctaagcttg tcaatgaggt tttatcacat gtataaccgg catcagtacc     1140
catttgtcgt ccttaacgtt tccgttgact cagaatgtgt ggatattaat gtaactccag     1200
ataaaaggca aattctacta caagaagaga agctattgct ggccgtttta aagacctcct     1260
tgataggaat gtttgacagt gatgcaaaca agcttaatgt caaccagcag ccactgctag     1320
atgttgaagg taacttagta aagctgcata ctgcagaact agaaaagcct gtgccaggaa     1380
agcaagataa ctctccttca ctgaagagca cagcagacga gaaagggta gcatccatct     1440 ccaggctgag agaggccttt tctcttcatc ctactaaaga gatcaagtct agggtccag      1500
```

-continued

```
agactgctga actgacacgg agttttccaa gtgagaaaag gggcgtgtta tcctcttatc    1560
cttcagacgt catctcttac agaggcctcc gtggctcgca ggacaaattg gtgagtccca    1620
cggacagccc tggtgactgt atggacagag agaaaataga aaagactcag ggctcagca    1680
gcacctcagc tggctctgag aagagttca gcaccccaga agtggccagt agctttagca    1740
gtgactataa cgtgagctcc ctagaagaca gaccttctca ggaaaccata aactgtggtg    1800
acctggactg ccgtcctcca ggtacaggac agtccttgaa gccagaagac catggatatc    1860
aatgcaaagc tctacctcta gctcgtctgt cacccacaaa tgccaagcgc ttcaagacag    1920
aggaaagacc ctcaaatgtc aacatttctc aaagattgcc tggtcctcag agcacctcag    1980
cagctgaggt cgatgtagcc ataaaaatga ataagagaat cgtgctcctc gagttctctc    2040
tgagttctct agctaagcga atgaagcagt tacagcacct aaaggcgcag aacaaacatg    2100
aactgagtta cagaaaattt agggccaaga tttgccctgg agaaaaccaa gcagcagaag    2160
atgaactcag aaaagagatt agtaaatcga tgtttgcaga gatggagatc ttgggtcagt    2220
ttaacctggg atttatagta accaaactga agaggaccct cttcctggtg accagcatg    2280
ctgcggatga aagtacaac tttgagatgc tgcagcagca cacggtgctc caggcgcaga    2340
ggctcatcac accccagact ctgaacttaa ctgctgtcaa tgaagctgta ctgatagaaa    2400
atctggaaat attcagaaag aatggctttg actttgtcat tgatgaggat gctccagtca    2460
ctgaaagggc taaattgatt tccttaccaa ctagtaaaaa ctggaccttt ggaccccaag    2520
atatagatga actgatcttt atgttaagtg acagccctgg ggtcatgtgc cggccctcac    2580
gagtcagaca gatgtttgct tccagagcct gtcggaagtc agtgatgatt ggaacggcgc    2640
tcaatgcgag cgagatgaag aagctcatca cccacatggg tgagatggac caccccctgga    2700
actgccccca cggcaggcca accatgaggc acgttgccaa tctggatgtc atctctcaga    2760
actgacacac cccttgtagc atagagttta ttacagattg ttcggtttgc aaagagaagg    2820
ttttaagtaa tctgattatc gttgtacaaa aattagcatg ctgctttaat gtactggatc    2880
catttaaaag cagtgttaag gcaggcatga tggagtgttc ctctagctca gctacttggg    2940
tgatccggtg ggagctcatg tgagcccagg acttgagac cactccgagc cacattcatg    3000
agactcaatt caaggacaaa aaaaaaaga tattttgaa gccttttaaa aaaaaa        3056
PMS2 (human) (SEQ ID NO:16)
MERAESSSTE PAKAIKPIDR KSVHQICSGQ VVLSLSTAVK ELVENSLDAG ATNIDLKLKD     60
YGVDLIEVSD NGCGVEEENF EGLTLKHHTS KIQEFADLTQ VETFGFRGEA LSSLCALSDV    120
TISTCHASAK VGTRLMFDHN GKIIQKTPYP RPRGTTVSVQ QLFSTLPVRH KEFQRNTKKE    180
YAKMVQVLHA YCIISAGIRV SCTNQLGQGK RQPVVCTGGS PSIKENIGSV FGQKQLQSLI    240
PFVQLPPSDS VCEEYGLSCS DALHNLFYIS GFISQCTHGV GRSSTDRQFF FINRRPCDPA    300
KVCRLVNEVY HMYNRHQYPF VVLNISVDSE CVDINVTPDK RQILLQEEKL LLAVLKTSLI    360
GMFDSDVNKL NVSQQPLLDV EGNLTKMHAA DLEKPMVEKQ DQSPSLRTGE EKKDVSISRL    420
REAFSLRHTT ENKPHSPKTP EPRRSPLGQK RGMLSSSTSG AISDKGVLRP QKEAVSSSHG    480
PSDPTDRAEV EKDSGHGSTS VDSEGFSIPD TGSHCSSEYA ASSPGDRGSQ EHVDSQEKAP    540
ETDDSFSDVD CHSNQEDTGC KFRVLPQPTN LATPNTKRFK KEEILSSSDI CQKLVNTQDM    600
SASQVDVAVK INKKVVPLDF SMSSLAKRIK QLHHEAQQSE GEQNYRKFRA KICPGENQAA    660
EDELRKEISK TMFAEMEIIG QFNLGFIITK LNEDIFIVDQ HATDEKYNFE MLQQHTVLQG    720
QRLIAPQTLN LTAVNEAVLI ENLEIFRKNG FDFVIDENAP VTERAKLISL PTSKNWTFGP    780
```

-continued

```
QDVDELIFML SDSPGVMCRP SRVKQMFASR ACRKSVMIGT ALNTSEMKKL ITHMGEMDHP    840
WNCPHGRPTM RHIANLGVIS QN                                            862

PMS2 (human cDNA) (SEQ ID NO:17)
cgaggcggat cgggtgttgc atccatggag cgagctgaga gctcgagtac agaacctgct     60
aaggccatca aacctattga tcggaagtca gtccatcaga tttgctctgg caggtggta    120
ctgagtctaa gcactgcggt aaaggagtta gtagaaaaca gtctggatgc tggtgccact    180
aatattgatc taaagcttaa ggactatgga gtggatctta ttgaagtttc agacaatgga    240
tgtgggggtag aagaagaaaa cttcgaaggc ttaactctga acatcacac atctaagatt    300
caagagtttg ccgacctaac tcaggttgaa acttttggct tcgggggga agctctgagc    360
tcactttgtg cactgagcga tgtcaccatt tctacctgcc acgcatcggc aaggttgga    420
actcgactga tgtttgatca aatgggaaaa attatccaga aaaccccta cccccgcccc    480
agagggacca cagtcagcgt gcagcagtta ttttccacac tacctgtgcg ccataaggaa    540
tttcaaagga atattaagaa ggagtatgcc aaaatggtcc aggtcttaca tgcatactgt    600
atcatttcag caggcatccg tgtaagttgc accaatcagc ttggacaagg aaaacgacag    660
cctgtggtat gcacaggtgg aagccccagc ataaggaaa atatcggctc tgtgtttggg    720
cagaagcagt tgcaaagcct cattccttt gttcagctgc ccctagtga ctccgtgtgt    780
gaagagtacg gtttgagctg ttcggatgct ctgcataatc tttttttacat ctcaggtttc    840
atttcacaat gcacgcatgg agttggaagg agttcaacag acagacagtt tttcttatc    900
aaccggcggc cttgtgaccc agcaaaggtc tgcagactcg tgaatgaggt ctaccacatg    960
tataatcgac accagtatcc atttgttgtt cttaacattt ctgttgattc agaatgcgtt   1020
gatatcaatg ttactccaga taaaaggcaa attttgctac aagagaaaaa gcttttgttg   1080
gcagttttaa agacctcttt gataggaatg tttgatagtg atgtcaacaa gctaaatgtc   1140
agtcagcagc cactgctgga tgttgaaggt aacttaataa aaatgcatgc agcggatttg   1200
gaaaagccca tggtagaaaa gcaggatcaa tccccttcat taaggactgg agaagaaaaa   1260
aaagacgtgt ccatttccag actgcgagag gccttttctc ttcgtcacac aacagagaac   1320
aagcctcaca gcccaaagac tccagaacca agaaggagcc ctctaggaca gaaaagggt   1380
atgctgtctt ctagcacttc aggtgccatc tctgacaaag cgtcctgag acctcagaaa   1440
gaggcagtga gttccagtca cggacccagt gaccctacgg acagagcgga ggtggagaag   1500
gactcggggc acggcagcac ttccgtggat tctgagggt tcagcatccc agacacgggc   1560
agtcactgca gcagcgagta tgcggccagc tccccagggg caggggctc gcaggaacat   1620
gtggactctc aggagaaagc gcctgaaact gacgactctt tttcagatgt ggactgccat   1680
tcaaaccagg aagataccgg atgtaaattt cgagttttgc ctcagccaac taatctcgca   1740
accccaaaca caaagcgttt taaaaaagaa gaaattcttt ccagttctga catttgtcaa   1800
aagttagtaa atactcagga catgtcagcc tctcaggttg atgtagctgt gaaaattaat   1860
aagaaagttg tgccctgga cttttctatg agttctttag ctaaacgaat aaagcagtta   1920
catcatgaag cacagcaaag tgaagggga cagaattaca ggaagtttag ggcaaagatt   1980
tgtcctggag aaaatcaagc agccgaagat gaactaagaa aagagataag taaaacgatg   2040
tttgcagaaa tggaaatcat tggtcagttt aacctgggat ttataataac caaactgaat   2100
gaggatatct tcatagtgga ccagcatgcc acggacgaga gtataacttc gagatgctg   2160
cagcagcaca ccgtgctcca ggggcagagg ctcatagcac ctcagactct caacttaact   2220
```

```
                                -continued
gctgttaatg aagctgttct gatagaaaat ctggaaatat ttagaaagaa tggctttgat    2280
tttgttatcg atgaaaatgc tccagtcact gaaagggcta aactgatttc cttgccaact    2340
agtaaaaact ggaccttcgg accccaggac gtcgatgaac tgatcttcat gctgagcgac    2400
agccctgggg tcatgtgccg gccttcccga gtcaagcaga tgtttgcctc cagagcctgc    2460
cggaagtcgg tgatgattgg gactgctctt aacacaagcg agatgaagaa actgatcacc    2520
cacatggggg agatggacca ccctggaac tgtccccatg aaggccaac catgagacac      2580 atcgccaacc tgggtgtcat ttctcagaac tgaccgtagt cactgtatgg aataattggt    2640
tttatcgcag atttttatgt tttgaaagac agagtcttca ctaaccttt ttgttttaaa     2700 atgaaacctg ctacttaaaa aaatacaca tcacacccat ttaaaagtga tcttgagaac     2760
cttttcaaac c                                                         2771

PMS1 (human) (SEQ ID NO:18)
MKQLPAATVR LLSSSQTTTS VVSVVKELIE NSLDAGATSV DVKLENYGFD KIEVRDNGEG      60

IKAVDAPVMA MKYYTSKINS HEDLENLTTY GFRGEALGSI CCIAEVLITT RTAADNFSTQ    120

YVLDGSGHIL SQKPSHLGQG TTVTALRLFK NLPVRKQFYS TAKKCKDEIK KIQDLLMSFG    180

ILKPDLRIVF VHNKAVIWQK SRVSDHKMAL MSVLGTAVMN NMESFQYHSE ESQIYLSGFL    240

PKCDADHSFT SLSTPERSFI FINSRPVHQK DILKLIRHHY NLKCLKESTR LYPVFFLKID    300

VPTADVDVNL TPDKSQVLLQ NKESVLIALE NLMTTCYGPL PSTNSYENNK TDVSAADIVL    360

SKTAETDVLF NKVESSGKNY SNVDTSVIPF QNDMHNDESG KNTDDCLNHQ ISIGDFGYGH    420

CSSEISNIDK NTKNAFQDIS MSNVSWENSQ TEYSKTCFIS SVKHTQSENG NKDHIDESGE    480

NEEEAGLENS SEISADEWSR GNILKNSVGE NIEPVKILVP EKSLPCKVSN NNYPIPEQMN    540

LNEDSCNKKS NVIDNKSGKV TAYDLLSNRV IKKPMSASAL FVQDHRPQFL IENPKTSLED    600

ATLQIEELWK TLSEEEKLKY EEKATKDLER YNSQMKRAIE QESQMSLKDG RKKTKPTSAW    660

NLAQKHKLKT SLSNQPKLDE LLQSQIEKRR SQNIKMVQIP FSMKNLKINF KKQNKVDLEE    720

KDEPCLIHNL RFPDAWLMTS KTEVMLLNPY RVEEALLFKR LLENHKLPAE PLEKPIMLTE    780

SLFNGSHYLD VLYKMTADDQ RYSGSTYLSD PRLTANGFKI KLIPGVSITE NYLEIEGMAN    840

CLPFYGVADL KEILNAILNR NAKEVYECRP RKVISYLEGE AVRLSRQLPM YLSKEDIQDI    900

IYRMKHQFGN EIKECVHGRP FFHHLTYLPE TT                                  932

PMS1 (human) (SEQ ID NO:19)
ggcacgagtg gctgcttgcg gctagtggat ggtaattgcc tgcctcgcgc tagcagcaag     60
ctgctctgtt aaaagcgaaa atgaaacaat tgcctgcggc aacagttcga ctccttcaa    120 gttctcagat catcacttcg gtggtcagtg ttgtaaaaga gcttattgaa aactcctgg    180 atgctggtgc cacaagcgta gatgttaaac tggagaacta tggatttgat aaaattgagg   240
tgcgagataa cggggagggt atcaaggctg ttgatgcacc tgtaatgca atgaagtact    300 acacctcaaa aataaatagt catgaagatc ttgaaaattt gacaacttac ggttttcgtg   360
gagaagcctt ggggtcaatt tgttgtatag ctgaggtttt aattacaaca gaacggctg    420 ctgataattt tagcacccag tatgttttag atggcagtgg ccacatactt tctcagaaac   480
cttcacatct tggtcaaggt acaactgtaa ctgctttaag attatttaag aatctacctg   540
taagaaagca gttttactca actgcaaaaa aatgtaaaga tgaaataaaa aagatccaag   600
atctcctcat gagctttggt atccttaaac ctgacttaag gattgtcttt gtacataaca    660
aggcagttat ttggcagaaa agcagagtat cagatcacaa gatggctctc atgtcagttc   720
```

-continued

```
tggggactgc tgttatgaac aatatggaat cctttcagta ccactctgaa gaatctcaga      780
tttatctcag tggatttctt ccaaagtgtg atgcagacca ctctttcact agtctttcaa      840
caccagaaag aagtttcatc ttcataaaca gtcgaccagt acatcaaaaa gatatcttaa      900
agttaatccg acatcattac aatctgaaat gcctaaagga atctactcgt ttgtatcctg      960
ttttctttct gaaaatcgat gttcctacag ctgatgttga tgtaaattta acaccagata     1020
aaagccaagt attattacaa ataaggaat ctgttttaat tgctcttgaa atctgatga       1080 cgacttgtta tggaccatta cctagtacaa attcttatga aaataataaa acagatgttt     1140
ccgcagctga catcgttctt agtaaaacag cagaaacaga tgtgcttttt aataaagtgg     1200
aatcatctgg aaagaattat tcaaatgttg atacttcagt cattccattc caaaatgata     1260
tgcataatga tgaatctgga aaaaacactg atgattgttt aaatcaccag ataagtattg     1320
gtgactttgg ttatggtcat tgtagtagtg aaatttctaa cattgataaa aacactaaga     1380
atgcatttca ggacatttca atgagtaatg tatcatggga gaactctcag acggaatata     1440
gtaaaacttg ttttataagt tccgttaagc acacccagtc agaaaatggc aataaagacc     1500
atatagatga gagtggggaa aatgaggaag aagcaggtct tgaaaactct tcggaaattt     1560
ctgcagatga gtggagcagg ggaaatatac ttaaaaattc agtgggagag aatattgaac     1620
ctgtgaaaat tttagtgcct gaaaaaagtt taccatgtaa agtaagtaat aataattatc     1680
caatccctga acaaatgaat cttaatgaag attcatgtaa caaaaaatca aatgtaatag     1740
ataataaatc tggaaaagtt acagcttatg atttacttag caatcgagta atcaagaaac     1800
ccatgtcagc aagtgctctt tttgttcaag atcatcgtcc tcagtttctc atagaaaatc     1860
ctaagactag tttagaggat gcaacactac aaattgaaga actgtggaag acattgagtg     1920
aagaggaaaa actgaaatat gaagagaagg ctactaaaga cttggaacga tacaatagtc     1980
aaatgaagag agccattgaa caggagtcac aaatgtcact aaaagatggc agaaaaaaga     2040
taaaacccac cagcgcatgg aatttggccc agaagcacaa gttaaaaacc tcattatcta     2100
atcaaccaaa acttgatgaa ctccttcagt cccaaattga aaaagaagg agtcaaaata     2160 ttaaaatggt acagatcccc ttttctatga aaaacttaaa aataaatttt aagaaacaaa     2220
acaaagttga cttagaagag aaggatgaac cttgcttgat ccacaatctc aggtttcctg     2280
atgcatggct aatgacatcc aaaacagagg taatgttatt aaatccatat agagtagaag     2340
aagccctgct atttaaaaga cttcttgaga atcataaact tcctgcagag ccactggaaa     2400
agccaattat gttaacagag agtctttta atggatctca ttatttagac gttttatata     2460
aaatgacagc agatgaccaa agatacagtg gatcaactta cctgtctgat cctcgtctta     2520
cagcgaatgg tttcaagata aaattgatac caggagtttc aattactgaa aattacttgg     2580
aaatagaagg aatggctaat tgtctcccat tctatggagt agcagattta aaagaaattc     2640
ttaatgctat attaaacaga aatgcaaagg aagtttatga atgtagacct cgcaaagtga     2700
taagttattt agagggagaa gcagtgcgtc tatccagaca attacccatg tacttatcaa     2760
aagaggacat ccaagacatt atctacagaa tgaagcacca gtttggaaat gaaattaaag     2820
agtgtgttca tggtcgccca ttttttcatc atttaaccta tcttccagaa actacatgat     2880
taaatatgtt taagaagatt agttaccatt gaaattggtt ctgtcataaa acagcatgag     2940 tctggttttta aattatcttt gtattatgtg tcacatggtt attttttaaa tgaggattca     3000
ctgacttgtt tttatattga aaaaagttcc acgtattgta gaaaacgtaa ataaactaat     3060
aac                                                                  3063
```

-continued

MSH2 (human) (SEQ ID NO:20)

```
MAVQPKETLQ LESAAEVGFV RFFQGMPEKP TTTVRLFDRG DFYTAHGEDA LLAAREVFKT    60
QGVIKYMGPA GAKNLQSVVL SKMNFESFVK DLLLVRQYRV EVYKNRAGNK ASKENDWYLA   120
YKASPGNLSQ FEDILFGNND MSASIGVVGV KMSAVDGQRQ VGVGYVDSIQ RKLGLCEFPD   180
NDQFSNLEAL LIQIGPKECV LPGGETAGDM GKLRQIIQRG GILITERKKA DFSTKDIYQD   240
LNRLLKGKKG EQMNSAVLPE MENQVAVSSL SAVIKFLELL SDDSNFGQFE LTTFDFSQYM   300
KLDIAAVRAL NLFQGSVEDT TGSQSLAALL NKCKTPQGQR LVNQWTKQPL MDKNRIEERL   360
NLVEAFVEDA ELRQTLQEDL LRRFPDLNRL AKKFQRQAAN LQDCYRLYQG TNQLPNVIQA   420
LEKHEGKHQK LLLAVFVTPL TDLRSDFSKF QEMIETTLDM DQVENHEFLV KPSFDPNLSE   480
LREIMNDLEK KMQSTLISAA RDLGLDPGKQ IKLDSSAQFG YYFRVTCKEE KVLRNNKNFS   540
TVDIQKNGVK FTNSKLTSLN EEYTKNKTEY EEAQDAIVKE IVNISSGYVE PMQTLNDVLA   600
QLDAVVSFAH VSNGAPVPYV RPAILEKGQG RIILKASRHA CVEVQDEIAF IPNDVYFEKD   660
KQMFHIITGP NMGGKSTYIR QTGVIVLMAQ IGCFVPCESA EVSIVDCILA RVGAGDSQLK   720
GVSTFMAEML ETASILRSAT KDSLIIIDEL GRGTSTYDGF GLAWAISEYI ATKIGAFCMF   780
ATHFHELTAL ANQIPTVNNL HVTALTTEET LTMLYQVKKG VCDQSFGIHV AELANFPKHV   840
IECAKQKALE LEEFQYIGES QGYDIMEPAA KKCYLEREQG EKIIQEFLSK VKQMPFTEMS   900
EENITIKLKQ LKAEVIAKNN SFVNEIISRI KVTT                              934
```

MSH2 (human cDNA) (SEQ ID NO:21)

```
ggcgggaaac agcttagtgg gtgtgggggtc gcgcattttc ttcaaccagg aggtgaggag    60
gtttcgacat ggcggtgcag ccgaaggaga cgctgcagtt ggagagcgcg gccgaggtcg   120
gcttcgtgcg cttctttcag ggcatgccgg agaagccgac caccacagtg cgccttttcg   180
accggggcga cttctatacg gcgcacggcg aggacgcgct gctggccgcc cgggaggtgt   240
tcaagaccca gggggtgatc aagtacatgg ggccggcagg agcaaagaat ctgcagagtg   300
ttgtgcttag taaaatgaat tttgaatctt ttgtaaaaga tcttcttctg gttcgtcagt   360
atagagttga agtttataag aatagagctg gaaataaggc atccaaggag aatgattggt   420
atttggcata taaggcttct cctggcaatc tctctcagtt tgaagacatt ctctttggta   480
acaatgatat gtcagcttcc attggtgttg tgggtgttaa aatgtccgca gttgatggcc   540
agagacaggt tggagttggg tatgtggatt ccatacagag gaaactagga ctgtgtgaat   600
tccctgataa tgatcagttc tccaatcttg aggctctcct catccagatt ggaccaaagg   660
aatgtgtttt acccggagga gagactgctg gagacatggg gaaactgaga cagataattc   720
aaagaggagg aattctgatc acagaaagaa aaaagctga cttttccaca aaagacattt   780
atcaggacct caaccggttg ttgaaaggca aaaagggaga gcagatgaat agtgctgtat   840
tgccagaaat ggagaatcag gttgcagttt catcactgtc tgcggtaatc aagttttag    900
aactcttatc agatgattcc aactttggac agtttgaact gactactttt gacttcagcc   960
agtatatgaa attggatatt gcagcagtca gagcccttaa cctttttcag ggttctgttg  1020
aagataccac tggctctcag tctctggctg ccttgctgaa taagtgtaaa acccctcaag  1080
gacaaagact tgttaaccag tggattaagc agcctctcat ggataagaac agaatagagg  1140
agagattgaa tttagtggaa gcttttgtag aagatgcaga attgaggcag actttacaag  1200
aagatttact tcgtcgattc ccagatctta accgacttgc caagaagttt caaagacaag  1260
cagcaaactt acaagattgt taccgactct atcagggtat aaatcaacta cctaatgtta  1320
```

-continued

```
tacaggctct ggaaaaacat gaaggaaaac accagaaatt attgttggca gtttttgtga      1380
ctcctcttac tgatcttcgt tctgacttct ccaagtttca ggaaatgata gaaacaactt      1440
tagatatgga tcaggtggaa accatgaatt ccttgtaaaa accttcattt gatcctaatc      1500
tcagtgaatt aagagaaata atgaatgact tggaaaagaa gatgcagtca acattaataa      1560
gtgcagccag agatcttggc ttggaccctg gcaaacagat taaactggat tccagtgcac      1620
agtttggata ttactttcgt gtaacctgta aggaagaaaa agtccttcgt aacaataaaa      1680
actttagtac tgtagatatc cagaagaatg gtgttaaatt taccaacagc aaattgactt      1740
ctttaaatga gagtatacc aaaaataaaa cagaatatga agaagcccag gatgccattg      1800
ttaaagaaat tgtcaatatt tcttcaggct atgtagaacc aatgcagaca ctcaatgatg      1860
tgttagctca gctagatgct gttgtcagct ttgctcacgt gtcaaatgga gcacctgttc      1920
catatgtacg accagccatt ttggagaaag gacaaggaag aattatatta aaagcatcca      1980
ggcatgcttg tgttgaagtt caagatgaaa ttgcatttat tcctaatgac gtatactttg      2040
aaaaagataa acagatgttc cacatcatta ctggccccaa tatgggaggt aaatcaacat      2100
atattcgaca aactggggtg atagtactca tggcccaaat tgggtgtttt gtgccatgtg      2160
agtcagcaga agtgtccatt gtggactgca tcttagcccg agtaggggct ggtgacagtc      2220
aattgaaagg agtctccacg ttcatggctg aaatgttgga aactgcttct atcctcaggt      2280
ctgcaaccaa agattcatta ataatcatag atgaattggg aagaggaact tctacctacg      2340
atggatttgg gttagcatgg gctatatcag aatacattgc aacaaagatt ggtgcttttt      2400
gcatgtttgc aacccatttt catgaactta ctgccttggc caatcagata ccaactgtta      2460
ataatctaca tgtcacagca ctcaccactg aagagacctt aactatgctt tatcaggtga      2520
agaaaggtgt ctgtgatcaa agttttggga ttcatgttgc agagcttgct aatttcccta      2580
agcatgtaat agagtgtgct aaacagaaag ccctggaact tgaggagttt cagtatattg      2640
gagaatcgca aggatatgat atcatggaac agcagcaaa gaagtgctat ctggaaagag      2700
agcaaggtga aaaaattatt caggagttcc tgtccaaggt gaaacaaatg ccctttactg      2760
aaatgtcaga agaaaacatc acaataaagt taaaacagct aaaagctgaa gtaatagcaa      2820
agaataatag ctttgtaaat gaaatcattt cacgaataaa agttactacg tgaaaaatcc      2880
cagtaatgga atgaaggtaa tattgataag ctattgtctg taatagtttt atattgtttt      2940
atattaaccc tttttccata gtgttaactg tcagtgccca tgggctatca acttaataag      3000
atatttagta atattttact ttgaggacat tttcaaagat ttttattttg aaaaatgaga      3060
gctgtaactg aggactgttt gcaattgaca taggcaataa taagtgatgt gctgaatttt      3120
ataaataaaa tcatgtagtt tgtgg                                           3145
```

MLH1 (human) (SEQ ID NO:22)

```
MSFVAGVIRR LDETVVNRIA AGEVIQRPAN AIKEMIENCL DAKSTSIQVI VKEGGLKLIQ       60
IQDNGTGIRK EDLDIVCERF TTSKLQSFED LASISTYGFR GEALASISHV AHVTITTKTA      120
DGKCAYRASY SDGKLKAPPK PCAGNQGTQI TVEDLFYNIA TRRKALKNPS EEYGKILEVV      180
GRYSVHNAGI SFSVKKQGET VADVRTLPNA STVDNIRSIF GNAVSRELIE IGCEDKTLAF      240
KMNGYISNAN YSVKKCIFLL FINHRLVEST SLRKAIETVY AAYLPKNTHP FLYLSLEISP      300
QNVDVNVHPT KHEVHFLHEE SILERVQQHI ESKLLGSNSS RMYFTQTLLP GLAGPSGEMV      360
KSTTSLTSSS TSGSSDKVYA HQMVRTDSRE QKLDAFLQPL SKPLSSQPQA IVTEDKTDIS      420
SGRARQQDEE MLELPAPAEV AAKNQSLEGD TTKGTSEMSE KRGPTSSNPR KRHREDSDVE      480
```

-continued

| | | | | |
|---|---|---|---|---|
|MVEDDSRKEM|TAACTPRRRI|INLTSVLSLQ|EEINEQGHEV|LREMLHNHSF VGCVNPQWAL 540|
|AQHQTKLYLL|NTTKLSEELF|YQILIYDFAN|FGVLRLSEPA|PLFDLAMLAL DSPESGWTEE 600|
|DGPKEGLAEY|IVEFLKKKAE|MLADYFSLEI|DEEGNLIGLP|LLIDNYVPPL EGLPIFILRL 660|
|ATEVNWDEEK|ECFESLSKEC|AMFYSIRKQY|ISEESTLSGQ|QSEVPGSIPN SWKWTVEHIV 720|
|YKALRSHILP|PKHFTEDGNI|LQLANLPDLY|KVFERC| 756|

MLH1 (human) (SEQ ID NO:23)

| | | | | | |
|---|---|---|---|---|---|
|cttggctctt|ctggcgccaa|aatgtcgttc|gtggcagggg|ttattcggcg|gctggacgag 60|
|acagtggtga|accgcatcgc|ggcggggaa|gttatccagc|ggccagctaa|tgctatcaaa 120|
|gagatgattg|agaactgttt|agatgcaaaa|tccacaagta|ttcaagtgat|tgttaaagag 180|
|ggaggcctga|agttgattca|gatccaagac|aatggcaccg|gatcaggaa|agaagatctg 240|
|gatattgtat|gtgaaaggtt|cactactagt|aaactgcagt|cctttgagga|tttagccagt 300|
|atttctacct|atggctttcg|aggtgaggct|ttggccagca|taagccatgt|ggctcatgtt 360|
|actattacaa|cgaaaacagc|tgatggaaag|tgtgcataca|gagcaagtta|ctcagatgga 420|
|aaactgaaag|cccctcctaa|accatgtgct|ggcaatcaag|ggacccagat|cacggtggag 480|
|gaccttttt|acaacatagc|cacgaggaga|aaagctttaa|aaaatccaag|tgaagaatat 540|
|gggaaaattt|tggaagttgt|tggcaggtat|tcagtacaca|atgcaggcat|tagtttctca 600|
|gttaaaaaac|aaggagagac|agtagctgat|gttaggacac|acccaatgc|ctcaaccgtg 660|
|gacaatattc|gctccatctt|tggaaatgct|gttagtcgag|aactgataga|aattggatgt 720|
|gaggataaaa|ccctagcctt|caaaatgaat|ggttacatat|ccaatgcaaa|ctactcagtg 780|
|aagaagtgca|tcttcttact|cttcatcaac|catcgtctgg|tagaatcaac|ttccttgaga 840|
|aaagccatag|aaacagtgta|tgcagcctat|ttgcccaaaa|acacacaccc|attcctgtac 900|
|ctcagtttag|aaatcagtcc|ccagaatgtg|gatgttaatg|tgcaccccac|aaagcatgaa 960|
|gttcacttcc|tgcacgagga|gagcatcctg|agcgggtgc|agcagcacat|cgagagcaag 1020|
|ctcctgggct|ccaattcctc|caggatgtac|ttcacccaga|ctttgctacc|aggacttgct 1080|
|ggcccctctg|gggagatggt|taaatccaca|acaagtctga|cctcgtcttc|tacttctgga 1140|
|agtagtgata|aggtctatgc|ccaccagatg|gttcgtacag|attcccggga|acagaagctt 1200|
|gatgcatttc|tgcagcctct|gagcaaaccc|ctgtccagtc|agccccaggc|cattgtcaca 1260|
|gaggataaga|cagatatttc|tagtggcagg|gctaggcagc|aagatgagga|gatgcttgaa 1320|
|ctcccagccc|ctgctgaagt|ggctgccaaa|atcagagct|tggagggga|tacaacaaag 1380|
|gggacttcag|aaatgtcaga|agagagagga|cctacttcca|gcaaccccag|aaagagacat 1440|
|cgggaagatt|ctgatgtgga|aatggtggaa|gatgattccc|gaaaggaaat|gactgcagct 1500|
|tgtacccccc|ggagaaggat|cattaacctc|actagtgttt|tgagtctcca|ggaagaaatt 1560|
|aatgagcagg|gacatgaggt|tctccgggag|atgttgcata|accactcctt|cgtgggctgt 1620|
|gtgaatcctc|agtgggcctt|ggcacagcat|caaaccaagt|tataccttct|caacaccacc 1680|
|aagcttagtg|aagaactgtt|ctaccagata|ctcatttatg|attttgccaa|ttttggtgtt 1740|
|ctcaggttat|cggagccagc|accgctcttt|gaccttgcca|tgcttgcctt|agatagtcca 1800|
|gagagtggct|ggacagagga|agatggtccc|aaagaaggac|ttgctgaata|cattgttgag 1860|
|tttctgaaga|agaaggctga|gatgcttgca|gactatttct|ctttggaaat|tgatgaggaa 1920|
|gggaacctga|ttggattacc|ccttctgatt|gacaactatg|tgccccttt|ggagggactg 1980|
|cctatcttca|ttcttcgact|agccactgag|gtgaattggg|acgaagaaaa|ggaatgtttt 2040|

-continued

```
gaaagcctca gtaaagaatg cgctatgttc tattccatcc ggaagcagta catatctgag      2100
gagtcgaccc tctcaggcca gcagagtgaa gtgcctggct ccattccaaa ctcctggaag      2160
tggactgtgg aacacattgt ctataaagcc ttgcgctcac acattctgcc tcctaaacat      2220
ttcacagaag atggaaatat cctgcagctt gctaacctgc ctgatctata caaagtcttt      2280
gagaggtgtt aaatatggtt atttatgcac tgtgggatgt gttcttcttt ctctgtattc      2340
cgatacaaag tgttgtatca agtgtgata tacaaagtgt accaacataa gtgttggtag       2400
cacttaagac ttatacttgc cttctgatag tattcctta tacacagtgg attgattata       2460
aataaataga tgtgtcttaa cata                                             2484
``` hPMS2-134 (human) (SEQ ID NO:24)

```
MERAESSSTE PAKAIKPIDR KSVHQICSGQ VVLSLSTAVK ELVENSLDAG ATNIDLKLKD       60

YGVDLIEVSD NGCGVEEENF EGLTLKHHTS KIQEFADLTQ VETFGFRGEA LSSLCALSDV     120

TISTCHASAK VGT                                                        133
``` hPMS2-134 (human cDNA) (SEQ ID NO:25)

```
cgaggcggat cgggtgttgc atccatggag cgagctgaga gctcgagtac agaacctgct       60
aaggccatca aacctattga tcggaagtca gtccatcaga tttgctctgg gcaggtggta      120
ctgagtctaa gcactgcggt aaaggagtta gtagaaaaca gtctggatgc tggtgccact      180
aatattgatc taaagcttaa ggactatgga gtggatctta ttgaagtttc agacaatgga      240
tgtggggtag aagaagaaaa cttcgaaggc ttaactctga acatcacac atctaagatt       300 caagagtttg ccgacctaac tcaggttgaa acttttggct ttcgggggga agctctgagc      360
tcactttgtg cactgagcga tgtcaccatt tctacctgcc acgcatcggc gaaggttgga      420
acttga                                                                426
```

GTBP (human) (SEQ ID NO:26)

```
MSRQSTLYSF FPKSPALSDA NKASARASRE GGRAAAAPGA SPSPGGDAAW SEAGPGPRPL       60

ARSASPPKAK NLNGGLRRSV APAAPTSCDF SPGDLVWAKM EGYPWWPCLV YNHPFDGTFI     120

REKGKSVRVH VQFFDDSPTR GWVSKRLLKP YTGSKSKEAQ KGGHFYSAKP EILRAMQRAD     180

EALNKDKIKR LELAVCDEPS EPEEEEEMEV GTTYVTDKSE EDNEIESEEE VQPKTQGSRR     240

SSRQIKKRRV ISDSESDIGG SDVEFKPDTK EEGSSDEISS GVGDSESEGL NSPVKVARKR     300

KRMVTGNGSL KRKSSRKETP SATKQATSIS SETKNTLRAF SAPQNSESQA HVSGGGDDSS     360

RPTVWYHETL EWLKEEKRRD EHRRRPDHPD FDASTLYVPE DFLNSCTPGM RKWWQIKSQN     420

FDLVICYKVG KFYELYHMDA LIGVSELGLV FMKGNWAHSG FPEIAFGRYS DSLVQKGYKV     480

ARVEQTETPE MMEARCRKMA HISKYDRVVR REICRIITKG TQTYSVLEGD PSENYSKYLL     540

SLKEKEEDSS GHTRAYGVCF VDTSLGKFFI GQFSDDRHCS RFRTLVAHYP PVQVLFEKGN     600

LSKETKTILK SSLSCSLQEG LIPGSQFWDA SKTLRTLLEE EYFREKLSDG IGVMLPQVLK     660

GMTSESDSIG LTPGEKSELA LSALGGCVFY LKKCLIDQEL LSMANFEEYI PLDSDTVSTT     720

RSGATFTKAY QRMVLDAVTL NNLEIFLNGT NGSTEGTLLE RVDTCHTPFG KRLLKQWLCA     780

PLCNHYAIND RLDAIEDLMV VPDKISEVVE LLKKLPDLER LLSKIHNVGS PLKSQNHPDS     840

RAIMYEETTY SKKKIIDFLS ALEGFKVMCK IIGIMEEVAD GFKSKILKQV ISLQTKNPEG     900

RFPDLTVELN RWDTAFDHEK ARKTGLITPK AGFDSDYDQA LADIRENEQS LLEYLEKQRN     960

RIGCRTIVYW GIGRNRYQLE IPENFTTRNL PEEYELKSTK KGCKRYWTKT IEKKLANLIN    1020

AEERRDVSLK DCMRRLFYNF DKNYKDWQSA VECIAVLDVL LCLANYSRGG DGPMCRPVIL    1080
```

```
                              -continued
LPEDTPPFLE LKGSRHPCIT KTFFGDDFIP NDILIGCEEE EQENGKAYCV LVTGPNMGGK     1140

STLMRQAGLL AVMAQMGCYV PAEVCRLTPI DRVFTRLGAS DRIMSGESTF FVELSETASI     1200

LMHATAHSLV LVDELGRGTA TFDGTAIANA VVKELAETIK CRTLFSTHYH SLVEDYSQNV     1260

AVRLGHMACM VENECEDPSQ ETITFLYKFI KGACPKSYGF NAARLANLPE EVIQKGHRKA     1320

REFEKMNQSL RLFREVCLAS ERSTVDAEAV HKLLTLIKEL                          1360

GTBP (human cDNA) (SEQ ID NO:27)

gccgcgcggt agatgcggtg cttttaggag ctccgtccga cagaacggtt gggccttgcc      60
ggctgtcggt atgtcgcgac agagcaccct gtacagcttc ttccccaagt ctccggcgct     120
gagtgatgcc aacaaggcct cggccagggc ctcacgcgaa ggcggccgtg ccgccgctgc     180
ccccggggcc tctccttccc caggcgggga tgcggcctgg agcgaggctg gcctgggcc      240 caggcccttg gcgcgctccg cgtcaccgcc caaggcgaag aacctcaacg gagggctgcg     300
gagatcggta gcgcctgctg cccccaccag ttgtgacttc tcaccaggag atttggtttg     360
ggccaagatg gagggttacc cctggtggcc ttgtctggtt acaaccacc cctttgatgg      420 aacattcatc cgcgagaaag ggaaatcagt ccgtgttcat gtacagtttt ttgatgacag     480
cccaacaagg ggctgggtta gcaaaaggct tttaaagcca tatacaggtt caaaatcaaa     540
ggaagcccag aagggaggtc attttacag tgcaaagcct gaaatactga gagcaatgca      600
acgtgcagat gaagccttaa ataaagacaa gattaagagg cttgaattgg cagtttgtga     660
tgagccctca gagccagaag aggaagaaga gatggaggta ggcacaactt acgtaacaga     720
taagagtgaa aagataatg aaattgagag tgaagaggaa gtacagccta agacacaagg      780
atctaggcga agtagccgcc aaataaaaaa acgaagggtc atatcagatt ctgagagtga     840
cattggtggc tctgatgtgg aatttaagcc agacactaag gaggaaggaa gcagtgatga     900
aataagcagt ggagtggggg atagtgagag tgaaggcctg aacagccctg tcaaagttgc     960
tcgaaagcgg aagagaatgg tgactggaaa tggctctctt aaaaggaaaa gctctaggaa    1020
ggaaacgccc tcagccacca acaagcaac tagcatttca tcagaaacca agaatacttt     1080
gagagctttc tctgcccctc aaaattctga atcccaagcc cacgttagtg gaggtggtga    1140
tgacagtagt cgccctactg tttggtatca tgaaacttta aatggcttaa aggaggaaaa    1200
gagaagagat gagcacagga ggaggcctga tcaccccgat tttgatgcat ctacactcta    1260
tgtgcctgag gatttcctca attcttgtac tcctgggatg aggaagtggt ggcagattaa    1320
gtctcagaac tttgatcttg tcatctgtta caaggtgggg aaattttatg agctgtacca    1380
catggatgct cttattggag tcagtgaact ggggctggta ttcatgaaag caactgggc     1440 ccattctggc tttcctgaaa ttgcatttgg ccgttattca gattccctgg tgcagaaggg    1500
ctataaagta gcacgagtgg aacagactga gactccagaa atgatggagg cacgatgtag    1560
aaagatggca catatatcca agtatgatag agtggtgagg agggagatct gtaggatcat    1620
taccaagggt acacagactt acagtgtgct ggaaggtgat ccctctgaga actacagtaa    1680
gtatcttctt agcctcaaag aaaaagagga agattcttct ggccatactc gtgcatatgg    1740
tgtgtgcttt gttgatactt cactgggaaa gttttcata ggtcagtttt cagatgatcg     1800
ccattgttcg agatttagga ctctagtggc acactatccc ccagtacaag ttttatttga    1860
aaaaggaaat ctctcaaagg aaactaaaac aattctaaag agttcattgt cctgttctct    1920
tcaggaaggt ctgataccc gctcccagtt tgggatgca tccaaaactt tgagaactct      1980
ccttgaggaa gaatatttta gggaaaagct aagtgatggc attggggtga tgttaccca     2040
```

-continued

| | | | | | |
|---|---|---|---|---|---|
| ggtgcttaaa | ggtatgactt | cagagtctga | ttccattggg | ttgacaccag | gagagaaaag | 2100 |
| tgaattggcc | ctctctgctc | taggtggttg | tgtcttctac | ctcaaaaaat | gccttattga | 2160 |
| tcaggagctt | ttatcaatgg | ctaattttga | agaatatatt | cccttggatt | ctgacacagt | 2220 |
| cagcactaca | agatctggtg | ctatcttcac | caaagcctat | caacgaatgg | tgctagatgc | 2280 |
| agtgacatta | aacaacttgg | agattttct | gaatggaaca | aatggttcta | ctgaaggaac | 2340 |
| cctactagag | agggttgata | cttgccatac | tccttttggt | aagcggctcc | taaagcaatg | 2400 |
| gctttgtgcc | ccactctgta | accattatgc | tattaatgat | cgtctagatg | ccatagaaga | 2460 |
| cctcatggtt | gtgcctgaca | aaatctccga | agttgtagag | cttctaaaga | agcttccaga | 2520 |
| tcttgagagg | ctactcagta | aaattcataa | tgttgggtct | cccctgaaga | gtcagaaacca | 2580 |
| cccagacagc | agggctataa | tgtatgaaga | aactacatac | agcaagaaga | agattattga | 2640 |
| ttttctttct | gctctggaag | gattcaaagt | aatgtgtaaa | attatagga | tcatggaaga | 2700 |
| agttgctgat | ggttttaagt | ctaaaatcct | taagcaggtc | atctctctgc | agacaaaaaa | 2760 |
| tcctgaaggt | cgttttcctg | atttgactgt | agaattgaac | cgatgggata | cagcctttga | 2820 |
| ccatgaaaag | gctcgaaaga | ctggacttat | tactcccaaa | gcaggctttg | actctgatta | 2880 |
| tgaccaagct | cttgctgaca | taagagaaaa | tgaacagagc | ctcctggaat | acctagagaa | 2940 |
| acagcgcaac | agaattggct | gtaggaccat | agtctattgg | gggattggta | ggaaccgtta | 3000 |
| ccagctggaa | attcctgaga | attttcaccac | tcgcaatttg | ccagaagaat | acgagttgaa | 3060 |
| atctaccaag | aagggctgta | aacgatactg | gaccaaaact | attgaaaaga | agttggctaa | 3120 |
| tctcataaat | gctgaagaac | ggagggatgt | atcattgaag | gactgcatgc | ggcgactgtt | 3180 |
| ctataacttt | gataaaaatt | acaaggactg | gcagtctgct | gtagagtgta | tcgcagtgtt | 3240 |
| ggatgtttta | ctgtgcctgg | ctaactatag | tcgagggggt | gatggtccta | tgtgtcgccc | 3300 |
| agtaattctg | ttgccggaag | ataccccccc | cttcttagag | cttaaaggat | cacgccatcc | 3360 |
| ttgcattacg | aagacttttt | ttggagatga | ttttattcct | aatgacattc | taataggctg | 3420 |
| tgaggaagag | gagcaggaaa | atggcaaagc | ctattgtgtg | cttgttactg | gaccaaatat | 3480 |
| gggggggcaag | tctacgctta | tgagacaggc | tggcttatta | gctgtaatgg | cccagatggg | 3540 |
| ttgttacgtc | cctgctgaag | tgtgcaggct | cacaccaatt | gatagagtgt | tactagact | 3600 |
| tggtgcctca | gacagaataa | tgtcaggtga | agtacattt | tttgttgaat | taagtgaaac | 3660 |
| tgccagcata | ctcatgcatg | caacagcaca | ttctctggtg | cttgtggatg | aattaggaag | 3720 |
| aggtactgca | acatttgatg | ggacggcaat | agcaaatgca | gttgttaaag | aacttgctga | 3780 |
| gactataaaa | tgtcgtacat | tatttcaac | tcactaccat | tcattagtag | aagattattc | 3840 |
| tcaaaatgtt | gctgtgcgcc | taggacatat | ggcatgcatg | gtagaaaatg | aatgtgaaga | 3900 |
| ccccagccag | gagactatta | cgttcctcta | taaattcatt | aagggagctt | gtcctaaaag | 3960 |
| ctatggcttt | aatgcagcaa | ggcttgctaa | tctcccagag | gaagttattc | aaaagggaca | 4020 |
| tagaaaagca | agagaatttg | agaagatgaa | tcagtcacta | cgattatttc | gggaagtttg | 4080 |
| cctggctagt | gaaaggtcaa | ctgtagatgc | tgaagctgtc | cataaattgc | tgactttgat | 4140 |
| taaggaatta | tagactgact | acattggaag | ctttgagttg | acttctgaca | aggtggtaa | 4200 |
| attcagacaa | cattatgatc | taataaactt | tattttttaa | aaat | | 4244 |

MSH3 (human) (SEQ ID NO:28)

MSRRKPASGG LAASSSAPAR QAVLSRFFQS TGSLKSTSSS TGAADQVDPG AAAAAAPPAP    60

AFPPQLPPHV ATEIDRRKKR PLENDGPVKK KVKKVQQKEG GSDLGMSGNS EPKKCLRTRN   120

-continued

| | | | | | |
|---|---|---|---|---|---|
| VSKSLEKLKE | FCCDSALPQS | RVQTESLQER | FAVLPKCTDF | DDISLLHAKN | AVSSEDSKRQ | 180
| INQKDTTLFD | LSQFGSSNTS | HENLQKTASK | SANKRSKSIY | TPLELQYIEM | KQQHKDAVLC | 240
| VECGYKYRFF | GEDAEIAARE | LNIYCHLDHN | FMTASIPTHR | LFVHVRRLVA | KGYKVGVVKQ | 300
| TETAALKAIG | DNRSSLFSRK | LTALYTKSTL | IGEDVNPLIK | LDDAVNVDEI | MTDTSTSYLL | 360
| CISENKENVR | DKKKGNIFIG | IVGVQPATGE | VVFDSFQDSA | SRSELETRMS | SLQPVELLLP | 420
| SALSEQTEAL | IHRATSVSVQ | DDRIRVERMD | NIYFEYSHAF | QAVTEFYAKD | TVDIKGSQII | 480
| SGIVNLEKPV | ICSLAAIIKY | LKEFNLEKML | SKPENFKQLS | SKMEFMTING | TTLRNLEILQ | 540
| NQTDMKTKGS | LLWVLDHTKT | SFGRRKLKKW | VTQPLLKLRE | INARLDAVSE | VLHSESSVFG | 600
| QIENHLRKLP | DIERGLCSIY | HKKCSTQEFF | LTVKTLYHLK | SEFQAIIPAV | NSHIQSDLLR | 660
| TVILEIPELL | SPVEHYLKIL | NEQAAKVGDK | TELFKDLSDF | PLIKKRKDEI | QGVIDEIRMH | 720
| LQEIRKILKN | PSAQYVTVSG | QEFMIEIKNS | AVSCIPTDWV | KVGSTKAVSP | FHSPFIVENY | 780
| RHLNQLREQL | VLDCSAEWLD | FLEKFSEHYH | SLCKAVHHLA | TVDCIFSLAK | VAKQGDYCRP | 840
| TVQEERKIVI | KNGRHPVIDV | LLGEQDQYVP | NNTDLSEDSE | RVMIITGPNM | GGKSSYIKQV | 900
| ALITIMAQIG | SYVPAEEATI | GIVDGIFTRM | GAADNIYKGR | STFMEELTDT | AEIIRKATSQ | 960
| SLVILDELGR | GTSTHDGIAI | AYATLEYFIR | DVKSLTLFVT | HYPPVCELEK | NYSHQVGNYH | 1020
| MGFLVSEDES | KLDPGAAEQV | PDFVTFLYQI | TRGIAARSYG | LNVAKLADVP | GEILKKAAHK | 1080
| SKELEGLINT | KRKRLKYFAK | LWTMHNAQDL | QKWTEEFNME | ETQTSLLH | | 1128

MSH3 (human DNA) (SEQ ID NO:29)

| | | | | | |
|---|---|---|---|---|---|
| gggcacgagc | cctgccatgt | ctcgccggaa | gcctgcgtcg | gcggcctcg | ctgcctccag | 60
| ctcagcccct | gcgaggcaag | cggttttgag | ccgattcttc | cagtctacgg | gaagcctgaa | 120
| atccacctcc | tcctccacag | gtgcagccga | ccaggtggac | cctggcgctg | cagcggccgc | 180
| agcgccccca | gcgcccgcct | tcccgcccca | gctgccgccg | cacgtagcta | cagaaattga | 240
| cagaagaaag | aagagaccat | tggaaaatga | tgggcctgtt | aaaagaaag | taagaaagt | 300
| ccaacaaaag | gaaggaggaa | gtgatctggg | aatgtctggc | aactctgagc | caaagaaatg | 360
| tctgaggacc | aggaatgttt | caaagtctct | ggaaaaattg | aaagaattct | gctgcgattc | 420
| tgcccttcct | caaagtagag | tccagacaga | atctctgcag | gagagatttg | cagttctgcc | 480
| aaaatgtact | gattttgatg | atatcagtct | tctacacgca | aagaatgcag | tttcttctga | 540
| agattcgaaa | cgtcaaatta | tcaaaagga | cacaacactt | tttgatctca | gtcagtttgg | 600
| atcatcaaat | acaagtcatg | aaaatttaca | gaaaactgct | tccaaatcag | ctaacaaacg | 660
| gtccaaaagc | atctatacgc | cgctagaatt | acaatacata | gaaatgaagc | agcagcacaa | 720
| agatgcagtt | tgtgtgtgg | aatgtggata | taagtataga | ttcttttggg | aagatgcaga | 780
| gattgcagcc | cgagagctca | atatttattg | ccatttagat | cacaacttta | tgacagcaag | 840
| tatacctact | cacagactgt | tgttcatgt | acgccgcctg | gtggcaaaag | gatataaggt | 900
| gggagttgtg | aagcaaactg | aaactgcagc | attaaaggcc | attggagaca | acagaagttc | 960
| actcttttcc | cggaaattga | ctgcccttta | tacaaaatct | acacttattg | gagaagatgt | 1020
| gaatcccta | atcaagctgg | atgatgctgt | aaatgttgat | gagataatga | ctgatacttc | 1080
| taccagctat | cttctgtgca | tctctgaaaa | taaggaaaat | gttagggaca | aaaaaaggg | 1140
| caacattttt | attggcattg | tgggagtgca | gcctgccaca | ggcgaggttg | tgtttgatag | 1200
| tttccaggac | tctgcttctc | gttcagagct | agaaacccgg | atgtcaagcc | tgcagccagt | 1260
| agagctgctg | cttccttcgg | ccttgtccga | gcaaacagag | gcgctcatcc | acagagccac | 1320

-continued

```
atctgttagt gtgcaggatg acagaattcg agtcgaaagg atggataaca tttatttga      1380
atacagccat gctttccagg cagttacaga gttttatgca aaagatacag ttgacatcaa      1440
aggttctcaa attatttctg gcattgttaa cttagagaag cctgtgattt gctctttggc      1500
tgccatcata aaatacctca agaattcaa cttggaaaag atgctctcca acctgagaa        1560
ttttaaacag ctatcaagta aaatggaatt tatgacaatt aatggaacaa cattaaggaa      1620
tctggaaatc ctacagaatc agactgatat gaaaaccaaa ggaagtttgc tgtgggtttt      1680
agaccacact aaaacttcat tgggagacg gaagttaaag aagtgggtga cccagccact       1740
ccttaaatta agggaaataa atgcccggct tgatgctgta tcggaagttc tccattcaga      1800
atctagtgtg tttggtcaga tagaaaatca tctacgtaaa ttgcccgaca tagagagggg      1860
actctgtagc atttatcaca aaaatgttc tacccaagag ttcttcttga ttgtcaaaac       1920
tttatatcac ctaaagtcag aatttcaagc aataatacct gctgttaatt cccacattca     1980
gtcagacttg ctccggaccg ttattttaga aattcctgaa ctcctcagtc cagtggagca     2040
ttacttaaag atactcaatg aacaagctgc caaagttggg gataaaactg aattatttaa     2100
agaccttttct gacttccctt taataaaaaa gaggaaggat gaaattcaag gtgttattga    2160
cgagatccga atgcatttgc aagaaatacg aaaaatacta aaaatccttt ctgcacaata    2220
tgtgacagta tcaggacagg agtttatgat agaaataaag aactctgctg tatcttgtat     2280
accaactgat tgggtaaagg ttggaagcac aaaagctgtg agccgctttc actctccttt    2340
tattgtagaa aattacagac atctgaatca gctccgggag cagctagtcc ttgactgcag    2400
tgctgaatgg cttgattttc tagagaaatt cagtgaacat tatcactcct tgtgtaaagc    2460
agtgcatcac ctagcaactg ttgactgcat tttctccctg gccaaggtcg ctaagcaagg   2520
agattactgc agaccaactg tacaagaaga agaaaaatt gtaataaaaa atggaaggca     2580
ccctgtgatt gatgtgttgc tgggagaaca ggatcaatat gtcccaaata atacagattt    2640
atcagaggac tcagagagag taatgataat taccggacca acatggggtg aaagagctc     2700
ctacataaaa caagttgcat tgattaccat catggctcag attggctcct atgttcctgc    2760
agaagaagcg acaattggga ttgtggatgg cattttcaca aggatgggtg ctgcagacaa    2820
tatatataaa ggacggagta catttatgga agaactgact gacacagcag aaataatcag    2880
aaaagcaaca tcacagtcct tggttatctt ggatgaacta ggaagaggga cgagcactca    2940
tgatggaatt gccattgcct atgctacact tgagtatttc atcagagatg tgaaatcctt    3000
aaccctgttt gtcacccatt atccgccagt ttgtgaacta gaaaaaaatt actcacacca    3060
ggtggggaat taccacatgg gattcttggt cagtgaggat gaaagcaaac tggatccagg    3120
cgcagcagaa caagtccctg attttgtcac cttcctttac caaataacta gaggaattgc    3180
agcaaggagt tatggattaa atgtggctaa actagcagat gttcctggag aaattttgaa    3240
gaaagcagct cacaagtcaa aagagctgga aggattaata aatacgaaaa gaaagagact    3300
caagtatttt gcaaagttat ggacgatgca taatgcacaa gacctgcaga gtggacaga     3360
ggagttcaac atggaagaaa cacagacttc tcttcttcat taaaatgaag actacatttg    3420
tgaacaaaaa atggagaatt aaaaatacca actgtacaaa ataactctcc agtaacagcc    3480
tatctttgtg tgacatgtga gcataaaatt atgaccatgg tatattccta ttggaaacag    3540
agaggttttt ctgaagacag tcttttttcaa gtttctgtct tcctaacttt tctacgtata    3600
aacactcttg aatagacttc cactttgtaa ttagaaaatt ttatggacag taagtccagt    3660
aaagccttaa gtggcagaat ataattccca agcttttgga gggtgatata aaaatttact    3720
```

```
tgatattttt atttgtttca gttcagataa ttggcaactg ggtgaatctg gcaggaatct      3780
atccattgaa ctaaaataat tttattatgc aaccagttta tccaccaaga acataagaat      3840
tttttataag tagaaagaat tggccaggca tggtggctca tgcctgtaat cccagcactt      3900
tgggaggcca aggtaggcag atcacctgag gtcaggagtt caagaccagc ctggccaaca      3960
tggcaaaacc ccatctttac taaaaatata aagtacatct ctactaaaaa tacgaaaaaa      4020
ttagctgggc atggtggcgc acacctgtag tcccagctac tccggaggct gaggcaggag      4080
aatctcttga acctgggagg cggaggttgc aatgagccga gatcacgtca ctgcactcca      4140
gcttgggcaa cagagcaaga ctccatctca aaaaagaaaa aagaaaagaa atagaattat      4200
caagctttta aaaactagag cacagaagga ataaggtcat gaaatttaaa aggttaaata      4260
ttgtcatagg attaagcagt ttaaagattg ttggatgaaa ttatttgtca ttcattcaag      4320
taataaatat ttaatgaata cttgctataa aaaaaaaaaa aaaaaaaaa aaaa            4374
```

Each reference cited herein is hereby incorporated by reference in its entirety.

---

We claim:

1. A method for making a hypermutable plant or yeast cell in vitro comprising exposing a plant cell or yeast cell to an inhibitor of mismatch repair, thereby rendering said cell hypermutable, wherein said inhibitor is an anthracene, wherein said anthracene has the formula:

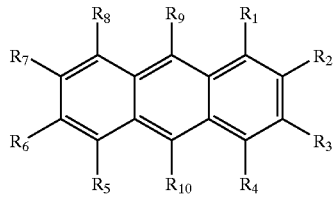

wherein $R_1$–$R_{10}$ are independently hydrogen, hydroxyl, amino group, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;

wherein said heteroaryl, and substituted heteroaryl contain at least one heteroatom that is oxygen, sulfur, a metal atom, phosphorus, silicon or nitrogen; and wherein said substituents of the substituted alkyl, substituted alkenyl, substituted alkynyl, substituted aryl, and substituted heteroaryl are halogen, CN, $NO_2$, lower alkyl, aryl, heteroaryl, aralkyl, aralkyloxy, guanidino, alkoxycarbonyl, alkoxy, hydroxy, carboxy or amino group; and wherein said amino group is optionally substituted with an acyl group, or 1 to 3 aryl or lower alkyl groups.

2. The method of claim 1 wherein $R_5$ and $R_6$ are hydrogen.

3. The method of claim 1 wherein $R_1$–$R_{10}$ are independently hydrogen, hydroxyl, alkyl, aryl, arylalkyl, or hydroxyalkyl.

4. The method of claim 1 wherein $R_1$–$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl.

5. The method of claim 1 wherein said anthracene is selected from the group consisting of 1,2-dimethylanthracene, 9,10-dimethyl anthracene, 7,8-dimethylanthracene, 9,10-diphenylanthracene, 9,10-dihydroxymethylanthracene, 9-hydroxymethyl-10-methylanthracene, dimethylanthracene-1,2-diol, 9-hydroxymethyl-10-methylanthracene-1,2-diol, 9-hydroxymethyl-10-methylanthracene-3,4-diol, and 9,10-di-m-tolyanthracene.

6. The method of claim 1 wherein $R_3$, $R_4$, $R_5$, $R_6$, $R_7$, $R_8$, $R_9$ and $R_{10}$ are hydrogen.

7. The method of claim 1 wherein $R_1$, $R_2$, $R_3$, $R_4$, $R_5$, $R_6$, $R_7$ and $R_8$ are hydrogen.

8. The method of claim 1 wherein $R_3$, $R_4$, $R_5$, $R_6$, $R_7$ and $R_8$ are hydrogen.

9. The method of claim 1 wherein $R_1$, $R_2$, $R_3$, $R_4$, $R_5$, $R_6$, $R_9$ and $R_{10}$ are hydrogen.

10. The method of claim 1 wherein $R_1$, $R_2$, $R_5$, $R_6$, $R_7$ and $R_8$ are hydrogen.

11. The method of claim 1 wherein $R_1$, $R_2$, $R_3$, $R_4$, $R_5$, $R_6$, $R_7$, $R_8$ and $R_{10}$ are hydrogen.

12. The method of claim 1 wherein said inhibitor of mismatch repair is introduced into a growth medium of a plant.

13. A method for generating a mutation in a gene of interest comprising exposing a plant cell or yeast cell comprising said gene of interest to a chemical mismatch repair inhibitor in vitro to generate a hypermutable cell, wherein said mismatch repair inhibitor is an anthracene having the formula:

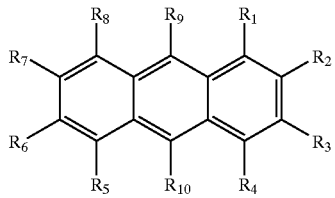

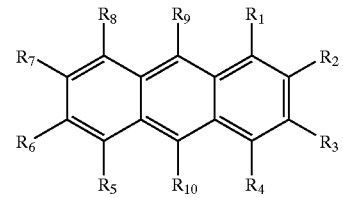

wherein $R_1$–$R_{10}$ are independently hydrogen, hydroxyl, amino group, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;

wherein said heteroaryl, and substituted heteroaryl contain at least one heteroatom that is oxygen, sulfur, a metal atom, phosphorus, silicon or nitrogen; and wherein said substituents of the substituted alkyl, substituted alkenyl, substituted alkynyl, substituted aryl, and substituted heteroaryl are halogen, CN, $NO_2$, lower alkyl, aryl, heteroaryl, aralkyl, aralkyloxy, guanidino, alkoxycarbonyl, alkoxy, hydroxy, carboxy or amino group;

and wherein said amino group is optionally substituted with an acyl group, or 1 to 3 aryl or lower alkyl groups;

testing said hypermutable cell to determine whether said gene of interest comprises a mutation; and removing the chemical inhibitor of mismatch repair.

14. The method of claim 13 wherein said testing comprises analyzing a polynucleotide sequence of said gene of interest.

15. The method of claim 13 wherein said testing comprises analyzing the phenotype of said plant cell or yeast cell.

16. The method of claim 13 further comprising exposing said cell to a mutagen.

17. The method of claim 16 wherein said mutagen is selected from the group consisting of N-methyl-N'-nitro-N-nitrosoguanidine, methane sulfonate, dimethyl sulfonate, O-6-methyl benzadine, ethyl methanesulfonate, methylnitrosourea, and ethylnitrosourea.

18. A method for making a hypermutable plant comprising exposing at least one cell of said plant to an inhibitor of mismatch repair, thereby rendering said cell hypermutable, wherein said inhibitor is an anthracene, wherein said anthracene has the formula:

wherein $R_1$–$R_{10}$ are independently hydrogen, hydroxyl, amino group, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;

wherein said heteroaryl, and substituted heteroaryl contain at least one heteroatom that, is oxygen, sulfur, a metal atom, phosphorus, silicon or nitrogen; and wherein said substituents of the substituted alkyl, substituted alkenyl, substituted alkynyl, substituted aryl, and substituted heteroaryl are halogen, CN, $NO_2$, lower alkyl, aryl, heteroaryl, aralkyl, aralkyloxy, guanidino, alkoxycarbonyl, alkoxy, hydroxy, carboxy or amino group; and wherein said amino group is optionally substituted with an acyl group, or 1 to 3 aryl or lower alkyl groups.

19. The method of claim 18 wherein $R_5$ and $R_6$ are hydrogen.

20. The method of claim 18 wherein $R_1$–$R_{10}$ are independently hydrogen, hydroxyl, alkyl, aryl, arylalkyl, or hydroxyalkyl.

21. The method of claim 18 wherein $R_1$–$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl.

22. The method of claim 18 wherein said anthracene is selected from the group consisting of 1,2-dimethylanthracene, 9,10-dimethyl anthracene, 7,8-dimethylanthracene, 9,10-diphenylanthracene, 9,10-dihydroxymethylanthracene, 9-hydroxymethyl-10-methylanthracene, dimethylanthracene-1,2-diol, 9-hydroxymethyl-10-methylanthracene-1,2-diol, 9-hydroxymethyl-10-methylanthracene-3,4-diol, and 9,10-di-m-tolyanthracene.

23. The method of claim 18 wherein $R_3$, $R_4$, $R_5$, $R_6$, $R_7$, $R_8$, $R_9$ and $R_{10}$ are hydrogen.

24. The method of claim 18 wherein $R_1$, $R_2$, $R_3$, $R_4$, $R_5$, $R_6$, $R_7$ and $R_8$ are hydrogen.

25. The method of claim 18 wherein $R_3$, $R_4$, $R_5$, $R_6$, $R_7$ and $R_8$ are hydrogen.

26. The method of claim 18 wherein $R_1$, $R_2$, $R_3$, $R_4$, $R_5$, $R_6$, $R_9$ and $R_{10}$ are hydrogen.

27. The method of claim 18 wherein $R_1$, $R_2$, $R_5$, $R_6$, $R_7$ and $R_8$ are hydrogen.

28. The method of claim 18 wherein $R_1$, $R_2$, $R_3$, $R_4$, $R_5$, $R_6$, $R_7$, $R_8$ and $R_{10}$ are hydrogen.

29. The method of claim 18 wherein said testing comprises analyzing a polynucleotide sequence of said gene of interest.

* * * * *

UNITED STATES PATENT AND TRADEMARK OFFICE
CERTIFICATE OF CORRECTION

PATENT NO. : 6,982,169 B2
APPLICATION NO. : 09/760285
DATED : January 3, 2006
INVENTOR(S) : Nicholas C. Nicolaides et al.

It is certified that error appears in the above-identified patent and that said Letters Patent is hereby corrected as shown below:

Title Page,
Item (56), References Cited,

OTHER PUBLICATIONS:
"Ngo et al." reference, delete "490-495-1994." and insert -- 490-495 1994. --.
"Kotiloglu E." reference, delete "carcinogencity" and insert -- carcinogenicity --.
"Shelton et al." reference, delete "laci" and insert -- lacI --.
"Dobrovolsky et al." reference, delete "Ik gene" and insert -- Tk gene --.
"Cascalho M, et al." reference, delete " hpermutation", " and insert --hypermutation", --,
"Vora, K.A., et al.," reference, delete "celll" and insert -- cell --.
"Nicolaides, N.C.," reference, delete "nutator" and insert -- mutator --.
"Ma et al.," reference, delete "Mismtach" and insert -- Mismatch --.

Column 2,
Line 15, delete "for".

Column 4
Line 7, delete "5 mls" and insert -- 50 mls --.

Column 5,
Line 21, delete "If-GUS" and insert -- IF-GUS --.

Column 6,
Line 43, after "may" insert -- be --.

Column 9,
Line 47, delete "16:4467-4416;" and insert -- 16:4467-4476; --.
Line 48, delete "39-3176-3183)." and insert -- 39:3176-3183). --.

Column 10,
Line 18, delete "an" and insert -- a --.

Column 11
Line 9, delete "some" and insert -- same --.
Line 46, delete "M reporter" and insert -- MMR reporter --.

Column 12
Line 12, delete "polynuclotides" and insert -- polynucleotides --.

UNITED STATES PATENT AND TRADEMARK OFFICE
CERTIFICATE OF CORRECTION

PATENT NO. : 6,982,169 B2
APPLICATION NO. : 09/760285
DATED : January 3, 2006
INVENTOR(S) : Nicholas C. Nicolaides et al.

It is certified that error appears in the above-identified patent and that said Letters Patent is hereby corrected as shown below:

Column 15,
Line 14, delete "O-galactosidase" and insert -- β-galactosidase.--.
Line 35, delete "resistance-gene" and insert -- resistance gene --.

Column 16,
Line 63, delete "speific" and insert -- specific --.

Column 25,
Line 47, delete "consitutively" and insert -- constitutively --.
Line 58, delete "On" and insert -- One --.

Column 27,
Line 59, delete "exonulcease" and insert -- exonuclease --.

Column 124,
Line 25, delete "that," and insert -- that --.

Signed and Sealed this

Twenty-sixth Day of June, 2007

JON W. DUDAS
*Director of the United States Patent and Trademark Office*

SEQUENCE LISTING

<160> NUMBER OF SEQ ID NOS: 44

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 1
ggatcctaat acgactcact atagggagac caccatgtcg ttcgtggcag gg            52

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 2
taagtcttaa gtgctaccaa c                                              21

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 3
ggatcctaat acgactcact atagggagac caccatggaa caattgcctg cgg           53

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:

-continued oligonucleotide primer

<400> SEQUENCE: 4
aggttagtga agactctgtc                                                    20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 5
ctgatctcac ggacaatagt gc                                                 22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 6
ggctccataa aaagtgcacc                                                    20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 7
ggtctgttga tgtcgtaagt cg                                                 22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8
atcttgaaac ctttagggag gg                                                 22

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 9
agaagtttag acaggtac                                                      18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

```
<400> SEQUENCE: 10
aaatgtgcaa ttgccttc                                                    18

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 11
cccggatcca tgttaaaaaa aaaaaaaaaa aaaaaacgtc ctgtagaaac c                51

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 12
cccggatcca tgttaaaaaa aaaaaaaaaa aaaacgtcct gtagaaac                   48

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 13
cccgaattcc ccgatctagt aacatagatg                                       30

<210> SEQ ID NO 14
<211> LENGTH: 859
<212> TYPE: PRT
<213> ORGANISM: Mus musculus

<400> SEQUENCE: 14

Met Glu Gln Thr Glu Gly Val Ser Thr Glu Cys Ala Lys Ala Ile Lys
  1               5                  10                  15

Pro Ile Asp Gly Lys Ser Val His Gln Ile Cys Ser Gly Gln Val Ile
                 20                  25                  30

Leu Ser Leu Ser Thr Ala Val Lys Glu Leu Ile Glu Asn Ser Val Asp
             35                  40                  45

Ala Gly Ala Thr Thr Ile Asp Leu Arg Leu Lys Asp Tyr Gly Val Asp
         50                  55                  60

Leu Ile Glu Val Ser Asp Asn Gly Cys Gly Val Glu Glu Glu Asn Phe
 65                  70                  75                  80

Glu Gly Leu Ala Leu Lys His His Thr Ser Lys Ile Gln Glu Phe Ala
                 85                  90                  95

Asp Leu Thr Gln Val Glu Thr Phe Gly Phe Arg Gly Glu Ala Leu Ser
                100                 105                 110

Ser Leu Cys Ala Leu Ser Asp Val Thr Ile Ser Thr Cys His Gly Ser
            115                 120                 125

Ala Ser Val Gly Thr Arg Leu Val Phe Asp His Asn Gly Lys Ile Thr
        130                 135                 140
```

-continued

```
Gln Lys Thr Pro Tyr Pro Arg Pro Lys Gly Thr Val Ser Val Gln
145                 150                 155                 160

His Leu Phe Tyr Thr Leu Pro Val Arg Tyr Lys Glu Phe Gln Arg Asn
                165                 170                 175

Ile Lys Lys Glu Tyr Ser Lys Met Val Gln Val Leu Gln Ala Tyr Cys
            180                 185                 190

Ile Ile Ser Ala Gly Val Arg Val Ser Cys Thr Asn Gln Leu Gly Gln
        195                 200                 205

Gly Lys Arg His Ala Val Val Cys Thr Ser Gly Thr Ser Gly Met Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ala Val Cys Glu Glu Tyr Gly
                245                 250                 255

Leu Ser Thr Ser Gly Arg His Lys Thr Phe Ser Thr Phe Arg Ala Ser
                260                 265                 270

Phe His Ser Ala Arg Thr Ala Pro Gly Gly Val Gln Gln Thr Gly Ser
            275                 280                 285

Phe Ser Ser Ile Arg Gly Pro Val Thr Gln Gln Arg Ser Leu Ser
        290                 295                 300

Leu Ser Met Arg Phe Tyr His Met Tyr Asn Arg His Gln Tyr Pro Phe
305                 310                 315                 320

Val Val Leu Asn Val Ser Val Asp Ser Glu Cys Val Asp Ile Asn Val
                325                 330                 335

Thr Pro Asp Lys Arg Gln Ile Leu Leu Gln Glu Glu Lys Leu Leu Leu
                340                 345                 350

Ala Val Leu Lys Thr Ser Leu Ile Gly Met Phe Asp Ser Asp Ala Asn
            355                 360                 365

Lys Leu Asn Val Asn Gln Gln Pro Leu Leu Asp Val Glu Gly Asn Leu
        370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
                420                 425                 430

Ile Lys Ser Arg Gly Pro Glu Thr Ala Glu Leu Thr Arg Ser Phe Pro
            435                 440                 445

Ser Glu Lys Arg Gly Val Leu Ser Ser Tyr Pro Ser Asp Val Ile Ser
        450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
                485                 490                 495

Leu Ser Ser Thr Ser Ala Gly Ser Glu Glu Phe Ser Thr Pro Glu
                500                 505                 510

Val Ala Ser Ser Phe Ser Ser Asp Tyr Asn Val Ser Ser Leu Glu Asp
            515                 520                 525

Arg Pro Ser Gln Glu Thr Ile Asn Cys Gly Asp Leu Asp Cys Arg Pro
        530                 535                 540

Pro Gly Thr Gly Gln Ser Leu Lys Pro Glu Asp His Gly Tyr Gln Cys
545                 550                 555                 560

Lys Ala Leu Pro Leu Ala Arg Leu Ser Pro Thr Asn Ala Lys Arg Phe
```

```
                565             570             575
Lys Thr Glu Glu Arg Pro Ser Asn Val Asn Ile Ser Gln Arg Leu Pro
            580             585             590
Gly Pro Gln Ser Thr Ser Ala Ala Glu Val Asp Val Ala Ile Lys Met
        595             600             605
Asn Lys Arg Ile Val Leu Leu Glu Phe Ser Leu Ser Ser Leu Ala Lys
    610             615             620
Arg Met Lys Gln Leu Gln His Leu Lys Ala Gln Asn Lys His Glu Leu
625             630             635             640
Ser Tyr Arg Lys Phe Arg Ala Lys Ile Cys Pro Gly Glu Asn Gln Ala
            645             650             655
Ala Glu Asp Glu Leu Arg Lys Glu Ile Ser Lys Ser Met Phe Ala Glu
        660             665             670
Met Glu Ile Leu Gly Gln Phe Asn Leu Gly Phe Ile Val Thr Lys Leu
    675             680             685
Lys Glu Asp Leu Phe Leu Val Asp Gln His Ala Ala Asp Glu Lys Tyr
690             695             700
Asn Phe Glu Met Leu Gln Gln His Thr Val Leu Gln Ala Gln Arg Leu
705             710             715             720
Ile Thr Pro Gln Thr Leu Asn Leu Thr Ala Val Asn Glu Ala Val Leu
            725             730             735
Ile Glu Asn Leu Glu Ile Phe Arg Lys Asn Gly Phe Asp Phe Val Ile
        740             745             750
Asp Glu Asp Ala Pro Val Thr Glu Arg Ala Lys Leu Ile Ser Leu Pro
    755             760             765
Thr Ser Lys Asn Trp Thr Phe Gly Pro Gln Asp Ile Asp Glu Leu Ile
770             775             780
Phe Met Leu Ser Asp Ser Pro Gly Val Met Cys Arg Pro Ser Arg Val
785             790             795             800
Arg Gln Met Phe Ala Ser Arg Ala Cys Arg Lys Ser Val Met Ile Gly
            805             810             815
Thr Ala Leu Asn Ala Ser Glu Met Lys Lys Leu Ile Thr His Met Gly
        820             825             830
Glu Met Asp His Pro Trp Asn Cys Pro His Gly Arg Pro Thr Met Arg
    835             840             845
His Val Ala Asn Leu Asp Val Ile Ser Gln Asn
850             855

<210> SEQ ID NO 15
<211> LENGTH: 3056
<212> TYPE: DNA
<213> ORGANISM: Mus musculus

<400> SEQUENCE: 15
gaattccggt gaaggtcctg aagaatttcc agattcctga gtatcattgg aggagacaga    60
taacctgtcg tcaggtaacg atggtgtata tgcaacagaa atgggtgttc ctggagacgc   120
gtcttttccc gagagcggca ccgcaactct cccgcggtga ctgtgactgg aggagtcctg   180
catccatgga gcaaaccgaa ggcgtgagta cagaatgtgc taaggccatc aagcctattg   240
atgggaagtc agtccatcaa atttgttctg gcaggtgat actcagttta agcaccgctg   300
tgaaggagtt gatagaaaat agtgtagatg ctggtgctac tactattgat ctaaggctta   360
aagactatgg ggtggacctc attgaagttt cagacaatgg atgtgggta gaagaagaaa   420 actttgaagg tctagctctg aaacatcaca catctaagat tcaagagttt gccgacctca   480
```

-continued

```
cgcaggttga aactttcggc tttcgggggg aagctctgag ctctctgtgt gcactaagtg      540
atgtcactat atctacctgc cacgggtctg caagcgttgg gactcgactg gtgtttgacc      600
ataatgggaa aatcacccag aaaactccct acccccgacc taaaggaacc acagtcagtg      660
tgcagcactt attttataca ctacccgtgc gttacaaaga gtttcagagg aacattaaaa      720
aggagtattc caaaatggtg caggtcttac aggcgtactg tatcatctca gcaggcgtcc      780
gtgtaagctg cactaatcag ctcggacagg ggaagcggca cgctgtggtg tgcacaagcg      840
gcacgtctgg catgaaggaa aatatcgggt ctgtgtttgg ccagaagcag ttgcaaagcc      900
tcattccttt tgttcagctg cccccctagtg acgctgtgtg tgaagagtac ggcctgagca      960
cttcaggacg ccacaaaacc ttttctacgt ttcgggcttc atttcacagt gcacgcacgg     1020
cgccgggagg agtgcaacag acaggcagtt tttcttcatc aatcagaggc cctgtgaccc     1080
agcaaaggtc tctaagcttg tcaatgaggt tttatcacat gtataaccgg catcagtacc     1140
catttgtcgt ccttaacgtt tccgttgact cagaatgtgt ggatattaat gtaactccag     1200
ataaaaggca aattctacta caagaagaga agctattgct ggccgtttta aagacctcct     1260
tgataggaat gtttgacagt gatgcaaaca agcttaatgt caaccagcag ccactgctag     1320
atgttgaagg taacttagta aagctgcata ctgcagaact agaaaagcct gtgccaggaa     1380
agcaagataa ctctccttca ctgaagagca cagcagacga gaaaagggta gcatccatct     1440
ccaggctgag agaggccttt tctcttcatc ctactaaaga gatcaagtct aggggtccag     1500
agactgctga actgacacgg agttttccaa gtgagaaaag gggcgtgtta tcctcttatc     1560
cttcagacgt catctcttac agaggcctcc gtggctcgca ggacaaattg gtgagtccca     1620
cggacagccc tggtgactgt atggacagag agaaaataga aaaagactca gggctcagca     1680
gcacctcagc tggctctgag gaagagttca gcaccccaga gtggccagt agctttagca     1740
gtgactataa cgtgagctcc ctagaagaca gaccttctca ggaaaccata aactgtggtg     1800
acctggactg ccgtcctcca ggtacaggac agtccttgaa gccagaagac catggatatc     1860
aatgcaaagc tctacctcta gctcgtctgt caccacaaaa tgccaagcgc ttcaagacag     1920
aggaaagacc ctcaaatgtc aacatttctc aaagattgcc tggtcctcag agcacctcag     1980
cagctgaggt cgatgtagcc ataaaaatga ataagagaat cgtgctcctc gagttctctc     2040
tgagttctct agctaagcga atgaagcagt tacagcacct aaaggcgcag aacaaacatg     2100
aactgagtta cagaaaattt agggccaaga tttgccctgg agaaaaccaa gcagcagaag     2160
atgaactcag aaaagagatt agtaaatcga tgtttgcaga gatggagatc ttgggtcagt     2220
ttaacctggg atttatagta accaaactga agaggacct cttcctggtg gaccagcatg     2280
ctgcggatga aagtacaac tttgagatgc tgcagcagca cacggtgctc caggcgcaga     2340
ggctcatcac accccagact ctgaacttaa ctgctgtcaa tgaagctgta ctgatagaaa     2400
atctggaaat attcagaaag aatggctttg actttgtcat tgatgaggat gctccagtca     2460
ctgaaagggc taaattgatt tccttaccaa ctagtaaaaa ctggaccttt ggaccccaag     2520
atatagatga actgatcttt atgttaagtg acagccctgg ggtcatgtgc cggccctcac     2580
gagtcagaca gatgtttgct tccagagcct gtcggaagtc agtgatgatt ggaacgcgc      2640
tcaatgcgag cgagatgaag aagctcatca cccacatggg tgagatggac cacccctgga     2700
actgccccca cggcaggcca accatgagge acgttgccaa tctggatgtc atctctcaga     2760
actgacacac cccttgtagc atagagttta ttacagattg ttcggtttgc aaagagaagg     2820
```

-continued

```
ttttaagtaa tctgattatc gttgtacaaa aattagcatg ctgctttaat gtactggatc    2880
catttaaaag cagtgttaag gcaggcatga tggagtgttc ctctagctca gctacttggg    2940
tgatccggtg ggagctcatg tgagcccagg actttgagac cactccgagc cacattcatg    3000
agactcaatt caaggacaaa aaaaaaaaga tattttttgaa gcctttttaaa aaaaa        3056
```

<210> SEQ ID NO 16
<211> LENGTH: 862
<212> TYPE: PRT
<213> ORGANISM: Homo sapiens

<400> SEQUENCE: 16

```
Met Glu Arg Ala Glu Ser Ser Thr Glu Pro Ala Lys Ala Ile Lys
 1               5                  10                  15

Pro Ile Asp Arg Lys Ser Val His Gln Ile Cys Ser Gly Gln Val Val
                20                  25                  30

Leu Ser Leu Ser Thr Ala Val Lys Glu Leu Val Glu Asn Ser Leu Asp
            35                  40                  45

Ala Gly Ala Thr Asn Ile Asp Leu Lys Leu Lys Asp Tyr Gly Val Asp
        50                  55                  60

Leu Ile Glu Val Ser Asp Asn Gly Cys Gly Val Glu Glu Asn Phe
 65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr Arg Leu Met Phe Asp His Asn Gly Lys Ile Ile
    130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205

Gly Lys Arg Gln Pro Val Val Cys Thr Gly Gly Ser Pro Ser Ile Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
            260                 265                 270

Ile Ser Gln Cys Thr His Gly Val Gly Arg Ser Ser Thr Asp Arg Gln
        275                 280                 285

Phe Phe Phe Ile Asn Arg Arg Pro Cys Asp Pro Ala Lys Val Cys Arg
    290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335
```

-continued

```
Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Val Asn
            355                 360                 365

Lys Leu Asn Val Ser Gln Pro Leu Leu Asp Val Glu Gly Asn Leu
            370                 375                 380

Ile Lys Met His Ala Ala Asp Leu Glu Lys Pro Met Val Glu Lys Gln
385                 390                 395                 400

Asp Gln Ser Pro Ser Leu Arg Thr Gly Glu Glu Lys Lys Asp Val Ser
                405                 410                 415

Ile Ser Arg Leu Arg Glu Ala Phe Ser Leu Arg His Thr Thr Glu Asn
                420                 425                 430

Lys Pro His Ser Pro Lys Thr Pro Glu Pro Arg Arg Ser Pro Leu Gly
            435                 440                 445

Gln Lys Arg Gly Met Leu Ser Ser Ser Thr Ser Gly Ala Ile Ser Asp
            450                 455                 460

Lys Gly Val Leu Arg Pro Gln Lys Glu Ala Val Ser Ser Ser His Gly
465                 470                 475                 480

Pro Ser Asp Pro Thr Asp Arg Ala Glu Val Glu Lys Asp Ser Gly His
                485                 490                 495

Gly Ser Thr Ser Val Asp Ser Glu Gly Phe Ser Ile Pro Asp Thr Gly
                500                 505                 510

Ser His Cys Ser Ser Glu Tyr Ala Ala Ser Ser Pro Gly Asp Arg Gly
            515                 520                 525

Ser Gln Glu His Val Asp Ser Gln Glu Lys Ala Pro Glu Thr Asp Asp
            530                 535                 540

Ser Phe Ser Asp Val Asp Cys His Ser Asn Gln Glu Asp Thr Gly Cys
545                 550                 555                 560

Lys Phe Arg Val Leu Pro Gln Pro Thr Asn Leu Ala Thr Pro Asn Thr
                565                 570                 575

Lys Arg Phe Lys Lys Glu Glu Ile Leu Ser Ser Ser Asp Ile Cys Gln
                580                 585                 590

Lys Leu Val Asn Thr Gln Asp Met Ser Ala Ser Gln Val Asp Val Ala
            595                 600                 605

Val Lys Ile Asn Lys Lys Val Val Pro Leu Asp Phe Ser Met Ser Ser
            610                 615                 620

Leu Ala Lys Arg Ile Lys Gln Leu His His Glu Ala Gln Gln Ser Glu
625                 630                 635                 640

Gly Glu Gln Asn Tyr Arg Lys Phe Arg Ala Lys Ile Cys Pro Gly Glu
                645                 650                 655

Asn Gln Ala Ala Glu Asp Glu Leu Arg Lys Glu Ile Ser Lys Thr Met
            660                 665                 670

Phe Ala Glu Met Glu Ile Ile Gly Gln Phe Asn Leu Gly Phe Ile Ile
            675                 680                 685

Thr Lys Leu Asn Glu Asp Ile Phe Ile Val Asp Gln His Ala Thr Asp
            690                 695                 700

Glu Lys Tyr Asn Phe Glu Met Leu Gln Gln His Thr Val Leu Gln Gly
705                 710                 715                 720

Gln Arg Leu Ile Ala Pro Gln Thr Leu Asn Leu Thr Ala Val Asn Glu
                725                 730                 735

Ala Val Leu Ile Glu Asn Leu Glu Ile Phe Arg Lys Asn Gly Phe Asp
            740                 745                 750

Phe Val Ile Asp Glu Asn Ala Pro Val Thr Glu Arg Ala Lys Leu Ile
```

```
            755                 760                 765
Ser Leu Pro Thr Ser Lys Asn Trp Thr Phe Gly Pro Gln Asp Val Asp
    770                 775                 780

Glu Leu Ile Phe Met Leu Ser Asp Ser Pro Gly Val Met Cys Arg Pro
785                 790                 795                 800

Ser Arg Val Lys Gln Met Phe Ala Ser Arg Ala Cys Arg Lys Ser Val
                805                 810                 815

Met Ile Gly Thr Ala Leu Asn Thr Ser Glu Met Lys Lys Leu Ile Thr
            820                 825                 830

His Met Gly Glu Met Asp His Pro Trp Asn Cys Pro His Gly Arg Pro
                835                 840                 845

Thr Met Arg His Ile Ala Asn Leu Gly Val Ile Ser Gln Asn
    850                 855                 860

<210> SEQ ID NO 17
<211> LENGTH: 2771
<212> TYPE: DNA
<213> ORGANISM: Homo sapiens

<400> SEQUENCE: 17
cgaggcggat cgggtgttgc atccatggag cgagctgaga gctcgagtac agaacctgct      60
aaggccatca aacctattga tcggaagtca gtccatcaga tttgctctgg caggtggta     120
ctgagtctaa gcactgcggt aaaggagtta gtagaaaaca gtctggatgc tggtgccact     180
aatattgatc taaagcttaa ggactatgga gtggatctta ttgaagtttc agacaatgga     240
tgtgggtag aagaagaaaa cttcgaaggc ttaactctga acatcacac atctaagatt     300
caagagtttg ccgacctaac tcaggttgaa acttttggct tcggggggga agctctgagc     360
tcactttgtg cactgagcga tgtcaccatt tctacctgcc acgcatcggc gaaggttgga     420
actcgactga tgttttgatca caatgggaaa attatccaga aaaccccta ccccccgcccc     480
agagggacca cagtcagcgt gcagcagtta ttttccacac tacctgtgcg ccataaggaa     540
tttcaaagga atattaagaa ggagtatgcc aaaatggtcc aggtcttaca tgcatactgt     600
atcatttcag caggcatccg tgtaagttgc accaatcagc ttggacaagg aaaacgacag     660
cctgtggtat gcacaggtgg aagccccagc ataaaggaaa atatcggctc tgtgtttggg     720
cagaagcagt tgcaaagcct cattccttt gttcagctgc ccctagtga ctccgtgtgt     780
gaagagtacg gtttgagctg ttcggatgct ctgcataatc tttttttacat ctcaggtttc     840
atttcacaat gcacgcatgg agttggaagg agttcaacag acagacagtt tttctttatc     900
aaccggcggc cttgtgaccc agcaaaggtc tgcagactcg tgaatgaggt ctaccacatg     960
tataatcgac accagtatcc atttgttgtt cttaacattt ctgttgattc agaatgcgtt    1020
gatatcaatg ttactccaga taaaaggcaa attttgctac aagaggaaaa gcttttgttg    1080
gcagttttaa agacctcttt gataggaatg tttgatagtg atgtcaacaa gctaaatgtc    1140
agtcagcagc cactgctgga tgttgaaggt aacttaataa aaatgcatgc agcggatttg    1200
gaaaagccca tggtagaaaa gcaggatcaa tccccttcat taaggactgg agaagaaaaa    1260
aaagacgtgt ccattttccag actgcgagag gccttttctc ttcgtcacac aacagagaac    1320
aagcctcaca gcccaaagac tccagaacca agaggagcc ctctaggaca gaaaggggt    1380
atgctgtctt ctagcacttc aggtgccatc tctgacaaag gcgtcctgag acctcagaaa    1440
gaggcagtga gttccagtca cggacccagt gaccctacgg acagagcgga ggtgagaag    1500
gactcggggc acggcagcac ttccgtggat tctgagggt tcagcatccc agacacgggc    1560
```

-continued

```
agtcactgca gcagcgagta tgcggccagc tccccagggg acaggggctc gcaggaacat   1620
gtggactctc aggagaaagc gcctgaaact gacgactctt tttcagatgt ggactgccat   1680
tcaaaccagg aagataccgg atgtaaattt cgagttttgc ctcagccaac taatctcgca   1740
accccaaaca caaagcgttt taaaaaagaa gaaattcttt ccagttctga catttgtcaa   1800
aagttagtaa atactcagga catgtcagcc tctcaggttg atgtagctgt gaaaattaat   1860
aagaaagttg tgcccctgga cttttctatg agttctttag ctaaacgaat aaagcagtta   1920
catcatgaag cacagcaaag tgaaggggaa cagaattaca ggaagtttag ggcaaagatt   1980
tgtcctggag aaaatcaagc agccgaagat gaactaagaa aagagataag taaaacgatg   2040
tttgcagaaa tggaaatcat tggtcagttt aacctgggat ttataataac caaactgaat   2100
gaggatatct tcatagtgga ccagcatgcc acggacgaga agtataactt cgagatgctg   2160
cagcagcaca ccgtgctcca ggggcagagg ctcatagcac ctcagactct caacttaact   2220
gctgttaatg aagctgttct gatagaaaat ctggaaatat ttagaaagaa tggctttgat   2280
tttgttatcg atgaaaatgc tccagtcact gaaagggcta aactgatttc cttgccaact   2340
agtaaaaact ggaccttcgg accccaggac gtcgatgaac tgatcttcat gctgagcgac   2400
agccctgggg tcatgtgccg gccttcccga gtcaagcaga tgtttgcctc cagagcctgc   2460
cggaagtcgg tgatgattgg gactgctctt aacacaagcg agatgaagaa actgatcacc   2520
cacatggggg agatggacca cccctggaac tgtccccatg gaaggccaac catgagacac   2580
atcgccaacc tgggtgtcat ttctcagaac tgaccgtagt cactgtatgg aataattggt   2640
tttatcgcag attttatgt tttgaaagac agagtcttca ctaaccttt ttgttttaaa    2700 atgaaacctg ctacttaaaa aaatacaca tcacacccat ttaaaagtga tcttgagaac   2760
cttttcaaac c                                                       2771
```

<210> SEQ ID NO 18
<211> LENGTH: 932
<212> TYPE: PRT
<213> ORGANISM: Homo sapiens

<400> SEQUENCE: 18

```
Met Lys Gln Leu Pro Ala Ala Thr Val Arg Leu Leu Ser Ser Ser Gln
 1               5                  10                  15

Ile Ile Thr Ser Val Ser Val Val Lys Glu Leu Ile Glu Asn Ser
             20                  25                  30

Leu Asp Ala Gly Ala Thr Ser Val Asp Val Lys Leu Glu Asn Tyr Gly
         35                  40                  45

Phe Asp Lys Ile Glu Val Arg Asp Asn Gly Glu Gly Ile Lys Ala Val
     50                  55                  60

Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
                 85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys Pro Ser His Leu Gly Gln Gly Thr Thr Val Thr
    130                 135                 140

Ala Leu Arg Leu Phe Lys Asn Leu Pro Val Arg Lys Gln Phe Tyr Ser
```

-continued

```
            145                 150                 155                 160
Thr Ala Lys Lys Cys Lys Asp Glu Ile Lys Lys Ile Gln Asp Leu Leu
                165                 170                 175
Met Ser Phe Gly Ile Leu Lys Pro Asp Leu Arg Ile Val Phe Val His
            180                 185                 190
Asn Lys Ala Val Ile Trp Gln Lys Ser Arg Val Ser Asp His Lys Met
        195                 200                 205
Ala Leu Met Ser Val Leu Gly Thr Ala Val Met Asn Asn Met Glu Ser
    210                 215                 220
Phe Gln Tyr His Ser Glu Glu Ser Gln Ile Tyr Leu Ser Gly Phe Leu
225                 230                 235                 240
Pro Lys Cys Asp Ala Asp His Ser Phe Thr Ser Leu Ser Thr Pro Glu
                245                 250                 255
Arg Ser Phe Ile Phe Ile Asn Ser Arg Pro Val His Gln Lys Asp Ile
                260                 265                 270
Leu Lys Leu Ile Arg His His Tyr Asn Leu Lys Cys Leu Lys Glu Ser
            275                 280                 285
Thr Arg Leu Tyr Pro Val Phe Phe Leu Lys Ile Asp Val Pro Thr Ala
        290                 295                 300
Asp Val Asp Val Asn Leu Thr Pro Asp Lys Ser Gln Val Leu Leu Gln
305                 310                 315                 320
Asn Lys Glu Ser Val Leu Ile Ala Leu Glu Asn Leu Met Thr Thr Cys
                325                 330                 335
Tyr Gly Pro Leu Pro Ser Thr Asn Ser Tyr Glu Asn Asn Lys Thr Asp
                340                 345                 350
Val Ser Ala Ala Asp Ile Val Leu Ser Lys Thr Ala Glu Thr Asp Val
            355                 360                 365
Leu Phe Asn Lys Val Glu Ser Ser Gly Lys Asn Tyr Ser Asn Val Asp
        370                 375                 380
Thr Ser Val Ile Pro Phe Gln Asn Asp Met His Asn Asp Glu Ser Gly
385                 390                 395                 400
Lys Asn Thr Asp Asp Cys Leu Asn His Gln Ile Ser Ile Gly Asp Phe
                405                 410                 415
Gly Tyr Gly His Cys Ser Ser Glu Ile Ser Asn Ile Asp Lys Asn Thr
                420                 425                 430
Lys Asn Ala Phe Gln Asp Ile Ser Met Ser Asn Val Ser Trp Glu Asn
            435                 440                 445
Ser Gln Thr Glu Tyr Ser Lys Thr Cys Phe Ile Ser Ser Val Lys His
        450                 455                 460
Thr Gln Ser Glu Asn Gly Asn Lys Asp His Ile Asp Glu Ser Gly Glu
465                 470                 475                 480
Asn Glu Glu Glu Ala Gly Leu Glu Asn Ser Ser Glu Ile Ser Ala Asp
                485                 490                 495
Glu Trp Ser Arg Gly Asn Ile Leu Lys Asn Ser Val Gly Glu Asn Ile
            500                 505                 510
Glu Pro Val Lys Ile Leu Val Pro Glu Lys Ser Leu Pro Cys Lys Val
        515                 520                 525
Ser Asn Asn Asn Tyr Pro Ile Pro Glu Gln Met Asn Leu Asn Glu Asp
    530                 535                 540
Ser Cys Asn Lys Lys Ser Asn Val Ile Asp Asn Lys Ser Gly Lys Val
545                 550                 555                 560
Thr Ala Tyr Asp Leu Leu Ser Asn Arg Val Ile Lys Lys Pro Met Ser
                565                 570                 575
```

```
Ala Ser Ala Leu Phe Val Gln Asp His Arg Pro Gln Phe Leu Ile Glu
            580                 585                 590

Asn Pro Lys Thr Ser Leu Glu Asp Ala Thr Leu Gln Ile Glu Glu Leu
            595                 600                 605

Trp Lys Thr Leu Ser Glu Glu Lys Leu Lys Tyr Glu Glu Lys Ala
            610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Arg Lys Ile Lys Pro
                    645                 650                 655

Thr Ser Ala Trp Asn Leu Ala Gln Lys His Lys Leu Lys Thr Ser Leu
            660                 665                 670

Ser Asn Gln Pro Lys Leu Asp Glu Leu Leu Gln Ser Gln Ile Glu Lys
            675                 680                 685

Arg Arg Ser Gln Asn Ile Lys Met Val Gln Ile Pro Phe Ser Met Lys
            690                 695                 700

Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
                    725                 730                 735

Leu Met Thr Ser Lys Thr Glu Val Met Leu Leu Asn Pro Tyr Arg Val
            740                 745                 750

Glu Glu Ala Leu Leu Phe Lys Arg Leu Leu Glu Asn His Lys Leu Pro
            755                 760                 765

Ala Glu Pro Leu Glu Lys Pro Ile Met Leu Thr Glu Ser Leu Phe Asn
            770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
                    805                 810                 815

Gly Phe Lys Ile Lys Leu Ile Pro Gly Val Ser Ile Thr Glu Asn Tyr
            820                 825                 830

Leu Glu Ile Glu Gly Met Ala Asn Cys Leu Pro Phe Tyr Gly Val Ala
            835                 840                 845

Asp Leu Lys Glu Ile Leu Asn Ala Ile Leu Asn Arg Asn Ala Lys Glu
            850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
                    885                 890                 895

Ile Gln Asp Ile Ile Tyr Arg Met Lys His Gln Phe Gly Asn Glu Ile
            900                 905                 910

Lys Glu Cys Val His Gly Arg Pro Phe Phe His Leu Thr Tyr Leu
            915                 920                 925

Pro Glu Thr Thr
    930
```

<210> SEQ ID NO 19
<211> LENGTH: 3063
<212> TYPE: DNA
<213> ORGANISM: Homo sapiens

<400> SEQUENCE: 19
ggcacgagtg gctgcttgcg gctagtggat ggtaattgcc tgcctcgcgc tagcagcaag    60

```
ctgctctgtt aaaagcgaaa atgaaacaat tgcctgcggc aacagttcga ctcctttcaa      120
gttctcagat catcacttcg gtggtcagtg ttgtaaaaga gcttattgaa aactccttgg      180
atgctggtgc cacaagcgta gatgttaaac tggagaacta tggatttgat aaaattgagg      240
tgcgagataa cggggagggt atcaaggctg ttgatgcacc tgtaatggca atgaagtact      300
acacctcaaa aataaatagt catgaagatc ttgaaaattt gacaacttac ggttttcgtg      360
gagaagcctt ggggtcaatt tgttgtatag ctgaggtttt aattacaaca gaacggctg       420
ctgataattt tagcacccag tatgttttag atggcagtgg ccacatactt tctcagaaac      480
cttcacatct tggtcaaggt acaactgtaa ctgctttaag attatttaag aatctacctg      540
taagaaagca gttttactca actgcaaaaa aatgtaaaga tgaaataaaa aagatccaag      600
atctcctcat gagctttggt atccttaaac ctgacttaag gattgtcttt gtacataaca      660
aggcagttat ttggcagaaa agcagagtat cagatcacaa gatggctctc atgtcagttc      720
tggggactgc tgttatgaac aatatggaat cctttcagta ccactctgaa gaatctcaga      780
tttatctcag tggatttctt ccaaagtgtg atgcagacca ctctttcact agtctttcaa      840
caccagaaag aagtttcatc ttcataaaca gtcgaccagt acatcaaaaa gatatcttaa      900
agttaatccg acatcattac aatctgaaat gcctaaagga atctactcgt ttgtatcctg      960
ttttctttct gaaaatcgat gttcctacag ctgatgttga tgtaaattta acaccagata     1020
aaagccaagt attattacaa aataaggaat ctgttttaat tgctcttgaa atctgatga      1080
cgacttgtta tggaccatta cctagtacaa attcttatga aaataataaa acagatgttt     1140
ccgcagctga catcgttctt agtaaaacag cagaaacaga tgtgcttttt aataaagtgg     1200
aatcatctgg aaagaattat tcaaatgttg atacttcagt cattccattc caaaatgata     1260
tgcataatga tgaatctgga aaaaacactg atgattgttt aaatcaccag ataagtattg     1320
gtgactttgg ttatggtcat tgtagtagtg aaatttctaa cattgataaa aacactaaga     1380
atgcatttca ggacatttca atgagtaatg tatcatggga gaactctcag acggaatata     1440
gtaaaacttg ttttataagt tccgttaagc acacccagtc agaaaatggc aataaagacc     1500
atatagatga gagtggggaa aatgaggaag aagcaggtct tgaaaactct tcggaaattt     1560
ctgcagatga gtggagcagg ggaaatatac ttaaaaattc agtgggagag aatattgaac     1620
ctgtgaaaat tttagtgcct gaaaaaagtt taccatgtaa agtaagtaat aataattatc     1680
caatccctga acaaatgaat cttaatgaag attcatgtaa caaaaaatca aatgtaatag     1740
ataataaatc tggaaaagtt acagcttatg atttacttag caatcgagta atcaagaaac     1800
ccatgtcagc aagtgctctt tttgttcaag atcatcgtcc tcagtttctc atagaaaatc     1860
ctaagactag tttagaggat gcaacactac aaattgaaga actgtggaag acattgagtg     1920
aagaggaaaa actgaaatat gaagagaagg ctactaaaga cttggaacga tacaatagtc     1980
aaatgaagag agccattgaa caggagtcac aaatgtcact aaaagatggc agaaaaaaga     2040
taaacccac cagcgcatgg aatttggccc agaagcacaa gttaaaaacc tcattatcta     2100
atcaaccaaa acttgatgaa ctccttcagt cccaaattga aaaagaagg agtcaaaata     2160
ttaaaatggt acagatcccc ttttctatga aaaacttaaa aataaatttt aagaaacaaa     2220
acaaagttga cttagaagag aaggatgaac cttgcttgat ccacaatctc aggtttcctg     2280
atgcatggct aatgacatcc aaaacagagg taatgttatt aaatccatat agagtagaag     2340
aagccctgct atttaaaaga cttcttgaga atcataaact tcctgcagag ccactggaaa     2400
```

-continued

```
agccaattat gttaacagag agtcttttta atggatctca ttatttagac gttttatata      2460
aaatgacagc agatgaccaa agatacagtg gatcaactta cctgtctgat cctcgtctta      2520
cagcgaatgg tttcaagata aaattgatac caggagtttc aattactgaa aattacttgg      2580
aaatagaagg aatggctaat tgtctcccat tctatggagt agcagattta aaagaaattc      2640
ttaatgctat attaaacaga aatgcaaagg aagtttatga atgtagacct cgcaaagtga      2700
taagttattt agagggagaa gcagtgcgtc tatccagaca attacccatg tacttatcaa      2760
aagaggacat ccaagacatt atctacagaa tgaagcacca gtttggaaat gaaattaaag      2820
agtgtgttca tggtcgccca ttttttcatc atttaaccta tcttccagaa actacatgat      2880
taaatatgtt taagaagatt agttaccatt gaaattggtt ctgtcataaa acagcatgag      2940
tctggtttta aattatcttt gtattatgtg tcacatggtt atttttttaaa tgaggattca      3000 ctgacttgtt tttatattga aaaagttccc acgtattgta gaaacgtaaa ataaactaat      3060
aac                                                                    3063
```

<210> SEQ ID NO 20
<211> LENGTH: 934
<212> TYPE: PRT
<213> ORGANISM: Homo sapiens

<400> SEQUENCE: 20

```
Met Ala Val Gln Pro Lys Glu Thr Leu Gln Leu Glu Ser Ala Ala Glu
  1               5                  10                  15

Val Gly Phe Val Arg Phe Phe Gln Gly Met Pro Glu Lys Pro Thr Thr
                 20                  25                  30

Thr Val Arg Leu Phe Asp Arg Gly Asp Phe Tyr Thr Ala His Gly Glu
             35                  40                  45

Asp Ala Leu Leu Ala Ala Arg Glu Val Phe Lys Thr Gln Gly Val Ile
         50                  55                  60

Lys Tyr Met Gly Pro Ala Gly Ala Lys Asn Leu Gln Ser Val Val Leu
 65                  70                  75                  80

Ser Lys Met Asn Phe Glu Ser Phe Val Lys Asp Leu Leu Leu Val Arg
                 85                  90                  95

Gln Tyr Arg Val Glu Val Tyr Lys Asn Arg Ala Gly Asn Lys Ala Ser
                100                 105                 110

Lys Glu Asn Asp Trp Tyr Leu Ala Tyr Lys Ala Ser Pro Gly Asn Leu
            115                 120                 125

Ser Gln Phe Glu Asp Ile Leu Phe Gly Asn Asn Asp Met Ser Ala Ser
        130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Glu Thr Ala Gly
        195                 200                 205

Asp Met Gly Lys Leu Arg Gln Ile Ile Gln Arg Gly Gly Ile Leu Ile
    210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Lys Gly Glu Gln Met Asn Ser Ala
                245                 250                 255
```

```
Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
            275                 280                 285

Phe Glu Leu Thr Thr Phe Asp Phe Ser Gln Tyr Met Lys Leu Asp Ile
            290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
                325                 330                 335

Gln Gly Gln Arg Leu Val Asn Gln Trp Ile Lys Gln Pro Leu Met Asp
            340                 345                 350

Lys Asn Arg Ile Glu Glu Arg Leu Asn Leu Val Glu Ala Phe Val Glu
            355                 360                 365

Asp Ala Glu Leu Arg Gln Thr Leu Gln Glu Asp Leu Leu Arg Arg Phe
            370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
                405                 410                 415

Val Ile Gln Ala Leu Glu Lys His Glu Gly Lys His Gln Lys Leu Leu
            420                 425                 430

Leu Ala Val Phe Val Thr Pro Leu Thr Asp Leu Arg Ser Asp Phe Ser
            435                 440                 445

Lys Phe Gln Glu Met Ile Glu Thr Thr Leu Asp Met Asp Gln Val Glu
            450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
                485                 490                 495

Ile Ser Ala Ala Arg Asp Leu Gly Leu Asp Pro Gly Lys Gln Ile Lys
            500                 505                 510

Leu Asp Ser Ser Ala Gln Phe Gly Tyr Tyr Phe Arg Val Thr Cys Lys
            515                 520                 525

Glu Glu Lys Val Leu Arg Asn Asn Lys Asn Phe Ser Thr Val Asp Ile
            530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Glu Ala Gln Asp Ala
                565                 570                 575

Ile Val Lys Glu Ile Val Asn Ile Ser Ser Gly Tyr Val Glu Pro Met
            580                 585                 590

Gln Thr Leu Asn Asp Val Leu Ala Gln Leu Asp Ala Val Val Ser Phe
            595                 600                 605

Ala His Val Ser Asn Gly Ala Pro Val Pro Tyr Val Arg Pro Ala Ile
            610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
            660                 665                 670
```

```
Gly Gly Lys Ser Thr Tyr Ile Arg Gln Thr Gly Val Ile Val Leu Met
            675                 680                 685
Ala Gln Ile Gly Cys Phe Val Pro Cys Glu Ser Ala Glu Val Ser Ile
        690                 695                 700
Val Asp Cys Ile Leu Ala Arg Val Gly Ala Gly Asp Ser Gln Leu Lys
705                 710                 715                 720
Gly Val Ser Thr Phe Met Ala Glu Met Leu Glu Thr Ala Ser Ile Leu
                725                 730                 735
Arg Ser Ala Thr Lys Asp Ser Leu Ile Ile Ile Asp Glu Leu Gly Arg
            740                 745                 750
Gly Thr Ser Thr Tyr Asp Gly Phe Gly Leu Ala Trp Ala Ile Ser Glu
        755                 760                 765
Tyr Ile Ala Thr Lys Ile Gly Ala Phe Cys Met Phe Ala Thr His Phe
    770                 775                 780
His Glu Leu Thr Ala Leu Ala Asn Gln Ile Pro Thr Val Asn Asn Leu
785                 790                 795                 800
His Val Thr Ala Leu Thr Thr Glu Glu Thr Leu Thr Met Leu Tyr Gln
                805                 810                 815
Val Lys Lys Gly Val Cys Asp Gln Ser Phe Gly Ile His Val Ala Glu
            820                 825                 830
Leu Ala Asn Phe Pro Lys His Val Ile Glu Cys Ala Lys Gln Lys Ala
        835                 840                 845
Leu Glu Leu Glu Glu Phe Gln Tyr Ile Gly Glu Ser Gln Gly Tyr Asp
    850                 855                 860
Ile Met Glu Pro Ala Ala Lys Lys Cys Tyr Leu Glu Arg Glu Gln Gly
865                 870                 875                 880
Glu Lys Ile Ile Gln Glu Phe Leu Ser Lys Val Lys Gln Met Pro Phe
                885                 890                 895
Thr Glu Met Ser Glu Glu Asn Ile Thr Ile Lys Leu Lys Gln Leu Lys
            900                 905                 910
Ala Glu Val Ile Ala Lys Asn Asn Ser Phe Val Asn Glu Ile Ile Ser
        915                 920                 925
Arg Ile Lys Val Thr Thr
    930

<210> SEQ ID NO 21
<211> LENGTH: 3145
<212> TYPE: DNA
<213> ORGANISM: Homo sapiens

<400> SEQUENCE: 21
ggcgggaaac agcttagtgg gtgtggggtc gcgcattttc ttcaaccagg aggtgaggag      60
gtttcgacat ggcggtgcag ccgaaggaga cgctgcagtt ggagagcgcg gccgaggtcg     120
gcttcgtgcg cttctttcag ggcatgccgg agaagccgac caccacagtg cgccttttcg     180
accgggcgac ttctatacg gcgcacggcg aggacgcgct gctggccgcc cgggaggtgt     240
tcaagaccca gggggtgatc aagtacatgg ggccggcagg agcaaagaat ctgcagagtg     300
ttgtgcttag taaaatgaat tttgaatctt ttgtaaaaga tcttcttctg gttcgtcagt     360
atagagttga agtttataag aatagagctg gaaataaggc atccaaggag aatgattggt     420
atttggcata taaggcttct cctggcaatc tctctcagtt tgaagacatt ctctttggta     480
acaatgatat gtcagcttcc attggtgttg tgggtgttaa aatgtccgca gttgatggcc     540
agagacaggt tggagttggg tatgtggatt ccatacagag gaaactagga ctgtgtgaat     600
```

| | |
|---|---|
| tccctgataa tgatcagttc tccaatcttg aggctctcct catccagatt ggaccaaagg | 660 |
| aatgtgtttt acccggagga gagactgctg gagacatggg gaaactgaga cagataattc | 720 |
| aaagaggagg aattctgatc acagaaagaa aaaaagctga cttttccaca aaagacattt | 780 |
| atcaggacct caaccggttg ttgaaaggca aaaagggaga gcagatgaat agtgctgtat | 840 |
| tgccagaaat ggagaatcag gttgcagttt catcactgtc tgcggtaatc aagttttag | 900 |
| aactcttatc agatgattcc aactttggac agtttgaact gactacttt gacttcagcc | 960 |
| agtatatgaa attggatatt gcagcagtca gagcccttaa cctttttcag ggttctgttg | 1020 |
| aagataccac tggctctcag tctctggctg ccttgctgaa taagtgtaaa acccctcaag | 1080 |
| gacaaagact tgttaaccag tggattaagc agcctctcat ggataagaac agaatagagg | 1140 |
| agagattgaa tttagtggaa gcttttgtag aagatgcaga attgaggcag actttacaag | 1200 |
| aagatttact tcgtcgattc ccagatctta accgacttgc caagaagttt caaagacaag | 1260 |
| cagcaaactt acaagattgt taccgactct atcagggtat aaatcaacta cctaatgtta | 1320 |
| tacaggctct ggaaaaacat gaaggaaaac accagaaatt attgttggca gtttttgtga | 1380 |
| ctcctcttac tgatcttcgt tctgacttct ccaagtttca ggaaatgata gaaacaactt | 1440 |
| tagatatgga tcaggtggaa aaccatgaat tccttgtaaa accttcattt gatcctaatc | 1500 |
| tcagtgaatt aagagaaata atgaatgact tggaaaagaa gatgcagtca acattaataa | 1560 |
| gtgcagccag agatcttggc ttggaccctg gcaaacagat taaactggat tccagtgcac | 1620 |
| agtttggata ttactttcgt gtaacctgta aggaagaaaa agtccttcgt aacaataaaa | 1680 |
| actttagtac tgtagatatc cagaagaatg gtgttaaatt taccaacagc aaattgactt | 1740 |
| ctttaaatga gagtatacc aaaaataaaa cagaatatga gaagcccag gatgccattg | 1800 |
| ttaaagaaat tgtcaatatt tcttcaggct atgtagaacc aatgcagaca ctcaatgatg | 1860 |
| tgttagctca gctagatgct gttgtcagct ttgctcacgt gtcaaatgga gcacctgttc | 1920 |
| catatgtacg accagccatt ttggagaaag gacaaggaag aattatatta aaagcatcca | 1980 |
| ggcatgcttg tgttgaagtt caagatgaaa ttgcatttat tcctaatgac gtatactttg | 2040 |
| aaaaagataa acagatgttc cacatcatta ctggccccaa tatgggaggt aaatcaacat | 2100 |
| atattcgaca aactgggtg atagtactca tggcccaaat tgggtgtttt gtgccatgtg | 2160 |
| agtcagcaga agtgtccatt gtggactgca tcttagcccg agtaggggct ggtgacagtc | 2220 |
| aattgaaagg agtctccacg ttcatggctg aaatgttgga aactgcttct atcctcaggt | 2280 |
| ctgcaaccaa agattcatta ataatcatag atgaattggg aagaggaact tctacctacg | 2340 |
| atggatttgg gttagcatgg gctatatcag aatacattgc aacaaagatt ggtgcttttt | 2400 |
| gcatgtttgc aacccatttt catgaactta ctgccttggc caatcagata ccaactgtta | 2460 |
| ataatctaca tgtcacagca ctcaccactg aagagacctt aactatgctt tatcaggtga | 2520 |
| agaaaggtgt ctgtgatcaa agttttggga ttcatgttgc agagcttgct aatttcccta | 2580 |
| agcatgtaat agagtgtgct aaacagaaag ccctggaact tgaggagttt cagtatattg | 2640 |
| gagaatcgca aggatatgat atcatggaac cagcagcaaa gaagtgctat ctggaaagag | 2700 |
| agcaaggtga aaaattatt caggagttcc tgtccaaggt gaaacaaatg ccctttactg | 2760 |
| aaatgtcaga agaaacatc acaataaagt taaacagct aaaagctgaa gtaatagcaa | 2820 |
| agaataatag ctttgtaaat gaaatcattt cacgaataaa agttactacg tgaaaaatcc | 2880 |
| cagtaatgga atgaaggtaa tattgataag ctattgtctg taatagtttt atattgtttt | 2940 |
| atattaaccc ttttccata gtgttaactg tcagtgccca tgggctatca acttaataag | 3000 |

```
atatttagta atattttact ttgaggacat tttcaaagat ttttattttg aaaaatgaga    3060
gctgtaactg aggactgttt gcaattgaca taggcaataa taagtgatgt gctgaatttt    3120
ataaataaaa tcatgtagtt tgtgg                                          3145

<210> SEQ ID NO 22
<211> LENGTH: 756
<212> TYPE: PRT
<213> ORGANISM: Homo sapiens

<400> SEQUENCE: 22

Met Ser Phe Val Ala Gly Val Ile Arg Arg Leu Asp Glu Thr Val Val
 1               5                  10                  15

Asn Arg Ile Ala Ala Gly Glu Val Ile Gln Arg Pro Ala Asn Ala Ile
                20                  25                  30

Lys Glu Met Ile Glu Asn Cys Leu Asp Ala Lys Ser Thr Ser Ile Gln
            35                  40                  45

Val Ile Val Lys Glu Gly Gly Leu Lys Leu Ile Gln Ile Gln Asp Asn
        50                  55                  60

Gly Thr Gly Ile Arg Lys Glu Asp Leu Asp Ile Val Cys Glu Arg Phe
 65                  70                  75                  80

Thr Thr Ser Lys Leu Gln Ser Phe Glu Asp Leu Ala Ser Ile Ser Thr
                 85                  90                  95

Tyr Gly Phe Arg Gly Glu Ala Leu Ala Ser Ile Ser His Val Ala His
                100                 105                 110

Val Thr Ile Thr Thr Lys Thr Ala Asp Gly Lys Cys Ala Tyr Arg Ala
            115                 120                 125

Ser Tyr Ser Asp Gly Lys Leu Lys Ala Pro Pro Lys Pro Cys Ala Gly
        130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
            180                 185                 190

Ser Val Lys Lys Gln Gly Glu Thr Val Ala Asp Val Arg Thr Leu Pro
        195                 200                 205

Asn Ala Ser Thr Val Asp Asn Ile Arg Ser Ile Phe Gly Asn Ala Val
    210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
            260                 265                 270

Arg Lys Ala Ile Glu Thr Val Tyr Ala Ala Tyr Leu Pro Lys Asn Thr
        275                 280                 285

His Pro Phe Leu Tyr Leu Ser Leu Glu Ile Ser Pro Gln Asn Val Asp
    290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
```

-continued

```
                340             345             350
Ala Gly Pro Ser Gly Glu Met Val Lys Ser Thr Thr Ser Leu Thr Ser
            355                 360                 365
Ser Ser Thr Ser Gly Ser Ser Asp Lys Val Tyr Ala His Gln Met Val
        370                 375                 380
Arg Thr Asp Ser Arg Glu Gln Lys Leu Asp Ala Phe Leu Gln Pro Leu
385                 390                 395                 400
Ser Lys Pro Leu Ser Ser Gln Pro Gln Ala Ile Val Thr Glu Asp Lys
                405                 410                 415
Thr Asp Ile Ser Ser Gly Arg Ala Arg Gln Gln Asp Glu Glu Met Leu
            420                 425                 430
Glu Leu Pro Ala Pro Ala Glu Val Ala Ala Lys Asn Gln Ser Leu Glu
        435                 440                 445
Gly Asp Thr Thr Lys Gly Thr Ser Glu Met Ser Glu Lys Arg Gly Pro
    450                 455                 460
Thr Ser Ser Asn Pro Arg Lys Arg His Arg Glu Asp Ser Asp Val Glu
465                 470                 475                 480
Met Val Glu Asp Asp Ser Arg Lys Glu Met Thr Ala Ala Cys Thr Pro
                485                 490                 495
Arg Arg Arg Ile Ile Asn Leu Thr Ser Val Leu Ser Leu Gln Glu Glu
            500                 505                 510
Ile Asn Glu Gln Gly His Glu Val Leu Arg Glu Met Leu His Asn His
        515                 520                 525
Ser Phe Val Gly Cys Val Asn Pro Gln Trp Ala Leu Ala Gln His Gln
    530                 535                 540
Thr Lys Leu Tyr Leu Leu Asn Thr Thr Lys Leu Ser Glu Glu Leu Phe
545                 550                 555                 560
Tyr Gln Ile Leu Ile Tyr Asp Phe Ala Asn Phe Gly Val Leu Arg Leu
                565                 570                 575
Ser Glu Pro Ala Pro Leu Phe Asp Leu Ala Met Leu Ala Leu Asp Ser
            580                 585                 590
Pro Glu Ser Gly Trp Thr Glu Glu Asp Gly Pro Lys Glu Gly Leu Ala
        595                 600                 605
Glu Tyr Ile Val Glu Phe Leu Lys Lys Lys Ala Glu Met Leu Ala Asp
    610                 615                 620
Tyr Phe Ser Leu Glu Ile Asp Glu Glu Gly Asn Leu Ile Gly Leu Pro
625                 630                 635                 640
Leu Leu Ile Asp Asn Tyr Val Pro Pro Leu Glu Gly Leu Pro Ile Phe
                645                 650                 655
Ile Leu Arg Leu Ala Thr Glu Val Asn Trp Asp Glu Glu Lys Glu Cys
            660                 665                 670
Phe Glu Ser Leu Ser Lys Glu Cys Ala Met Phe Tyr Ser Ile Arg Lys
        675                 680                 685
Gln Tyr Ile Ser Glu Glu Ser Thr Leu Ser Gly Gln Gln Ser Glu Val
    690                 695                 700
Pro Gly Ser Ile Pro Asn Ser Trp Lys Trp Thr Val Glu His Ile Val
705                 710                 715                 720
Tyr Lys Ala Leu Arg Ser His Ile Leu Pro Pro Lys His Phe Thr Glu
                725                 730                 735
Asp Gly Asn Ile Leu Gln Leu Ala Asn Leu Pro Asp Leu Tyr Lys Val
            740                 745                 750
Phe Glu Arg Cys
            755
```

<210> SEQ ID NO 23
<211> LENGTH: 2484
<212> TYPE: DNA
<213> ORGANISM: Homo sapiens

<400> SEQUENCE: 23

| | | | | | |
|---|---|---|---|---|---|
| cttggctctt | ctggcgccaa | aatgtcgttc | gtggcagggg | ttattcggcg | gctggacgag | 60 |
| acagtggtga | accgcatcgc | ggcggggggaa | gttatccagc | ggccagctaa | tgctatcaaa | 120 |
| gagatgattg | agaactgttt | agatgcaaaa | tccacaagta | ttcaagtgat | tgttaaagag | 180 |
| ggaggcctga | agttgattca | gatccaagac | aatggcaccg | ggatcaggaa | agaagatctg | 240 |
| gatattgtat | gtgaaaggtt | cactactagt | aaactgcagt | cctttgagga | tttagccagt | 300 |
| atttctacct | atggctttcg | aggtgaggct | ttggccagca | taagccatgt | ggctcatgtt | 360 |
| actattacaa | cgaaaacagc | tgatggaaag | tgtgcataca | gagcaagtta | ctcagatgga | 420 |
| aaactgaaag | cccctcctaa | accatgtgct | ggcaatcaag | ggacccagat | cacggtggag | 480 |
| gacctttttt | acaacatagc | cacgaggaga | aaagctttaa | aaaatccaag | tgaagaatat | 540 |
| gggaaaattt | tggaagttgt | tggcaggtat | tcagtacaca | atgcaggcat | tagtttctca | 600 |
| gttaaaaaac | aaggagagac | agtagctgat | gttaggacac | acccaatgc | ctcaaccgtg | 660 |
| gacaatattc | gctccatctt | tggaaatgct | gttagtcgag | aactgataga | aattggatgt | 720 |
| gaggataaaa | ccctagcctt | caaaatgaat | ggttacatat | ccaatgcaaa | ctactcagtg | 780 |
| aagaagtgca | tcttcttact | cttcatcaac | catcgtctgg | tagaatcaac | ttccttgaga | 840 |
| aaagccatag | aaacagtgta | tgcagcctat | ttgcccaaaa | acacacaccc | attcctgtac | 900 |
| ctcagtttag | aaatcagtcc | ccagaatgtg | atgttaatg | tgcaccccac | aaagcatgaa | 960 |
| gttcacttcc | tgcacgagga | gagcatcctg | gagcgggtgc | agcagcacat | cgagagcaag | 1020 |
| ctcctgggct | ccaattcctc | caggatgtac | ttcacccaga | ctttgctacc | aggacttgct | 1080 |
| ggcccctctg | gggagatggt | taaatccaca | acaagtctga | cctcgtcttc | tacttctgga | 1140 |
| agtagtgata | aggtctatgc | ccaccagatg | gttcgtacag | attcccggga | acagaagctt | 1200 |
| gatgcatttc | tgcagcctct | gagcaaaccc | ctgtccagtc | agccccaggc | cattgtcaca | 1260 |
| gaggataaga | cagatatttc | tagtggcagg | gctaggcagc | aagatgagga | gatgcttgaa | 1320 |
| ctcccagccc | ctgctgaagt | ggctgccaaa | aatcagagct | tggaggggga | tacaacaaag | 1380 |
| gggacttcag | aaatgtcaga | gaagagagga | cctacttcca | gcaacccag | aaagagacat | 1440 |
| cgggaagatt | ctgatgtgga | aatggtggaa | gatgattccc | gaaaggaaat | gactgcagct | 1500 |
| tgtacccccc | ggagaaggat | cattaacctc | actagtgttt | tgagtctcca | ggaagaaatt | 1560 |
| aatgagcagg | gacatgaggt | tctccgggag | atgttgcata | ccactccctt | cgtgggctgt | 1620 |
| gtgaatcctc | agtgggcctt | ggcacagcat | caaaccaagt | tataccttct | caacaccacc | 1680 |
| aagcttagtg | aagaactgtt | ctaccagata | ctcatttatg | attttgccaa | ttttggtgtt | 1740 |
| ctcaggttat | cggagccagc | accgctcttt | gaccttgcca | tgcttgcctt | agatagtcca | 1800 |
| gagagtggct | ggacagagga | agatggtccc | aaagaaggac | ttgctgaata | cattgttgag | 1860 |
| tttctgaaga | agaggctgaa | gatgcttgca | gactatttct | cttttggaaat | tgatgaggaa | 1920 |
| gggaacctga | ttggattacc | ccttctgatt | gacaactatg | tgccccttt | ggagggactg | 1980 |
| cctatcttca | ttcttcgact | agccactgag | gtgaattggg | acgaagaaaa | ggaatgtttt | 2040 |
| gaaagcctca | gtaaagaatg | cgctatgttc | tattccatcc | ggaagcagta | catatctgag | 2100 |

```
gagtcgaccc tctcaggcca gcagagtgaa gtgcctggct ccattccaaa ctcctggaag    2160
tggactgtgg aacacattgt ctataaagcc ttgcgctcac acattctgcc tcctaaacat    2220
ttcacagaag atggaaatat cctgcagctt gctaacctgc ctgatctata caaagtcttt    2280
gagaggtgtt aaatatggtt atttatgcac tgtgggatgt gttcttcttt ctctgtattc    2340
cgatacaaag tgttgtatca aagtgtgata tacaaagtgt accaacataa gtgttggtag    2400
cacttaagac ttatacttgc cttctgatag tattccttta tacacagtgg attgattata    2460
aataaataga tgtgtcttaa cata                                            2484
```

<210> SEQ ID NO 24
<211> LENGTH: 133
<212> TYPE: PRT
<213> ORGANISM: Homo sapiens

<400> SEQUENCE: 24

```
Met Lys Gln Leu Pro Ala Ala Thr Val Arg Leu Leu Ser Ser Ser Gln
  1               5                  10                  15

Ile Ile Thr Ser Val Val Ser Val Val Lys Glu Leu Ile Glu Asn Ser
             20                  25                  30

Leu Asp Ala Gly Ala Thr Ser Val Asp Val Lys Leu Glu Asn Tyr Gly
         35                  40                  45

Phe Asp Lys Ile Glu Val Arg Asp Asn Gly Glu Gly Ile Lys Ala Val
     50                  55                  60

Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
                 85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys
    130
```

<210> SEQ ID NO 25
<211> LENGTH: 426
<212> TYPE: DNA
<213> ORGANISM: Homo sapiens

<400> SEQUENCE: 25

```
cgaggcggat cgggtgttgc atccatggag cgagctgaga gctcgagtac agaacctgct      60
aaggccatca aacctattga tcggaagtca gtccatcaga tttgctctgg gcaggtggta    120
ctgagtctaa gcactgcggt aaaggagtta gtagaaaaca gtctggatgc tggtgccact    180
aatattgatc taaagcttaa ggactatgga gtggatcttt tgaagtttc agacaatgga    240 tgtgggtag aagaagaaaa cttcgaaggc ttaactctga acatcacac atctaagatt    300 caagagtttg ccgacctaac tcaggttgaa acttttggct tcggggggga agctctgagc    360
tcactttgtg cactgagcga tgtcaccatt tctacctgcc acgcatcggc gaaggttgga    420
acttga                                                              426
```

<210> SEQ ID NO 26
<211> LENGTH: 1360
<212> TYPE: PRT
<213> ORGANISM: Homo sapiens

<400> SEQUENCE: 26

```
Met Ser Arg Gln Ser Thr Leu Tyr Ser Phe Phe Pro Lys Ser Pro Ala
  1               5                  10                  15

Leu Ser Asp Ala Asn Lys Ala Ser Ala Arg Ala Ser Arg Glu Gly Gly
             20                  25                  30

Arg Ala Ala Ala Pro Gly Ala Ser Pro Ser Pro Gly Gly Asp Ala
         35                  40                  45

Ala Trp Ser Glu Ala Gly Pro Gly Pro Arg Pro Leu Ala Arg Ser Ala
 50                      55                  60

Ser Pro Pro Lys Ala Lys Asn Leu Asn Gly Gly Leu Arg Arg Ser Val
 65                  70                  75                  80

Ala Pro Ala Ala Pro Thr Ser Cys Asp Phe Ser Pro Gly Asp Leu Val
                 85                  90                  95

Trp Ala Lys Met Glu Gly Tyr Pro Trp Trp Pro Cys Leu Val Tyr Asn
                100                 105                 110

His Pro Phe Asp Gly Thr Phe Ile Arg Glu Lys Gly Lys Ser Val Arg
            115                 120                 125

Val His Val Gln Phe Phe Asp Asp Ser Pro Thr Arg Gly Trp Val Ser
        130                 135                 140

Lys Arg Leu Leu Lys Pro Tyr Thr Gly Ser Lys Ser Lys Glu Ala Gln
145                 150                 155                 160

Lys Gly Gly His Phe Tyr Ser Ala Lys Pro Glu Ile Leu Arg Ala Met
                165                 170                 175

Gln Arg Ala Asp Glu Ala Leu Asn Lys Asp Lys Ile Lys Arg Leu Glu
            180                 185                 190

Leu Ala Val Cys Asp Glu Pro Ser Glu Pro Glu Glu Glu Glu Met
        195                 200                 205

Glu Val Gly Thr Thr Tyr Val Thr Asp Lys Ser Glu Glu Asp Asn Glu
210                 215                 220

Ile Glu Ser Glu Glu Val Gln Pro Lys Thr Gln Gly Ser Arg Arg
225                 230                 235                 240

Ser Ser Arg Gln Ile Lys Lys Arg Arg Val Ile Ser Asp Ser Glu Ser
                245                 250                 255

Asp Ile Gly Gly Ser Asp Val Glu Phe Lys Pro Asp Thr Lys Glu Glu
            260                 265                 270

Gly Ser Ser Asp Glu Ile Ser Ser Gly Val Gly Asp Ser Glu Ser Glu
        275                 280                 285

Gly Leu Asn Ser Pro Val Lys Val Ala Arg Lys Arg Lys Arg Met Val
290                 295                 300

Thr Gly Asn Gly Ser Leu Lys Arg Lys Ser Arg Lys Glu Thr Pro
305                 310                 315                 320

Ser Ala Thr Lys Gln Ala Thr Ser Ile Ser Ser Glu Thr Lys Asn Thr
                325                 330                 335

Leu Arg Ala Phe Ser Ala Pro Gln Asn Ser Glu Ser Gln Ala His Val
            340                 345                 350

Ser Gly Gly Gly Asp Asp Ser Ser Arg Pro Thr Val Trp Tyr His Glu
        355                 360                 365

Thr Leu Glu Trp Leu Lys Glu Glu Lys Arg Arg Asp Glu His Arg Arg
370                 375                 380

Arg Pro Asp His Pro Asp Phe Asp Ala Ser Thr Leu Tyr Val Pro Glu
385                 390                 395                 400

Asp Phe Leu Asn Ser Cys Thr Pro Gly Met Arg Lys Trp Trp Gln Ile
                405                 410                 415
```

```
Lys Ser Gln Asn Phe Asp Leu Val Ile Cys Tyr Lys Val Gly Lys Phe
            420                 425                 430

Tyr Glu Leu Tyr His Met Asp Ala Leu Ile Gly Val Ser Glu Leu Gly
            435                 440                 445

Leu Val Phe Met Lys Gly Asn Trp Ala His Ser Gly Phe Pro Glu Ile
            450                 455                 460

Ala Phe Gly Arg Tyr Ser Asp Ser Leu Val Gln Lys Gly Tyr Lys Val
465                 470                 475                 480

Ala Arg Val Glu Gln Thr Glu Thr Pro Glu Met Met Glu Ala Arg Cys
            485                 490                 495

Arg Lys Met Ala His Ile Ser Lys Tyr Asp Arg Val Val Arg Arg Glu
            500                 505                 510

Ile Cys Arg Ile Ile Thr Lys Gly Thr Gln Thr Tyr Ser Val Leu Glu
            515                 520                 525

Gly Asp Pro Ser Glu Asn Tyr Ser Lys Tyr Leu Leu Ser Leu Lys Glu
            530                 535                 540

Lys Glu Glu Asp Ser Ser Gly His Thr Arg Ala Tyr Gly Val Cys Phe
545                 550                 555                 560

Val Asp Thr Ser Leu Gly Lys Phe Phe Ile Gly Gln Phe Ser Asp Asp
            565                 570                 575

Arg His Cys Ser Arg Phe Arg Thr Leu Val Ala His Tyr Pro Pro Val
            580                 585                 590

Gln Val Leu Phe Glu Lys Gly Asn Leu Ser Lys Glu Thr Lys Thr Ile
            595                 600                 605

Leu Lys Ser Ser Leu Ser Cys Ser Leu Gln Glu Gly Leu Ile Pro Gly
            610                 615                 620

Ser Gln Phe Trp Asp Ala Ser Lys Thr Leu Arg Thr Leu Leu Glu Glu
625                 630                 635                 640

Glu Tyr Phe Arg Glu Lys Leu Ser Asp Gly Ile Gly Val Met Leu Pro
            645                 650                 655

Gln Val Leu Lys Gly Met Thr Ser Glu Ser Asp Ser Ile Gly Leu Thr
            660                 665                 670

Pro Gly Glu Lys Ser Glu Leu Ala Leu Ser Ala Leu Gly Gly Cys Val
            675                 680                 685

Phe Tyr Leu Lys Lys Cys Leu Ile Asp Gln Glu Leu Leu Ser Met Ala
            690                 695                 700

Asn Phe Glu Glu Tyr Ile Pro Leu Asp Ser Asp Thr Val Ser Thr Thr
705                 710                 715                 720

Arg Ser Gly Ala Ile Phe Thr Lys Ala Tyr Gln Arg Met Val Leu Asp
            725                 730                 735

Ala Val Thr Leu Asn Asn Leu Glu Ile Phe Leu Asn Gly Thr Asn Gly
            740                 745                 750

Ser Thr Glu Gly Thr Leu Leu Glu Arg Val Asp Thr Cys His Thr Pro
            755                 760                 765

Phe Gly Lys Arg Leu Leu Lys Gln Trp Leu Cys Ala Pro Leu Cys Asn
            770                 775                 780

His Tyr Ala Ile Asn Asp Arg Leu Asp Ala Ile Glu Asp Leu Met Val
785                 790                 795                 800

Val Pro Asp Lys Ile Ser Glu Val Val Glu Leu Leu Lys Lys Leu Pro
            805                 810                 815

Asp Leu Glu Arg Leu Leu Ser Lys Ile His Asn Val Gly Ser Pro Leu
            820                 825                 830
```

-continued

Lys Ser Gln Asn His Pro Asp Ser Arg Ala Ile Met Tyr Glu Glu Thr
            835                 840                 845
Thr Tyr Ser Lys Lys Lys Ile Ile Asp Phe Leu Ser Ala Leu Glu Gly
            850                 855                 860
Phe Lys Val Met Cys Lys Ile Ile Gly Ile Met Glu Glu Val Ala Asp
865                 870                 875                 880
Gly Phe Lys Ser Lys Ile Leu Lys Gln Val Ile Ser Leu Gln Thr Lys
            885                 890                 895
Asn Pro Glu Gly Arg Phe Pro Asp Leu Thr Val Glu Leu Asn Arg Trp
            900                 905                 910
Asp Thr Ala Phe Asp His Glu Lys Ala Arg Lys Thr Gly Leu Ile Thr
            915                 920                 925
Pro Lys Ala Gly Phe Asp Ser Asp Tyr Asp Gln Ala Leu Ala Asp Ile
            930                 935                 940
Arg Glu Asn Glu Gln Ser Leu Leu Glu Tyr Leu Glu Lys Gln Arg Asn
945                 950                 955                 960
Arg Ile Gly Cys Arg Thr Ile Val Tyr Trp Gly Ile Gly Arg Asn Arg
            965                 970                 975
Tyr Gln Leu Glu Ile Pro Glu Asn Phe Thr Thr Arg Asn Leu Pro Glu
            980                 985                 990
Glu Tyr Glu Leu Lys Ser Thr Lys Lys Gly Cys Lys Arg Tyr Trp Thr
            995                 1000                1005
Lys Thr Ile Glu Lys Lys Leu Ala Asn Leu Ile Asn Ala Glu Glu Arg
            1010                1015                1020
Arg Asp Val Ser Leu Lys Asp Cys Met Arg Arg Leu Phe Tyr Asn Phe
1025                1030                1035                1040
Asp Lys Asn Tyr Lys Asp Trp Gln Ser Ala Val Glu Cys Ile Ala Val
            1045                1050                1055
Leu Asp Val Leu Leu Cys Leu Ala Asn Tyr Ser Arg Gly Gly Asp Gly
            1060                1065                1070
Pro Met Cys Arg Pro Val Ile Leu Leu Pro Glu Asp Thr Pro Pro Phe
            1075                1080                1085
Leu Glu Leu Lys Gly Ser Arg His Pro Cys Ile Thr Lys Thr Phe Phe
            1090                1095                1100
Gly Asp Asp Phe Ile Pro Asn Asp Ile Leu Ile Gly Cys Glu Glu Glu
1105                1110                1115                1120
Glu Gln Glu Asn Gly Lys Ala Tyr Cys Val Leu Val Thr Gly Pro Asn
            1125                1130                1135
Met Gly Gly Lys Ser Thr Leu Met Arg Gln Ala Gly Leu Leu Ala Val
            1140                1145                1150
Met Ala Gln Met Gly Cys Tyr Val Pro Ala Glu Val Cys Arg Leu Thr
            1155                1160                1165
Pro Ile Asp Arg Val Phe Thr Arg Leu Gly Ala Ser Asp Arg Ile Met
            1170                1175                1180
Ser Gly Glu Ser Thr Phe Phe Val Glu Leu Ser Glu Thr Ala Ser Ile
1185                1190                1195                1200
Leu Met His Ala Thr Ala His Ser Leu Val Leu Val Asp Glu Leu Gly
            1205                1210                1215
Arg Gly Thr Ala Thr Phe Asp Gly Thr Ala Ile Ala Asn Ala Val Val
            1220                1225                1230
Lys Glu Leu Ala Glu Thr Ile Lys Cys Arg Thr Leu Phe Ser Thr His
            1235                1240                1245
Tyr His Ser Leu Val Glu Asp Tyr Ser Gln Asn Val Ala Val Arg Leu

```
                1250                 1255                 1260
Gly His Met Ala Cys Met Val Glu Asn Glu Cys Glu Asp Pro Ser Gln
1265                 1270                 1275                 1280

Glu Thr Ile Thr Phe Leu Tyr Lys Phe Ile Lys Gly Ala Cys Pro Lys
                1285                 1290                 1295

Ser Tyr Gly Phe Asn Ala Ala Arg Leu Ala Asn Leu Pro Glu Glu Val
                1300                 1305                 1310

Ile Gln Lys Gly His Arg Lys Ala Arg Glu Phe Glu Lys Met Asn Gln
1315                 1320                 1325

Ser Leu Arg Leu Phe Arg Glu Val Cys Leu Ala Ser Glu Arg Ser Thr
                1330                 1335                 1340

Val Asp Ala Glu Ala Val His Lys Leu Leu Thr Leu Ile Lys Glu Leu
1345                 1350                 1355                 1360

<210> SEQ ID NO 27
<211> LENGTH: 4244
<212> TYPE: DNA
<213> ORGANISM: Homo sapiens

<400> SEQUENCE: 27
gccgcgcggt agatgcggtg cttttaggag ctccgtccga cagaacggtt gggccttgcc        60
ggctgtcggt atgtcgcgac agagcaccct gtacagcttc ttccccaagt ctccggcgct       120
gagtgatgcc aacaaggcct cggccagggc ctcacgcgaa ggcggccgtg ccgccgctgc       180
ccccggggcc tctccttccc caggcgggga tgcggcctgg agcgaggctg gcctgggcc        240
caggcccttg gcgcgctccg cgtcaccgcc caaggcgaag aacctcaacg agggctgcg        300
gagatcggta gcgcctgctg cccccaccag ttgtgacttc tcaccaggag atttggtttg       360
ggccaagatg gagggttacc cctggtggcc ttgtctggtt acaaccacc cctttgatgg        420
aacattcatc cgcgagaaag ggaaatcagt ccgtgttcat gtacagtttt ttgatgacag       480
cccaacaagg ggctgggtta gcaaaaggct tttaaagcca tatacaggtt caaaatcaaa       540
ggaagcccag aagggaggtc atttttacag tgcaaagcct gaaatactga agcaatgca       600
acgtgcagat gaagccttaa ataaagacaa gattaagagg cttgaattgg cagtttgtga       660
tgagccctca gagccagaag aggaagaaga gatggaggta ggcacaactt acgtaacaga       720
taagagtgaa gaagataatg aaattgagag tgaagaggaa gtacagccta agacacaagg       780
atctaggcga agtagccgcc aaataaaaaa acgaagggtc atatcagatt ctgagagtga       840
cattggtggc tctgatgtgg aatttaagcc agacactaag gaggaaggaa gcagtgatga       900
aataagcagt ggagtggggg atagtgagag tgaaggcctg aacagccctg tcaaagttgc       960
tcgaaagcgg aagagaatgg tgactggaaa tggctctctt aaaaggaaaa gctctaggaa      1020
ggaaacgccc tcagccacca acaagcaac tagcatttca tcagaaacca agaatacttt      1080
gagagctttc tctgccccctc aaaattctga atcccaagcc cacgttagtg gaggtggtga      1140
tgacagtagt cgccctactg tttggtatca tgaaactta gaatggctta aggaggaaaa      1200
gagaagagat gagcacagga ggaggcctga tcaccccgat tttgatgcat ctacactcta      1260
tgtgcctgag gatttcctca attcttgtac tcctgggatg aggaagtggt ggcagattaa      1320
gtctcagaac tttgatcttg tcatctgtta caggtgggg aaattttatg agctgtacca      1380
catggatgct cttattggag tcagtgaact ggggctggta ttcatgaaag caactgggc       1440
ccattctggc tttcctgaaa ttgcatttgg ccgttattca gattccctgg tgcagaaggg      1500
ctataaagta gcacgagtgg aacagactga gactccagaa atgatggagg cacgatgtag      1560
```

-continued

```
aaagatggca catatatcca agtatgatag agtggtgagg agggagatct gtaggatcat    1620
taccaagggt acacagactt acagtgtgct ggaaggtgat ccctctgaga actacagtaa    1680
gtatcttctt agcctcaaag aaaaagagga agattcttct ggccatactc gtgcatatgg    1740
tgtgtgcttt gttgatactt cactgggaaa gttttttcata ggtcagtttt cagatgatcg    1800
ccattgttcg agatttagga ctctagtggc acactatccc ccagtacaag ttttatttga    1860
aaaaggaaat ctctcaaagg aaactaaaac aattctaaag agttcattgt cctgttctct    1920
tcaggaaggt ctgatacccg gctcccagtt ttgggatgca tccaaaactt tgagaactct    1980
ccttgaggaa gaatatttta gggaaaagct aagtgatggc attgggtga tgttacccca    2040
ggtgcttaaa ggtatgactt cagagtctga ttccattggg ttgacaccag gagagaaaag    2100
tgaattggcc ctctctgctc taggtggttg tgtcttctac ctcaaaaaat gccttattga    2160
tcaggagctt ttatcaatgg ctaattttga agaatatatt cccttggatt ctgacacagt    2220
cagcactaca agatctggtg ctatcttcac caaagcctat caacgaatgg tgctagatgc    2280
agtgacatta aacaacttgg agattttttct gaatggaaca aatggttcta ctgaaggaac    2340
cctactagag agggttgata cttgccatac tccttttggt aagcggctcc taaagcaatg    2400
gctttgtgcc ccactctgta accattatgc tattaatgat cgtctagatg ccatagaaga    2460
cctcatggtt gtgcctgaca aaatctccga agttgtagag cttctaaaga agcttccaga    2520
tcttgagagg ctactcagta aaattcataa tgttgggtct cccctgaaga gtcagaacca    2580
cccagacagc agggctataa tgtatgaaga aactacatac agcaagaaga agattattga    2640
ttttctttct gctctggaag gattcaaagt aatgtgtaaa attataggga tcatggaaga    2700
agttgctgat ggttttaagt ctaaaatcct taagcaggtc atctctctgc agacaaaaaa    2760
tcctgaaggt cgttttcctg atttgactgt agaattgaac cgatgggata cagcctttga    2820
ccatgaaaag gctcgaaaga ctggacttat tactcccaaa gcaggctttg actctgatta    2880
tgaccaagct cttgctgaca taagagaaaa tgaacagagc ctcctggaat acctagagaa    2940
acagcgcaac agaattggct gtaggaccat agtctattgg gggattggta ggaaccgtta    3000
ccagctggaa attcctgaga atttcaccac tcgcaatttg ccagaagaat acgagttgaa    3060
atctaccaag aagggctgta acgatactg gaccaaaact attgaaaaga agttggctaa    3120
tctcataaat gctgaagaac ggagggatgt atcattgaag gactgcatgc ggcgactgtt    3180
ctataacttt gataaaaatt acaaggactg gcagtctgct gtagagtgta tcgcagtgtt    3240
ggatgtttta ctgtgcctgg ctaactatag tcgaggggt gatggtccta tgtgtcgccc    3300
agtaattctg ttgccggaag atacccccccc cttcttagag cttaaaggat cacgccatcc    3360
ttgcattacg aagactttttt tggagatga ttttattcct aatgacattc taataggctg    3420
tgaggaagag gagcaggaaa atggcaaagc ctattgtgtg cttgttactg gaccaaatat    3480
gggggcaag tctacgctta tgagacaggc tggcttatta gctgtaatgg cccagatggg    3540
ttgttacgtc cctgctgaag tgtgcaggct cacaccaatt gatagagtgt ttactagact    3600
tggtgcctca gacagaataa tgtcaggtga agtacatttt tttgttgaat taagtgaaac    3660
tgccagcata ctcatgcatg caacagcaca ttctctggtg cttgtggatg aattaggaag    3720
aggtactgca acatttgatg ggacggcaat agcaaatgca gttgttaaag aacttgctga    3780
gactataaaa tgtcgtacat tattttcaac tcactaccat tcattagtag aagattattc    3840
tcaaaatgtt gctgtgcgcc taggacatat ggcatgcatg gtagaaaatg aatgtgaaga    3900
```

```
cccccagccag gagactatta cgttcctcta taaattcatt aagggagctt gtcctaaaag   3960
ctatggcttt aatgcagcaa ggcttgctaa tctcccagag gaagttattc aaaagggaca   4020
tagaaaagca agagaatttg agaagatgaa tcagtcacta cgattatttc gggaagtttg   4080
cctggctagt gaaaggtcaa ctgtagatgc tgaagctgtc cataaattgc tgactttgat   4140
taaggaatta tagactgact acattggaag ctttgagttg acttctgaca aggtggtaa    4200 attcagacaa cattatgatc taataaactt tatttttaa aaat                     4244
```

<210> SEQ ID NO 28
<211> LENGTH: 1128
<212> TYPE: PRT
<213> ORGANISM: Homo sapiens

<400> SEQUENCE: 28

```
Met Ser Arg Arg Lys Pro Ala Ser Gly Gly Leu Ala Ala Ser Ser Ser
 1               5                  10                  15

Ala Pro Ala Arg Gln Ala Val Leu Ser Arg Phe Phe Gln Ser Thr Gly
            20                  25                  30

Ser Leu Lys Ser Thr Ser Ser Thr Gly Ala Ala Asp Gln Val Asp
        35                  40                  45

Pro Gly Ala Ala Ala Ala Ala Pro Pro Ala Pro Ala Phe Pro Pro
    50                  55                  60

Gln Leu Pro Pro His Val Ala Thr Glu Ile Asp Arg Arg Lys Lys Arg
 65                  70                  75                  80

Pro Leu Glu Asn Asp Gly Pro Val Lys Lys Val Lys Lys Val Gln
            85                  90                  95

Gln Lys Glu Gly Gly Ser Asp Leu Gly Met Ser Gly Asn Ser Glu Pro
            100                 105                 110

Lys Lys Cys Leu Arg Thr Arg Asn Val Ser Lys Ser Leu Glu Lys Leu
        115                 120                 125

Lys Glu Phe Cys Cys Asp Ser Ala Leu Pro Gln Ser Arg Val Gln Thr
    130                 135                 140

Glu Ser Leu Gln Glu Arg Phe Ala Val Leu Pro Lys Cys Thr Asp Phe
145                 150                 155                 160

Asp Asp Ile Ser Leu Leu His Ala Lys Asn Ala Val Ser Ser Glu Asp
                165                 170                 175

Ser Lys Arg Gln Ile Asn Gln Lys Asp Thr Thr Leu Phe Asp Leu Ser
            180                 185                 190

Gln Phe Gly Ser Ser Asn Thr Ser His Glu Asn Leu Gln Lys Thr Ala
        195                 200                 205

Ser Lys Ser Ala Asn Lys Arg Ser Lys Ser Ile Tyr Thr Pro Leu Glu
    210                 215                 220

Leu Gln Tyr Ile Glu Met Lys Gln Gln His Lys Asp Ala Val Leu Cys
225                 230                 235                 240

Val Glu Cys Gly Tyr Lys Tyr Arg Phe Phe Gly Glu Asp Ala Glu Ile
                245                 250                 255

Ala Ala Arg Glu Leu Asn Ile Tyr Cys His Leu Asp His Asn Phe Met
            260                 265                 270

Thr Ala Ser Ile Pro Thr His Arg Leu Phe Val His Val Arg Arg Leu
        275                 280                 285

Val Ala Lys Gly Tyr Lys Val Gly Val Val Lys Gln Thr Glu Thr Ala
    290                 295                 300

Ala Leu Lys Ala Ile Gly Asp Asn Arg Ser Ser Leu Phe Ser Arg Lys
305                 310                 315                 320
```

```
Leu Thr Ala Leu Tyr Thr Lys Ser Thr Leu Ile Gly Glu Asp Val Asn
                325                 330                 335

Pro Leu Ile Lys Leu Asp Asp Ala Val Asn Val Asp Glu Ile Met Thr
            340                 345                 350

Asp Thr Ser Thr Ser Tyr Leu Leu Cys Ile Ser Glu Asn Lys Glu Asn
        355                 360                 365

Val Arg Asp Lys Lys Gly Asn Ile Phe Ile Gly Ile Val Gly Val
    370                 375                 380

Gln Pro Ala Thr Gly Glu Val Val Phe Asp Ser Phe Gln Asp Ser Ala
385                 390                 395                 400

Ser Arg Ser Glu Leu Glu Thr Arg Met Ser Ser Leu Gln Pro Val Glu
            405                 410                 415

Leu Leu Leu Pro Ser Ala Leu Ser Glu Gln Thr Glu Ala Leu Ile His
            420                 425                 430

Arg Ala Thr Ser Val Ser Val Gln Asp Asp Arg Ile Arg Val Glu Arg
            435                 440                 445

Met Asp Asn Ile Tyr Phe Glu Tyr Ser His Ala Phe Gln Ala Val Thr
    450                 455                 460

Glu Phe Tyr Ala Lys Asp Thr Val Asp Ile Lys Gly Ser Gln Ile Ile
465                 470                 475                 480

Ser Gly Ile Val Asn Leu Glu Lys Pro Val Ile Cys Ser Leu Ala Ala
            485                 490                 495

Ile Ile Lys Tyr Leu Lys Glu Phe Asn Leu Glu Lys Met Leu Ser Lys
            500                 505                 510

Pro Glu Asn Phe Lys Gln Leu Ser Ser Lys Met Glu Phe Met Thr Ile
            515                 520                 525

Asn Gly Thr Thr Leu Arg Asn Leu Glu Ile Leu Gln Asn Gln Thr Asp
            530                 535                 540

Met Lys Thr Lys Gly Ser Leu Leu Trp Val Leu Asp His Thr Lys Thr
545                 550                 555                 560

Ser Phe Gly Arg Arg Lys Leu Lys Lys Trp Val Thr Gln Pro Leu Leu
            565                 570                 575

Lys Leu Arg Glu Ile Asn Ala Arg Leu Asp Ala Val Ser Glu Val Leu
            580                 585                 590

His Ser Glu Ser Ser Val Phe Gly Gln Ile Glu Asn His Leu Arg Lys
            595                 600                 605

Leu Pro Asp Ile Glu Arg Gly Leu Cys Ser Ile Tyr His Lys Lys Cys
            610                 615                 620

Ser Thr Gln Glu Phe Phe Leu Ile Val Lys Thr Leu Tyr His Leu Lys
625                 630                 635                 640

Ser Glu Phe Gln Ala Ile Ile Pro Ala Val Asn Ser His Ile Gln Ser
                645                 650                 655

Asp Leu Leu Arg Thr Val Ile Leu Glu Ile Pro Glu Leu Leu Ser Pro
            660                 665                 670

Val Glu His Tyr Leu Lys Ile Leu Asn Glu Gln Ala Ala Lys Val Gly
            675                 680                 685

Asp Lys Thr Glu Leu Phe Lys Asp Leu Ser Asp Phe Pro Leu Ile Lys
            690                 695                 700

Lys Arg Lys Asp Glu Ile Gln Gly Val Ile Asp Glu Ile Arg Met His
705                 710                 715                 720

Leu Gln Glu Ile Arg Lys Ile Leu Lys Asn Pro Ser Ala Gln Tyr Val
                725                 730                 735
```

```
Thr Val Ser Gly Gln Glu Phe Met Ile Glu Ile Lys Asn Ser Ala Val
            740                 745                 750

Ser Cys Ile Pro Thr Asp Trp Val Lys Val Gly Ser Thr Lys Ala Val
            755                 760                 765

Ser Arg Phe His Ser Pro Phe Ile Val Glu Asn Tyr Arg His Leu Asn
            770                 775                 780

Gln Leu Arg Glu Gln Leu Val Leu Asp Cys Ser Ala Glu Trp Leu Asp
785                 790                 795                 800

Phe Leu Glu Lys Phe Ser Glu His Tyr His Ser Leu Cys Lys Ala Val
                805                 810                 815

His His Leu Ala Thr Val Asp Cys Ile Phe Ser Leu Ala Lys Val Ala
            820                 825                 830

Lys Gln Gly Asp Tyr Cys Arg Pro Thr Val Gln Glu Glu Arg Lys Ile
            835                 840                 845

Val Ile Lys Asn Gly Arg His Pro Val Ile Asp Val Leu Leu Gly Glu
            850                 855                 860

Gln Asp Gln Tyr Val Pro Asn Asn Thr Asp Leu Ser Glu Asp Ser Glu
865                 870                 875                 880

Arg Val Met Ile Ile Thr Gly Pro Asn Met Gly Gly Lys Ser Ser Tyr
                885                 890                 895

Ile Lys Gln Val Ala Leu Ile Thr Ile Met Ala Gln Ile Gly Ser Tyr
            900                 905                 910

Val Pro Ala Glu Glu Ala Thr Ile Gly Ile Val Asp Gly Ile Phe Thr
            915                 920                 925

Arg Met Gly Ala Ala Asp Asn Ile Tyr Lys Gly Arg Ser Thr Phe Met
            930                 935                 940

Glu Glu Leu Thr Asp Thr Ala Glu Ile Ile Arg Lys Ala Thr Ser Gln
945                 950                 955                 960

Ser Leu Val Ile Leu Asp Glu Leu Gly Arg Gly Thr Ser Thr His Asp
                965                 970                 975

Gly Ile Ala Ile Ala Tyr Ala Thr Leu Glu Tyr Phe Ile Arg Asp Val
            980                 985                 990

Lys Ser Leu Thr Leu Phe Val Thr His Tyr Pro Pro Val Cys Glu Leu
            995                 1000                1005

Glu Lys Asn Tyr Ser His Gln Val Gly Asn Tyr His Met Gly Phe Leu
            1010                1015                1020

Val Ser Glu Asp Glu Ser Lys Leu Asp Pro Gly Ala Ala Glu Gln Val
1025                1030                1035                1040

Pro Asp Phe Val Thr Phe Leu Tyr Gln Ile Thr Arg Gly Ile Ala Ala
                1045                1050                1055

Arg Ser Tyr Gly Leu Asn Val Ala Lys Leu Ala Asp Val Pro Gly Glu
            1060                1065                1070

Ile Leu Lys Lys Ala Ala His Lys Ser Lys Glu Leu Glu Gly Leu Ile
            1075                1080                1085

Asn Thr Lys Arg Lys Arg Leu Lys Tyr Phe Ala Lys Leu Trp Thr Met
            1090                1095                1100

His Asn Ala Gln Asp Leu Gln Lys Trp Thr Glu Glu Phe Asn Met Glu
1105                1110                1115                1120

Glu Thr Gln Thr Ser Leu Leu His
                1125

<210> SEQ ID NO 29
<211> LENGTH: 4374
<212> TYPE: DNA
```

<213> ORGANISM: Homo sapiens

<400> SEQUENCE: 29

```
gggcacgagc cctgccatgt ctcgccggaa gcctgcgtcg ggcggcctcg ctgcctccag      60
ctcagcccct gcgaggcaag cggttttgag ccgattcttc cagtctacgg gaagcctgaa     120
atccacctcc tcctcacag gtgcagccga ccaggtggac cctggcgctg cagcggccgc     180
agcgccccca gcgcccgcct tcccgcccca gctgccgccg cacgtagcta cagaaattga     240
cagaagaaag aagagaccat tggaaaatga tgggcctgtt aaaagaaag taaagaaagt     300
ccaacaaaag gaaggaggaa gtgatctggg aatgtctggc aactctgagc caaagaaatg     360
tctgaggacc aggaatgttt caaagtctct ggaaaaattg aaagaattct gctgcgattc     420
tgcccttcct caaagtagag tccagacaga atctctgcag gagagatttg cagttctgcc     480
aaaatgtact gattttgatg atatcagtct tctacacgca aagaatgcag tttcttctga     540
agattcgaaa cgtcaaatta atcaaaagga cacaacactt tttgatctca gtcagtttgg     600
atcatcaaat acaagtcatg aaaatttaca gaaaactgct tccaaatcag ctaacaaacg     660
gtccaaaagc atctatacgc cgctagaatt acaatacata gaaatgaagc agcagcacaa     720
agatgcagtt ttgtgtgtgg aatgtggata taagtataga ttctttgggg aagatgcaga     780
gattgcagcc cgagagctca atatttattg ccatttagat cacaacttta tgacagcaag     840
tataccctact cacagactgt tgttcatgt acgccgcctg gtggcaaaag gatataaggt     900
gggagttgtg aagcaaactg aaactgcagc attaaaggcc attggagaca cagaagttc     960
actcttttcc cggaaattga ctgccctttta tacaaaatct acacttattg gagaagatgt    1020
gaatccccta atcaagctgg atgatgctgt aaatgttgat gagataatga ctgatacttc    1080
taccagctat cttctgtgca tctctgaaaa taaggaaaat gttagggaca aaaaaaggg    1140
caacattttt attggcattg tgggagtgca gcctgccaca ggcgaggttg tgtttgatag    1200
tttccaggac tctgcttctc gttcagagct agaaacccgg atgtcaagcc tgcagccagt    1260
agagctgctg cttccttcgg ccttgtccga gcaaacagag gcgctcatcc acagagccac    1320
atctgttagt gtgcaggatg acagaattcg agtcgaaagg atggataaca tttattttga    1380
atacagccat gctttccagg cagttacaga gttttatgca aaagatacag ttgacatcaa    1440
aggttctcaa attatttctg gcattgttaa cttagagaag cctgtgattt gctctttggc    1500
tgccatcata aaatacctca agaattcaa cttggaaaag atgctctcca aacctgagaa    1560
ttttaaacag ctatcaagta aaatggaatt tatgacaatt aatggaacaa cattaaggaa    1620
tctggaaatc ctacagaatc agactgtatt gaaaaccaaa ggaagtttgc tgtgggtttt    1680
agaccacact aaaacttcat ttgggagacg gaagttaaag aagtgggtga cccagccact    1740
ccttaaatta agggaaataa atgcccggct tgatgctgta tcggaagttc tccattcaga    1800
atctagtgtg tttggtcaga tagaaaatca tctacgtaaa ttgcccgaca tagagaggg    1860
actctgtagc atttatcaca aaaaatgttc tacccaagag ttcttcttga ttgtcaaaac    1920
tttatatcac ctaaagtcag aatttcaagc aataatacct gctgttaatt cccacattca    1980
gtcagacttg ctccggaccg ttattttaga aattcctgaa ctcctcagtc cagtggagca    2040
ttacttaaag atactcaatg aacaagctgc caaagtgggg gataaaactg aattatttaa    2100
agacctttct gacttcccctt taataaaaaa gaggaaggat gaaattcaag gtgttattga    2160
cgagatccga atgcatttgc aagaaatacg aaaaatacta aaaatccctt ctgcacaata    2220
tgtgacagta tcaggacagg agtttatgat agaaataaag aactctgctg tatcttgtat    2280
```

```
accaactgat tgggtaaagg ttggaagcac aaaagctgtg agccgctttc actctccttt    2340
tattgtagaa aattacagac atctgaatca gctccgggag cagctagtcc ttgactgcag    2400
tgctgaatgg cttgattttc tagagaaatt cagtgaacat tatcactcct tgtgtaaagc    2460
agtgcatcac ctagcaactg ttgactgcat tttctccctg gccaaggtcg ctaagcaagg    2520
agattactgc agaccaactg tacaagaaga aagaaaaatt gtaataaaaa atggaaggca    2580
ccctgtgatt gatgtgttgc tgggagaaca ggatcaatat gtcccaaata atacagattt    2640
atcagaggac tcagagagag taatgataat taccggacca acatgggtg gaaagagctc    2700 ctacataaaa caagttgcat tgattaccat catggctcag attggctcct atgttcctgc    2760
agaagaagcg acaattggga ttgtggatgg cattttcaca aggatgggtg ctgcagacaa    2820
tatatataaa ggacggagta catttatgga agaactgact gacacagcag aataatcag    2880 aaaagcaaca tcacagtcct tggttatctt ggatgaacta ggaagaggga cgagcactca    2940
tgatggaatt gccattgcct atgctacact tgagtatttc atcagagatg tgaaatcctt    3000
aaccctgttt gtcacccatt atccgccagt ttgtgaacta gaaaaaaatt actcacacca    3060
ggtggggaat taccacatgg gattcttggt cagtgaggat gaaagcaaac tggatccagg    3120
cgcagcagaa caagtccctg attttgtcac cttcctttac caaataacta gaggaattgc    3180
agcaaggagt tatggattaa atgtggctaa actagcagat gttcctggag aaattttgaa    3240
gaaagcagct cacaagtcaa aagagctgga aggattaata aatacgaaaa gaaagagact    3300
caagtatttt gcaaagttat ggacgatgca taatgcacaa gacctgcaga agtggacaga    3360
ggagttcaac atggaagaaa cacagacttc tcttcttcat taaaatgaag actacatttg    3420
tgaacaaaaa atggagaatt aaaaatacca actgtacaaa ataactctcc agtaacagcc    3480
tatctttgtg tgacatgtga gcataaaatt atgaccatgg tatattccta ttggaaacag    3540
agaggttttt ctgaagacag tcttttccaa gtttctgtct tcctaacttt tctacgtata    3600
aacactcttg aatagacttc cactttgtaa ttagaaaatt ttatggacag taagtccagt    3660
aaagccttaa gtgcagaat ataattccca agcttttgga gggtgatata aaaatttact    3720 tgatatttt atttgtttca gttcagataa ttggcaactg ggtgaatctg caggaatct    3780 atccattgaa ctaaaataat tttattatgc aaccagttta tccaccaaga acataagaat    3840 ttttttataag tagaaagaat tggccaggca tggtggctca tgcctgtaat cccagcactt    3900
tgggaggcca aggtaggcag atcacctgag gtcaggagtt caagaccagc ctggccaaca    3960
tggcaaaacc ccatctttac taaaaatata agtacatct ctactaaaaa tacgaaaaaa    4020
ttagctgggc atggtggcgc acacctgtag tcccagctac tccggaggct gaggcaggag    4080
aatctcttga acctgggagg cggaggttgc aatgagccga gatcacgtca ctgcactcca    4140
gcttgggcaa cagagcaaga ctccatctca aaaagaaaa aagaaagaa atagaattat    4200 caagctttta aaaactagag cacagaagga ataaggtcat gaaatttaaa aggttaaata    4260
ttgtcatagg attaagcagt ttaaagattg ttggatgaaa ttatttgtca ttcattcaag    4320
taataaatat ttaatgaata cttgctataa aaaaaaaaaa aaaaaaaaaa aaaa         4374
```

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

```
<400> SEQUENCE: 30
gatatctcca ctgacgtaag                                               20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 31
tgttgccggt cttgcgatg                                                19

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 32
cccgatctag taacatagat g                                             21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 33
cagtctggat cgcgaaaact g                                             21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 34
ggtgattacc gacgaaaacg                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 35
agtgaagggc gaacagttcc                                               20

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer
```

```
<400> SEQUENCE: 36
gagtattgcc aacgaacc                                                  18

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 37
gtatcaccgc gtctttgatc                                                20

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 38
cgaaacgcag cacgatacg                                                 19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 39
gttcaacgct gacatcacc                                                 19

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 40
catgttcatc tgcccagtcg                                                20

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 41
gctttggaca taccatcc                                                  18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 42
```

```
caccgaagtt catgccag                                           18

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 43
tgactacttt tgacttcagc c                                       21

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 44
aaccattcaa catttttaac cc                                      22
```